United States Patent
Muyo et al.

(10) Patent No.: US 12,059,210 B2
(45) Date of Patent: Aug. 13, 2024

(54) OPHTHALMIC OPTICAL SYSTEM, OPHTHALMIC OBJECTIVE LENS, AND OPHTHALMIC DEVICE

(71) Applicants: NIKON CORPORATION, Tokyo (JP); OPTOS PLC, Dunfermline (GB)

(72) Inventors: Gonzalo Muyo, Dunfermline (GB); Alistair Gorman, Dunfermline (GB); David M. Williamson, Tucson, AZ (US); Makoto Fujimoto, Tokyo (JP); Yasufumi Nishi, Edinburgh (GB); Azuna Nonaka, Yokohama (JP); Katsuya Watanabe, Yokohama (JP); Miwako Yoshida, Yokohama (JP); Kyoya Tokunaga, Yokohama (JP); Masahiro Mizuta, Yokohama (JP)

(73) Assignees: NIKON CORPORATION, Tokyo (JP); OPTOS PLC, Dunfermline (GB)

(*) Notice: Subject to any disclaimer, the term of this patent is extended or adjusted under 35 U.S.C. 154(b) by 885 days.

(21) Appl. No.: 17/035,152

(22) Filed: Sep. 28, 2020

(65) Prior Publication Data
US 2021/0093194 A1 Apr. 1, 2021

Related U.S. Application Data

(63) Continuation of application No. PCT/JP2019/012941, filed on Mar. 26, 2019.
(Continued)

(51) Int. Cl.
*A61B 3/14* (2006.01)
*A61B 3/00* (2006.01)

(52) U.S. Cl.
CPC .............. *A61B 3/14* (2013.01); *A61B 3/0008* (2013.01); *A61B 3/0041* (2013.01)

(58) Field of Classification Search
CPC ........ A61B 3/14; A61B 3/0008; A61B 3/0041
(Continued)

(56) References Cited

U.S. PATENT DOCUMENTS

| 6,133,935 A | 10/2000 | Fujibayashi |
| 2009/0027769 A1 | 1/2009 | Saito |

(Continued)

FOREIGN PATENT DOCUMENTS

| JP | H10-232347 A | 9/1998 |
| JP | 2016-104105 A | 6/2016 |

(Continued)

OTHER PUBLICATIONS

Japanese Office Action for Japanese Application No. 2023-018735 dated Mar. 12, 2024 (5 pages).

*Primary Examiner* — Joseph P Martinez
*Assistant Examiner* — Grant A Gagnon
(74) *Attorney, Agent, or Firm* — FOLEY & LARDNER LLP

(57) ABSTRACT

The ophthalmic optical system is configured to apply an angular scanning light ray to an eye. $M=|\omega out/\omega in|$ is defined, where $\omega in$ represents an angle between an incident light ray to the ophthalmic optical system and an optical axis of the ophthalmic optical system, and $\omega out$ represents an angle between an exiting light ray exiting from the ophthalmic optical system toward the eye and the optical axis. The ophthalmic optical system satisfies a conditional expression $Mpar<Mmax$, where $Mpar$ represents M in a case that the incident light ray is a paraxial ray, $Mmax$ represents M in a case that the incident light ray is a ray of a maximum angle of $\omega in$.

3 Claims, 44 Drawing Sheets

Related U.S. Application Data

(60) Provisional application No. 62/650,309, filed on Mar. 30, 2018.

(58) Field of Classification Search
USPC .......................................................... 351/206
See application file for complete search history.

(56) References Cited

U.S. PATENT DOCUMENTS

| | | |
|---|---|---|
| 2014/0320813 A1 | 10/2014 | Yoshida |
| 2015/0216408 A1 | 8/2015 | Brown |
| 2016/0150953 A1 | 6/2016 | Sasaki |
| 2021/0093194 A1 | 4/2021 | Muyo et al. |

FOREIGN PATENT DOCUMENTS

| | | |
|---|---|---|
| JP | 2017-192442 A | 10/2017 |
| JP | 2010-008989 A | 1/2020 |
| JP | 7227408 B2 | 2/2023 |
| WO | WO-2018/043657 A1 | 3/2018 |

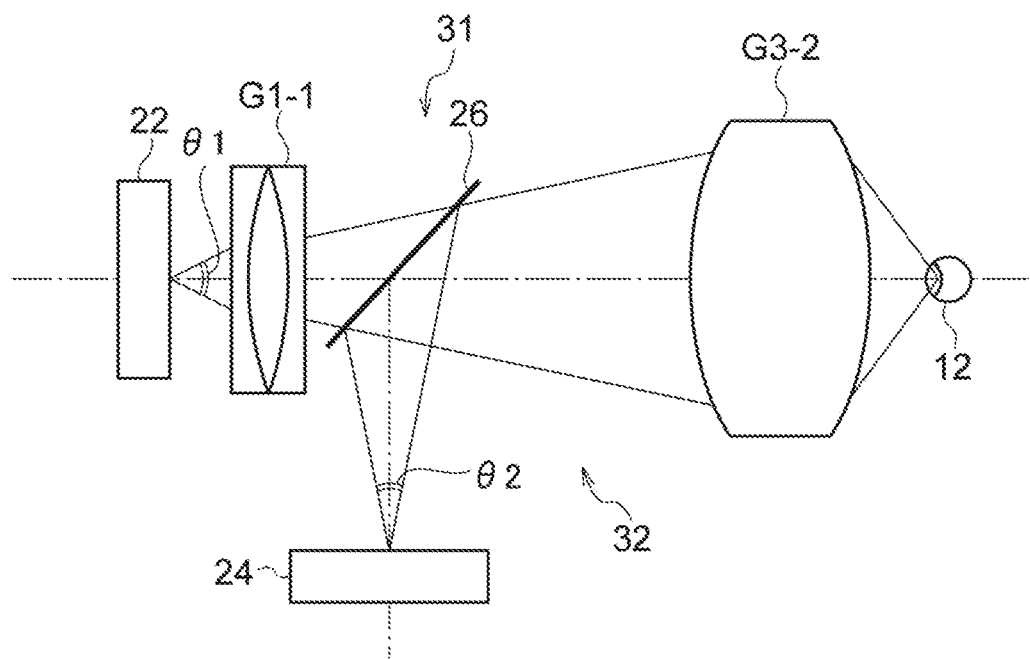

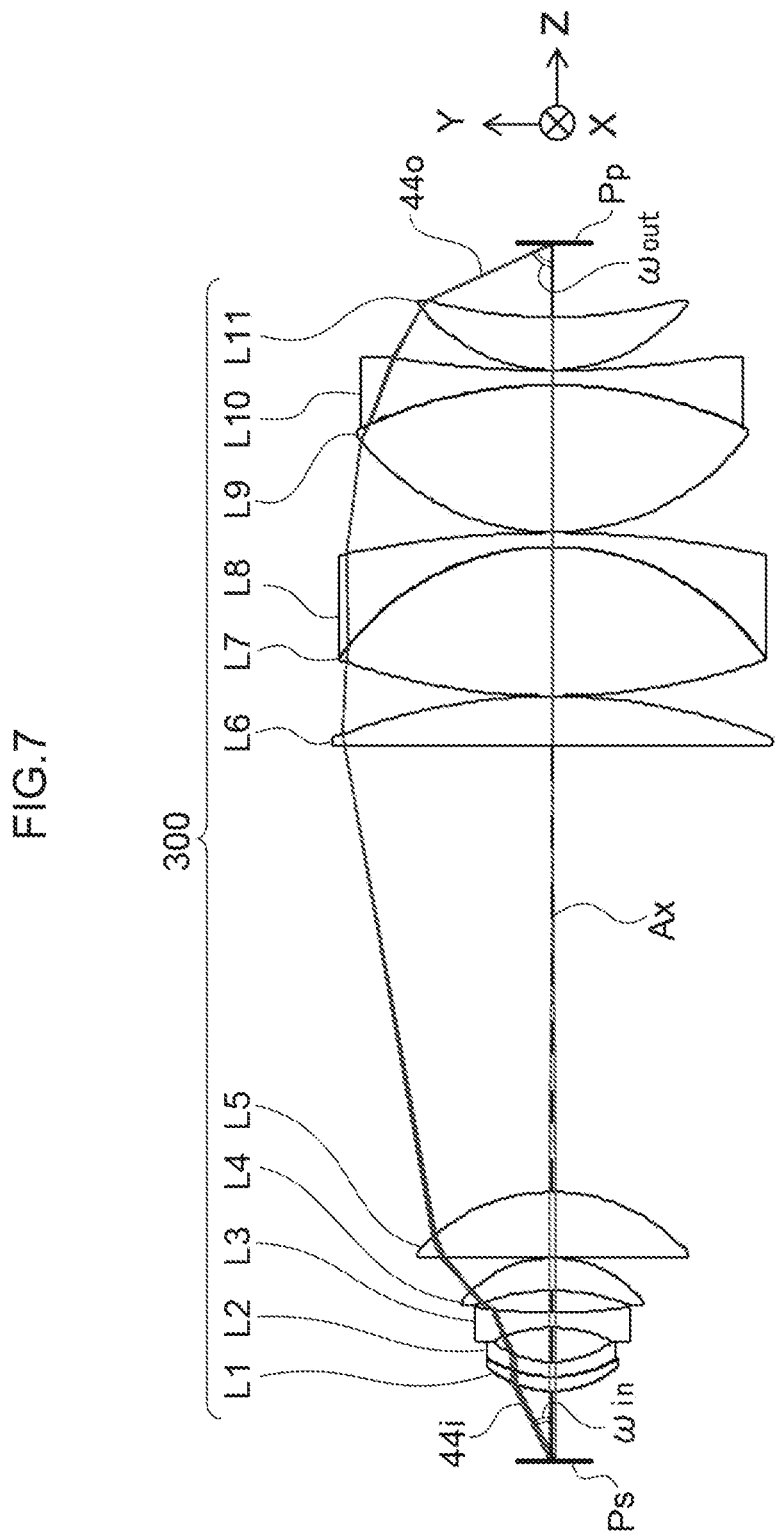

FIG.13 PRACTICAL EXAMPLE 1-1

FIG.16 PRACTICAL EXAMPLE 1-2

FIG.19 PRACTICAL EXAMPLE 2-1

FIG.22 PRACTICAL EXAMPLE 2-2

FIG.28 PRACTICAL EXAMPLE 3-2

FIG.31 PRACTICAL EXAMPLE 4-1

FIG.34 PRACTICAL EXAMPLE 5-1

PRACTICAL EXAMPLE 6-1

FIG.36 PRACTICAL EXAMPLE 7-1

FIG.38 PRACTICAL EXAMPLE 9-1

FIG.39 PRACTICAL EXAMPLE 10-1

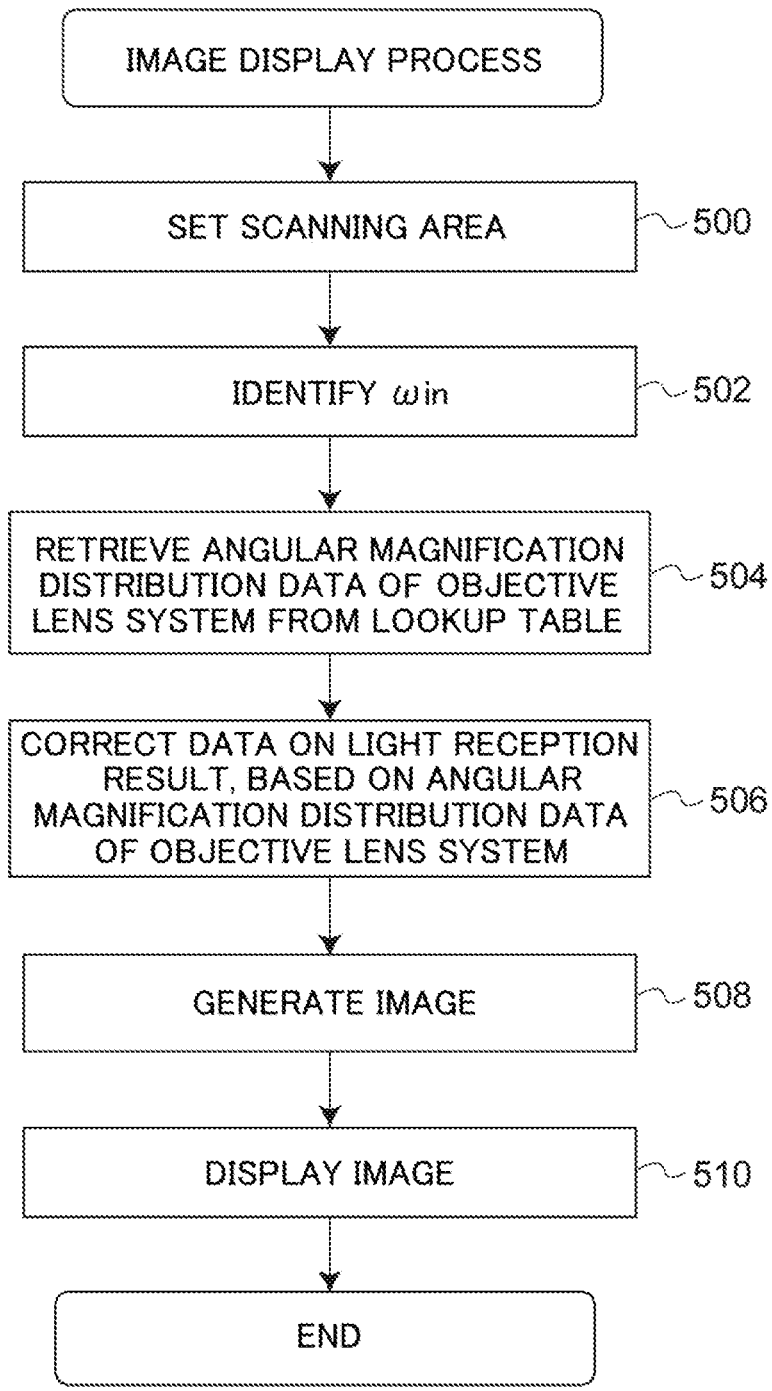

OPHTHALMIC OPTICAL SYSTEM, OPHTHALMIC OBJECTIVE LENS, AND OPHTHALMIC DEVICE

CROSS-REFERENCE TO RELATED APPLICATIONS

This application is a continuation application of International Application No. PCT/JP2019/012941 filed Mar. 26, 2019, the disclosure of which is incorporated herein by reference in its entirety. Further, this application claims priority from U.S. Patent Application No. 62/650,309, filed Mar. 30, 2018, the disclosure of which is incorporated herein by reference in its entirety.

JOINT RESEARCH AGREEMENT

The present disclosure and all inventions herein were made by, or on behalf of, parties to a joint research agreement that was in effect on or before the effective filing date of the present disclosure. The present disclosure and all inventions herein were made as a result of activities undertaken within the scope of the joint research agreement. The parties to the joint research agreement are: Nikon Corporation and Optos PLC.

TECHNICAL FIELD

The technology of the present disclosure relates to an ophthalmic optical system, an ophthalmic objective lens, and an ophthalmic device.

RELATED ART

Patent Documents 1, 2, and 3 disclose devices that capture images of eyes using scanning laser ophthalmoscopes and optical coherence tomography systems.

PRIOR ART DOCUMENT

Patent Documents

Patent Document 1: US 2015/0216408 A1
Patent Document 2: US 2016/0150953 A1
Patent Document 3: US 2014/0320813 A1

For convenience sake, a scanning laser ophthalmoscope is abbreviated as "SLO". Optical coherence tomography is abbreviated as "OCT", as in these documents.

SUMMARY

According to the first aspect of the technology of the present disclosure, an ophthalmic optical system configured to apply an angular scanning light ray to a side of an eye, wherein:
(1) $\omega \text{min}$ represents an angle formed between an incident light ray into the ophthalmic optical system and an optical axis of the ophthalmic optical system,
(2) $\omega \text{out}$ represents an angle formed between an exit light ray from the ophthalmic optical system to the side of the eye and the optical axis, and
(3) M is defined as $M=|\omega \text{out}/\omega \text{in}|$,
the following conditional expression is satisfied:

$$M\text{par} < M\text{max}$$

wherein Mpar represents M in a case that the incident light ray is a paraxial ray, and Mmax represents M in a case that the incident light ray is a ray of a maximum angle of $\omega \text{in}$.

According to the second aspect of the technology of the present disclosure, an ophthalmic optical system configured to apply an angular scanning light beam to a side of an eye, wherein:
(1) $\omega \text{max}$ represents a maximum angle formed between an exit scan beam from the ophthalmic optical system and an optical axis of the ophthalmic optical system,
(2) Pmax represents a diameter of the exit scan beam in a meridional direction at a pupil position of the eye, where the exit scan beam forms an maximum angle of $\omega \text{max}$ with respect to the optical axis, and
(3) Pmin represents a diameter of the exit scan beam in the meridional direction at the pupil position of the eye, in a case that the exit scan beam forms a minimum angle with respect to the optical axis,
the following conditional expression is satisfied:

$$P\text{max} < P\text{min} \times 0.7/(\cos(\omega \text{max})).$$

According to the third aspect of the technology of the present disclosure, an ophthalmic optical system configured to apply an angular scanning light ray to a side of an eye, wherein:
(1) $\omega \text{min}$ represents an angle formed between an incident light ray into the ophthalmic optical system and the optical axis of the ophthalmic optical system,
(2) $\omega \text{out}$ represents an angle formed between an exit light ray from the ophthalmic optical system to the side of the eye and the optical axis, and
(3) M is defined as $M=|\omega \text{out}/\omega \text{in}|$,
the following conditional expression is satisfied:

$$Mc < Mp$$

wherein Mc represents M in a central portion area of the eye to be scanned including a cross point with the optical axis, and
Mp represents M in a peripheral portion area of the eye to be scanned.

According to the fourth aspect of the technology of the present disclosure, an ophthalmic objective lens configured to transfer an incoming light ray to an outgoing light ray, comprising:
a plurality of lenses arranged along an optical axis, such that the following conditional expression is satisfied:

$$M\text{par} < M\text{max}$$

wherein
$\omega \text{in}$ is an angle of the incoming light ray with respect to the optical axis,
$\omega \text{out}$ is an angle of the outgoing light ray with respect to the optical axis,
M is defined as $M=|\omega \text{out}/\omega \text{in}|$,
Mpar is M where the incoming light ray is a paraxial ray, and
Mmax is M where the incoming light ray is a ray of a maximum angle of view.

According to the fifth aspect of the technology of the present disclosure, an ophthalmic objective lens configured to transfer an incoming light beam to an outgoing light beam, comprising:
a plurality of lenses arranged along an optical axis, such that the following conditional expression is satisfied:

$$P\text{max} < P\text{min} \times 0.7/(\cos(\omega \text{max}));$$

wherein
  ωmax is a maximum angle of the outgoing light beam from the ophthalmic objective lens with respect to the optical axis,
  Pmax is a diameter in a meridional direction of the outgoing light beam intersecting a plane perpendicular to the optical axis, the plane located at the position where the outgoing light beam intersects the optical axis, where the outgoing light beam forms an angle of ωmax with respect to the optical axis, and
  Pmin is a diameter in the meridional direction of the outgoing light beam intersecting the plane, where the angle of the outgoing light beam from the ophthalmic objective lens with respect to the optical axis is minimum.

BRIEF DESCRIPTION

FIG. 6B is a schematic diagram showing the configuration of another modification example of the complex objective lens system:

FIG. 7 is a drawing to explain an incident angle min and an exiting angle out of scanned light in an objective lens system;

FIG. 43 is a flowchart showing the operation of an image processor.

DESCRIPTION OF EMBODIMENT

Figure 1:
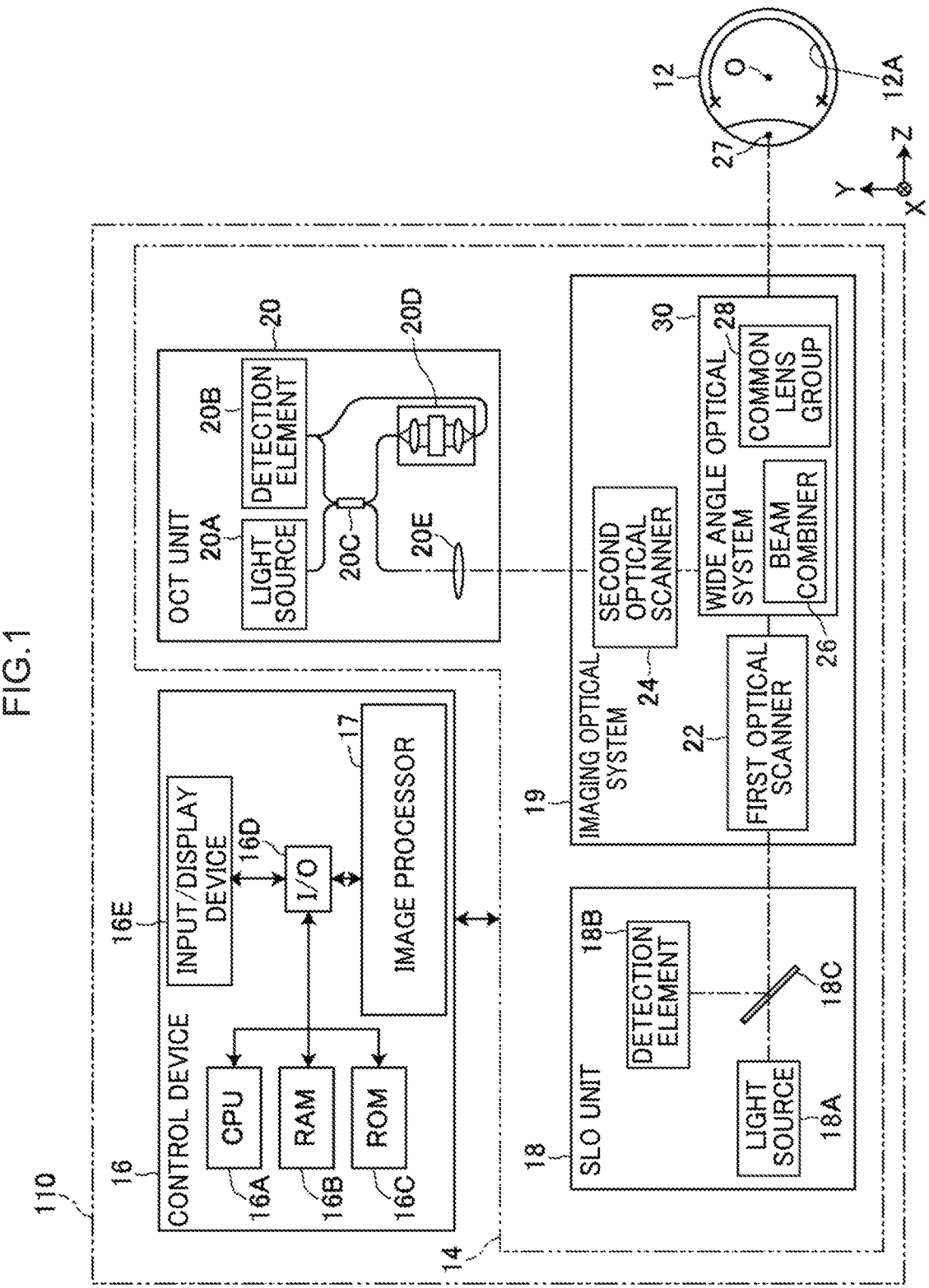
FIG. 1 is a schematic configuration diagram showing an example of the entire configuration of an ophthalmic device.

An embodiment will be described below in detail with reference to the drawings.

First, an example of the configuration of an ophthalmic device 110 will be described with reference to FIG. 1. The ophthalmic device 110 includes an imaging device 14 and a control device 16. The imaging device 14 includes an SLO unit 18 and an OCT unit 20, and captures a findus image of a fundus oculi of an eye 12. An image captured by the SLO unit 18 is hereinafter referred to as an SLO image. An image captured by the OCT unit 20 is hereinafter referred to as an OCT image.

The control device 16 is realized by a computer having a CPU (central processing unit) 16A, a RAM (random access memory) 16B, a ROM (read-only memory) 16C, and an input and output (I/O) port 16D.

The control device 16 includes an input/display device 16E connected to the CPU 16A through the I/O port 16D. The input/display device 16E has a graphic user interface on which an image of the eye 12 is displayed, and through which various commands are received from a user. As an example of the graphic user interface, there is a touch panel display.

The control device 16 includes an image processor 17 connected to the I/O port 16D. The image processor 17 generates an image of the eye 12, based on data obtained by the imaging device 14. Note that, the control device 16 may be connected to a network through a not-shown communication interface.

The imaging device 14 is operated under control of the control device 16. The imaging device 14 includes the SLO unit 18, an imaging optical system 19, and the OCT unit 20. The imaging optical system 19 includes a first optical scanner 22, a second optical scanner 24, and a wide angle optical system 30. The wide angle optical system 30 includes an objective lens system (not shown in FIG. 1) having a common lens group 28, and a beam combiner 26.

The first optical scanner 22 scans light emitted from the SLO unit 18 in two dimensions in an X direction and a Y direction. The second optical scanner 24 scans light emitted from the OCT unit 20 in two dimensions in the X direction and the Y direction. The first optical scanner 22 and the second optical scanner 24 may be any optical elements as long as they can deflect light beams, and, for example, polygon mirrors, galvanometer mirrors, or the like can be used. Alternatively, combinations thereof may be used.

Note that, in this application, "X direction" refers to a horizontal direction in a case where the ophthalmic device 110 is mounted in a horizontal plane. "Y direction" refers to a vertical direction with respect to the horizontal plane, and "Z direction" refers to a vertical direction with respect to both of the X direction and the Y direction.

The imaging optical system 19 includes a wide angle optical system 30. The wide angle optical system 30 realizes observation of a wide FOV (field of view) in the findus oculi. The FOV 12A represents an area that can be imaged by the imaging device 14. The FOV 12A may be referred to as a viewing angle. In this embodiment, the viewing angle is defined by an internal irradiation angle and an external irradiation angle. The external irradiation angle is an irradiation angle that defines an irradiation angle of a light beam emitted from the ophthalmic device 110 to the eye 12 with respect to a pupil 27. The internal irradiation angle is an irradiation angle that defines an irradiation angle of a light beam emitted to the fundus oculi with respect to the center O of an eye ball. The external irradiation angle and the internal irradiation angle have correspondence relationship. For example, in a case where the external irradiation angle is 120 degrees, the internal irradiation angle corresponds to approximately 160 degrees.

As shown in FIG. 1, an SLO system is realized by the control device 16, the SLO unit 18, and the imaging optical system 19. The SLO system enables fundus imaging of the wide FOV 12A, owing to provision of the wide angle optical system 30. The SLO unit 18 includes a light source 18A, a detection element 18B, and a beam splitter 18C. Note that, the detection element 18B is an example of a light reception unit according to the technology of the present disclosure. Light emitted from the light source 18A is incident on the imaging optical system 19 through the beam splitter 18C. The incident light into the imaging optical system 19 is scanned by the first optical scanner 22 in the X direction and the Y direction. The scanned light is applied to the findus oculi through the wide angle optical system 30 and the pupil 27. The light is reflected from the findus oculi, and is incident on the SLO unit 18 through the wide angle optical system 30 and the first optical scanner 22. The reflected light incident on the SLO unit is reflected by the beam splitter 18C, and received by the detection element 18B. The image processor 17 generates an SLO image based on the signal detected by the detection element 18B.

As shown in FIG. 1, an OCT system is realized by the control device 16, the OCT unit 20, and the imaging optical system 19. The OCT system enables findus imaging of the wide FOV 12A, owing to provision of the wide angle optical system 30. The OCT unit 20 includes a light source 20A, a detection element 20B, an optical coupler 20C, an optical coupler 20F, a reference optical system 20D, and a collimator lens 20E. Note that, the detection element 20B is an example of a light reception unit according to the technology of the present disclosure. Light emitted from the light source 20A is divided by the optical coupler 20C. One of the divided light rays is collimated into parallel light by the collimator lens 20E, and thereafter is incident on the imaging optical system 19, as measurement light. The measurement light is scanned by the second optical scanner 24 in the X direction and the Y direction. The scanned light is applied to the fundus oculi through the wide angle optical system 30 and the pupil 27. The light is reflected from the fundus oculi, and is incident on the OCT unit 20 through the wide angle optical system 30 and the second optical scanner 24. The other of the light rays divided by the optical coupler 20C is incident on the reference optical system 20D, as reference light. The reference light and the measurement light reflected from the fundus oculi interfere in the optical coupler 20F, and generate interference light. The interference light is received by the detection element 20B. The image processor 17 generates an OCT image based on the signal detected by the detection element 20B. Note that, as a method for OCT, SD-OCT (spectral-domain OCT) or SS-OCT (swept-source OCT) may be used.

<Complex Objective Lens System for SLO and OCT>

Next, the configuration of the wide angle optical system 30 included in the imaging optical system 19 will be described with reference to FIG. 2. Note that, light that exits from the SLO unit 18 and is incident on the imaging optical system 19 is hereinafter referred to as "SLO light", and light that exits from the OCT unit 20 and is incident on the imaging optical system 19 is hereinafter referred to as "OCT light" In this embodiment, the SLO light and the OCT light incident on the imaging optical system 19 are configured to be approximately parallel light.

Figure 2:
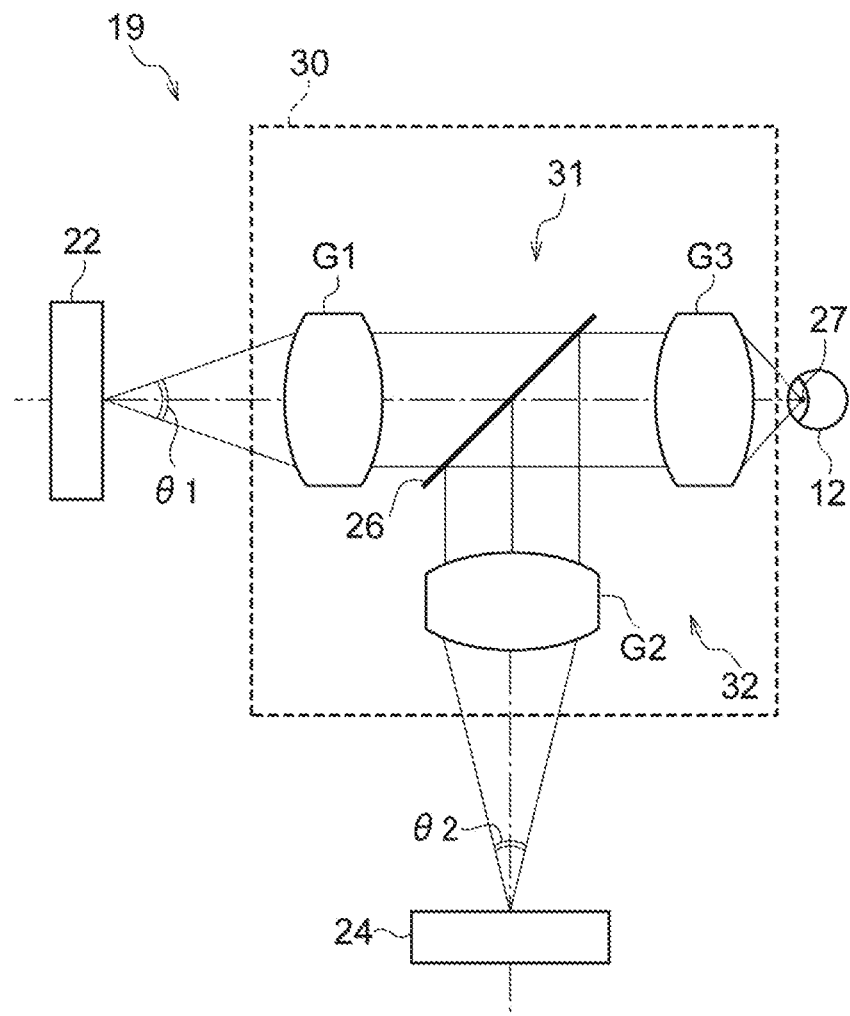
FIG. 2 is a schematic diagram showing an example of the schematic configuration of a wide angle optical system included in the ophthalmic device.

FIG. 2 is a schematic diagram showing an example of the schematic configuration of the imaging optical system 19. As shown in FIG. 2, the wide angle optical system 30 has such a configuration that an SLO objective lens system 31 used for capturing an SLO image and an OCT objective lens system 32 used for capturing an OCT image are combined using the beam combiner 26. Each of the SLO objective lens system 31 and the OCT objective lens system 32 is an example of an ophthalmic optical system according to the technology of the present disclosure, an example of an ophthalmic objective lens according to the technology of the present disclosure, and an example of an objective lens according to the technology of the present disclosure.

The SLO objective lens system 31 is configured to include a first lens group G1 and a third lens group G3. The OCT objective lens system 32 is configured to include a second lens group G2 and the third lens group G3. The first lens group G1 is an SLO-specific lens group. The second lens group G2 is an OCT-specific lens group. The third lens group G3 is an example of the common lens group 28 shown in FIG. 1. The SLO objective lens system 31 has an optical path passing through the beam combiner 26, and the beam combiner 26 is disposed between the first lens group G1 and the third lens group G3. The beam combiner 26 is also disposed in an optical path between the second lens group G2 and the third lens group G3, and the OCT objective lens system 32 has a bent optical path, i.e. an optical path bent by the beam combiner 26. In other words, the SLO objective lens system 31 and the OCT objective lens system 32 have the third lens group G3 on the side of the eye 12 relative to the beam combiner 26, as the common lens group 28.

In this embodiment, light having different wavelengths are used as the SLO light and the OCT light, and a dichroic mirror having wavelength dependence is used as the beam combiner 26. The beam combiner 26 of FIG. 2 has the function of combining an optical path of the SLO light heading for the side of the eye 12 and an optical path of the OCT light heading for the side of the eye 12. As for light that has been incident on the eye 12 and is reflected from the eye 12, the beam combiner 26 also has the function of separating between an optical path of reflected light of the SLO light and an optical path of reflected light of the OCT light, and leading the reflected light of the SLO light to the first lens group G1, while leading the reflected light of the OCT light to the second lens group G2.

As shown in FIG. 2, since the SLO objective lens system 31 and the OCT objective lens system 32 share the lens group on the side of the eye 12, using the element having light combining and separating functions, such as the dichroic mirror, the complex objective lens system in which the SLO objective lens system 31 and the OCT objective lens system 32 are combined can be configured. Accordingly, the single device can capture an ultra-wide-angle fundus image and a tomographic image of a retina in an ultra-wide-angle findus portion.

Note that, as the SLO light, one type of light having a wavelength in the visible region, or several types of light having wavelengths in the visible region may be used. For example, three types of light having a wavelength of 450 nm, a wavelength of 520 nm, and a wavelength of 638 nm may be used as the SLO light, to obtain a color SLO image. As the OCT light, infrared light of a wavelength of 800 to 1000 nm may be used. Since the SLO light and the OCT light have different wavelengths, the SLO objective lens system 31 and the OCT objective lens system 32 are configured such that the first lens group G1 corrects a chromatic aberration produced by the third lens group G3 on the side of the eye 12 relative to the beam combiner 26 in accordance with the wavelength of the SLO light, while the second lens group G2 corrects the chromatic aberration in accordance with the wavelength of the OCT light.

The SLO objective lens system 31 is an focal optical system, and is configured such that the position of the first optical scanner 22 (the position of a scanning center of the first optical scanner 22) and the pupil position of the eye 12 have a conjugate relationship. The OCT objective lens system 32 is also an a focal optical system, and is configured such that the position of the second optical scanner 24 (the position of a scanning center of the second optical scanner 24) and the pupil position of the eye 12 have a conjugate relationship. Note that, in this application "conjugate relationship" is not limited to a perfect conjugate relationship, but denotes a conjugate relationship having an error allowed in advance, as a manufacturing error, an error due to a secular variation, and the like. In this application, "afocal optical system" is not limited to a perfect afocal optical system, but denotes an afocal optical system having an error allowed in advance, as a manufacturing error, an error due to a secular variation, and the like.

The operation of the imaging optical system 19 having the above configuration will be described. An operation relating to SLO imaging will be first described. The parallel SLO light that is incident from the SLO unit 18 into the imaging optical system 19 is angularly scanned by the first optical scanner 22, such as a polygon mirror. The angularly scanned parallel SLO light sequentially passes through the first lens group G1, the beam combiner 26, and the third lens group G3, and is projected onto a pupil plane of the eye 12 with a predetermined magnification, while being kept as the parallel light, to perform angular scanning with respect to the pupil of the eye 12 as a scanning center. The parallel light is gathered by the eye 12, and, in the fundus oculi of the eye 12, a gathering spot of the SLO light scans the findus oculi, as irradiation light. The irradiation light is reflected from the fundus oculi, and the reflected light sequentially passes through the pupil of the eye 12, the third lens group G3, the beam combiner 26, and the first lens group G1, and is incident on the SLO unit 18 through the first optical scanner 22. An operation after the reflected light is incident on the SLO unit 18 is described above with reference to FIG. 1.

An operation relating to OCT imaging will be described. The parallel OCT light that is incident from the OCT unit 20 into the imaging optical system 19 is angularly scanned by the second optical scanner 22, such as a galvano mirror. The angularly scanned parallel OCT light passes through the second lens group G2, and is reflected from the beam combiner 26, and is thereafter projected through the third lens group G3 onto the pupil plane of the eye 12 with a predetermined magnification, while being kept as the parallel light, to perform angular scanning with respect to the pupil of the eye 12 as the scanning center. The parallel light is gathered by the eye 12, and, in the fundus oculi of the eye 12, a gathering spot of the OCT light scans the fundus oculi (a retina surface) and the inside of the retina, as irradiation light. The OCT light is reflected from the fundus oculi or the inside of the retina, and the reflected light passes through the pupil of the eye 12 and the third lens group G3, and is reflected from the beam combiner 26, and is incident on the OCT unit 20 through the second lens group G2 and the second optical scanner 24. An operation after the reflected light is incident on the OCT unit 20 is described above with reference to FIG. 1. Note that, although the OCT objective lens system 32 is approximately an afocal system, as with as the SLO objective lens system 31, the irradiation light having a relatively large beam diameter, to obtain tomographic information of the findus oculi and the like of the eye 12, is required to be precisely gathered on an observation plane. Therefore, the parallel light beam is required to be appropriately converged or diverged in accordance with variations in length to the observation plane and the dioptric power of the eye 12. However, even in this case, the objective lens system is basically an afocal system.

Figure 3:
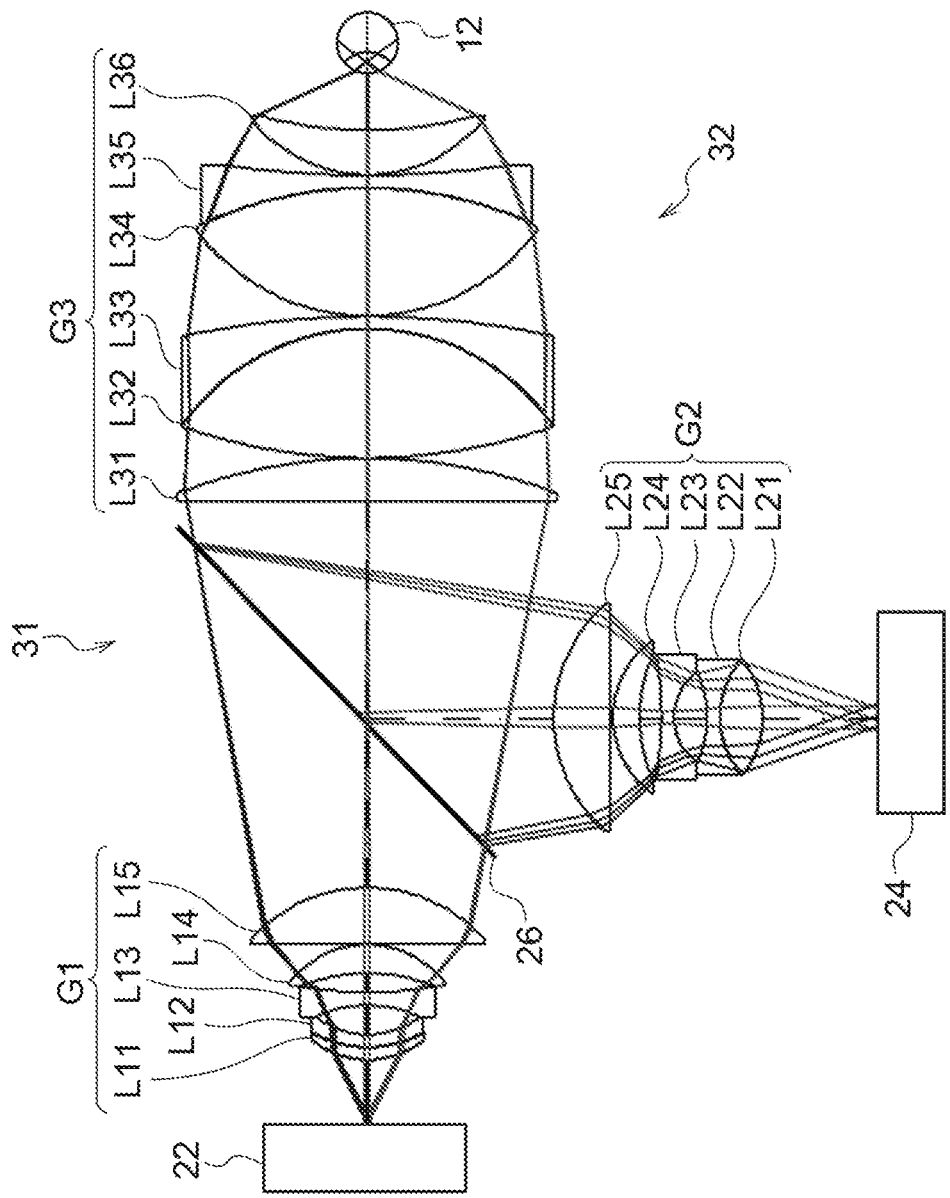
FIG. 3 is a configuration diagram showing an example of a complex objective lens system for SLO and OCT, as the wide angle optical system.

FIG. 3 shows an example of the concrete configuration of the first lens group G1, the second lens group G2, and the third lens group G3. As shown as an example, the first lens group G1 includes, in the following order from the side of the first optical scanner 22 to the side of the eye 12, a meniscus-shaped lens component (a cemented lens of a lens L11 and a lens L12) having a convex surface facing the side of the first optical scanner 22, a negative lens L13 having a concave surface facing the side of the first optical scanner 22, a positive lens L14 having a convex surface facing the side of the eye 12, and a positive lens L15. More specifically, as for the shape of the negative lens L13, the absolute value of the radius of curvature of a lens surface on the side of the first optical scanner 22 is smaller than the absolute value of the radius of curvature of a lens surface on the side of the eye 12. As for the shape of the positive lens L14, the absolute value of the radius of curvature of a lens surface on the side of the eye 12 is smaller than the absolute value of the radius of curvature of a lens surface on the side of the first optical scanner 22. Note that, in this application, "lens component" denotes a lens having two contact interfaces with air on the optical axis, and one lens component denotes one single lens or one cemented lens unit composed of a plurality of lenses cemented together. Using the cemented lens as the meniscus-shaped lens component of the first lens group G, as shown in the drawing, is effective at correcting chromatic aberration, but in a case where used light has a relatively narrow wavelength region, a single lens may be used instead.

By way of example, the second lens group G2 includes, in the following order from the side of the second optical scanner 24 to the side of the eye 12, a meniscus-shaped lens component (a cemented lens of a lens L21 and a lens L22) having a convex surface facing the side of the second optical scanner 24, a negative lens L23 having a concave surface facing the side of the second optical scanner 24, a positive lens L24 having a convex surface facing the side of the eye 12, and a positive lens L25. More specifically, as for the shape of the negative lens L23, the absolute value of the radius of curvature of a lens surface on the side of the second optical scanner 24 is smaller than the absolute value of the radius of curvature of a lens surface on the side of the eye 12. As for the shape of the positive lens L24, the absolute value of the radius of curvature of a lens surface on the side of the eye 12 is smaller than the absolute value of the radius of curvature of a lens surface on the side of the second optical scanner 24. Using the cemented lens as the meniscus-shaped lens component of the second lens group G2, as shown in the drawing, is effective at correcting chromatic aberration, but in a case where used light has a relatively narrow wavelength region, a single lens may be used instead.

The third lens group G3 disposed between the beam combiner 26 and the eye 12 is a common lens group 28 shared between SLO and OCT. By way of example, the third lens group G3 includes, in the following order from the side of the beam combiner 26 to the side of the eye 12, a positive lens L31 having a convex surface facing the side of the eye 12, a lens component in which a positive lens 32 having a convex surface facing the side of the eye 12 and a negative lens L33 are cemented together, a lens component in which a positive lens L34 having a convex surface facing the side of the eye 12 and a negative lens L35 are cemented together, and a positive meniscus lens L36 having a concave surface facing the side of the eye 12. The third lens group G3 includes the two cemented lenses in this example, but may be configured to include only one cemented lens in accordance with a situation of chromatic aberration correction.

In this embodiment, in the configuration having the common lens group 28, the SLO objective lens system 31 and the OCT objective lens system 32 have paraxial angular magnifications set in an appropriate manner. The paraxial angular magnification will be described with reference to FIGS. 4 and 5.

Figure 4:
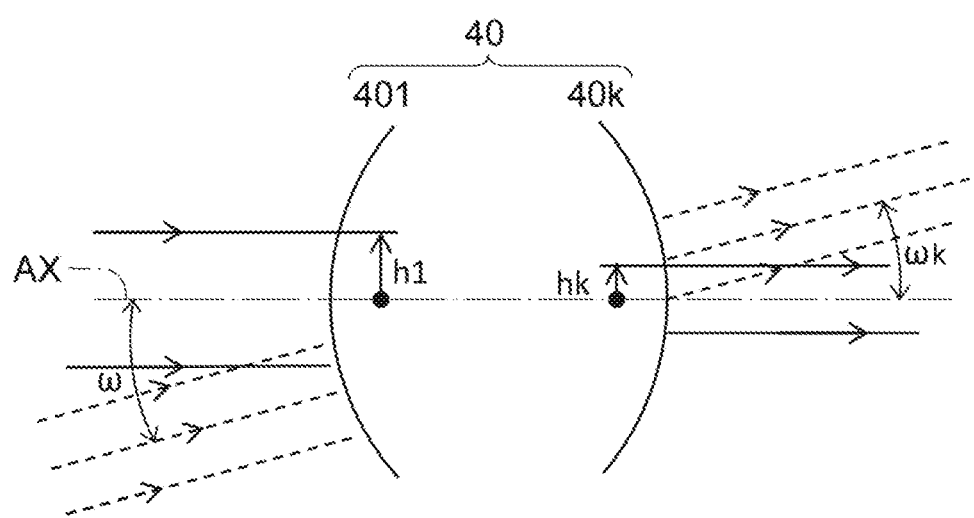
FIG. 4 is a drawing to explain an angular magnification.
Figure 5:
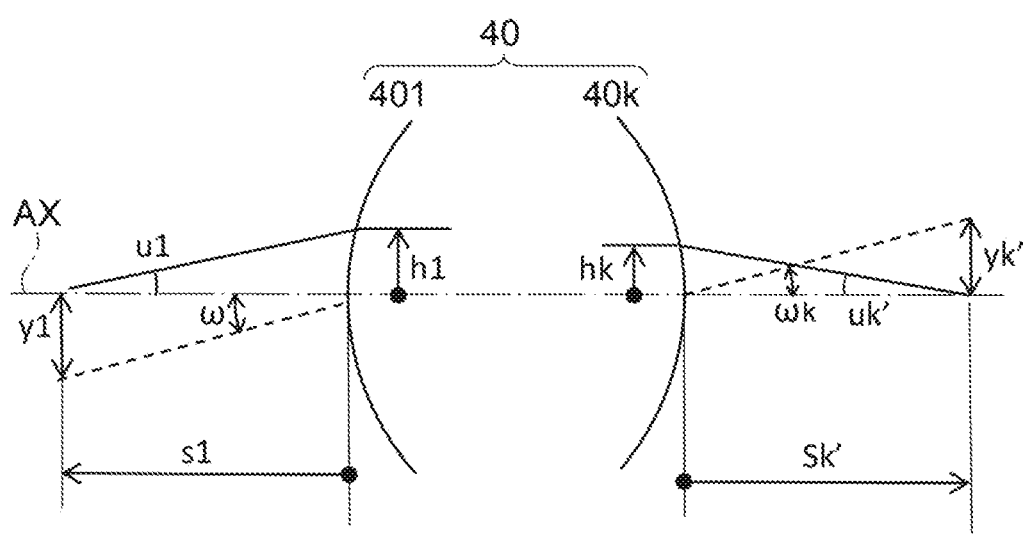
FIG. 5 is a drawing to explain the angular magnification.

FIGS. 4 and 5 show an example of an afocal optical system 40 having a k number of surfaces. In FIGS. 4 and 5, the left side of the drawing corresponds to the side of an object, and the right side corresponds to the side of an image. A parallel light beam incident into the afocal optical system 40 passes through the afocal optical system 40, and exits as a parallel light beam. However, an angle (referred to as an incident angle ω) formed between the incident parallel light beam and an optical axis AX on the side of the object of the afocal optical system 40 is generally different from an angle (referred to as an exit angle ωk) formed between the exit parallel light beam and the optical axis AX on the side of the image of the afocal optical system 40.

As shown in FIG. 5, it is assumed that an arbitrary paraxial ray emitted from an axial object point at a distance of s from a first surface 401 of the afocal optical system 40, which is composed of a k number of surfaces, on the side of the object passes through the afocal optical system 40, and intersects the optical axis at a distance of sk' from a k-th surface 40k, i.e. a last surface, on the side of the image. The paraxial ray is assumed to intersect the first surface 401 and the k-th surface 40k at heights of h1 and hk, respectively, and to form angles of u1 and uk' with the optical axis on the side of the object and the side of the image, respectively, and the size of the object and the size of the image corresponding thereto are assumed to be y1 and yk', respectively. For ease of explanation, the refractive index of a medium anterior and posterior to the afocal optical system is assumed to be 1. According to the Helmholtz-Lagrange invariant.

$$u1 \cdot y1 = uk' \cdot yk'$$

based on u1=h1/s1 and uk'=hk/sk', $$h1 \cdot (y1/s1) = hk \cdot (yk'/sk')$$

here, $$\omega \equiv y1/s1$$

$$\omega k \equiv yk'/sk'$$

in the case of s1→∞, sk'→∞ holds true. At this time, Mpar is defined as follows.

$$Mpar = \omega k/\omega = (h1/hk)_{s1 \to \infty}$$

Mpar is an angular magnification in a paraxial region, i.e. a paraxial angular magnification. As is apparent from the above description, in a case where a paraxial ray parallel with the optical axis is incident on the afocal optical system, the paraxial ray is parallel with the optical axis even after passing through the afocal optical system, and the ration h1/hk between the height of the paraxial ray on the side of the object from the optical axis and the height of the paraxial ray on the side of the image from the optical axis becomes the paraxial angular magnification of the afocal optical system. Namely, the paraxial angular magnification Mpar is an invariable of the optical system that is irrelevant to the incident angle ω. Note that, as is commonly known in an optical field, since a lateral magnification is the reciprocal of the angular magnification, in a case where βpar represents a paraxial lateral magnification, $$\beta par=1/Mpar$$

holds true.

Here, M1 represents the paraxial angular magnification of the optical system that forms a conjugate relationship between the first optical scanner 22 and the pupil of the eye 12, and M2 represents the paraxial angular magnification of the optical system that forms a conjugate relationship between the second optical scanner 24 and the pupil of the eye 12. In the configuration shown in FIG. 2, in a case where M1 represents the paraxial angular magnification of the SLO objective lens system 31 from the first optical scanner 22 toward the eye 12, and M2 represents the paraxial angular magnification of the OCT objective lens system 32 from the second optical scanner 24 toward the eye 12, the following conditional expression (1) is satisfied.

$$|M1|<|M2| \qquad (1)$$

This configuration allows SLO imaging in an ultra-wide-angle field (ultra-wide field, hereinafter abbreviated as UWF), as well as allows OCT imaging in every area in an ultra-wide angle of view. In an example of usage of the ophthalmic device, images of a wide area to the extent of the whole of the imageable area 12A of the eye 12 are captured by SLO imaging by high-speed scanning of the SLO light at 0.5 seconds or less, and thereafter a narrow area, such as a lesion, is imaged by OCT imaging using the OCT light, to obtain information about a tomographic shape. In this usage, while a fast scan speed is required of the first optical scanner 22 for SLO imaging in at least one of X direction scanning and Y direction scanning, a very fast scan speed is not required of the second optical scanner 24 for OCT imaging. Thus, for example, in the concrete, it may be practical that a polygon mirror is used for at least one of the X direction scanning and the Y direction scanning in the first optical scanner 22 for SLO imaging, and a galvano mirror is used in the second optical scanner 24 for OCT imaging. Assuming that θ1 represents a maximum scanning angle at which the first optical scanner 22 for SLO can scan the SLO light using the polygon mirror in a scanning direction, and θ2 represents a maximum scanning angle at which the second optical scanner 24 can scan the OCT light, the maximum scanning angle θ2 of the second optical scanner 24 for OCT is smaller than the maximum scanning angle θ1 of the first optical scanner 22 for SLO, in other words, θ2<θ1 holds true under the circumstances described above. Thus, the scanning angle range of the second optical scanner 24 is smaller than the scanning angle range of the first optical scanner 22.

On the other hand, as for an imageable area, although a narrow area is imaged by OCT imaging, where a lesion or the like occurs cannot be specific, so any portion of an area imaged by SLO imaging is desired to be imaged by OCT imaging. Namely, an area that can be imaged by OCT imaging is desired to be the same as an area that can be imaged by SLO imaging. In other words, in a case where Θ1 represents an external irradiation angle usable in SLO imaging, and Θ2 represents an external irradiation angle usable in OCT imaging, it is desired that Θ1=Θ2 holds true.

By satisfying the above conditional expression (1), Θ1=Θ2 can hold true, even in the case of θ2<θ1, using the scanners having different scanning angles between SLO imaging and OCT imaging.

To be more specific, the paraxial angular magnification M1 of the SLO objective lens system 31 is preferably set in a range that satisfies the following conditional expression (2). The paraxial angular magnification M2 of the OCT objective lens system 32 is preferably set in a range that satisfies the following conditional expression (3).

$$1.5<|M1|<3.5 \qquad (2)$$

$$2.5<|M2|<5 \qquad (3)$$

A configuration satisfying the conditional expressions (2) and (3) is effective, in a case where the external irradiation angle is a wide angle of 100 degrees or more. The configuration satisfying the conditional expressions (2) and (3) is more effective, in the case of requiring an internal irradiation angle of the order of 180 degrees or more in light beam scanning at an ultra-wide-angle, which is referred to as UWF, having an external irradiation angle of more than 120 degrees.

As described above, since the paraxial lateral magnification is the reciprocal of the paraxial angular magnification, in a case where β1 represents the paraxial lateral magnification of the SLO objective lens system 31 from the first optical scanner 22 to the eye 12, and β2 represents the paraxial lateral magnification of the OCT objective lens system 32 from the second optical scanner 24 to the eye 12, the following conditional expression (4) is satisfied. Note that, β1 described here is the paraxial lateral magnification of the SLO objective lens system 31 in a case where the scanning center of the first optical scanner 22 is an object point, and the pupil position of the eye 12 is an image point, and β2 is the paraxial lateral magnification of the OCT objective lens system 32 in a case where the scanning center of the second optical scanner 24 is an object point, and the pupil position of the eye 12 is an image point.

$$|\beta 2|<|\beta 1| \qquad (4)$$

The paraxial lateral magnification can be interpreted as the ratio between the diameter of an incident light beam and the diameter of an exit light beam, in a case where a parallel light beam that is in parallel with an optical axis is incident on an objective lens system and exits therefrom. In a case where the SLO light parallel with the optical axis and the parallel light beam of the OCT light are incident on the objective lens systems, the following expressions hold true:

$$\beta 1=+\phi out(SLO)/\phi in(SLO)$$

$$\beta 2=\phi out(OCT)/\phi in(OCT)$$

where, φin(SLO) represents the diameter of an incident light beam of the SLO light, and φout(SLO) represents the diameter of an exit light beam thereof, and similarly, φin(OCT) represents the diameter of an incident light beam of the OCT light, and φout(OCT) represents the diameter of an exit light beam thereof. Therefore, it is apparent from the conditional expression (4) that, in a case where a parallel light beam that is in parallel with an optical axis is incident on an objective lens system, the diameter of the light beam is less varied in the OCT objective lens system 32 than in the SLO objective lens system 31.

More specifically, β1 is preferably set in a range that satisfies the following conditional expression (5). β2 is preferably set in a range that satisfies the following conditional expression (6).

$$0.25<|\beta 1|<0.7 \qquad (5)$$

$$0.2<|\beta 2|<0.4 \qquad (6)$$

A configuration satisfying the conditional expressions (5) and (6) is effective, in a case where the external irradiation angle is a wide angle of 100 degrees or more. The configuration satisfying the conditional expressions (5) and (6) is more effective, in the case of requiring an internal irradiation angle of the order of 180 degrees or more in light beam scanning at an ultra-wide-angle, which is referred to as UWF, having an external irradiation angle of more than 120 degrees. Note that, the conditional expression (5) more preferably has a lower limit of 0.28, and an upper limit of 0.67.

Note that, in general usage of the ophthalmic device described above, in initial SLO imaging, high-speed scanning of the polygon mirror or the like is required in at least one of the X direction scanning and the Y direction scanning. In OCT imaging, on the contrary, a scanning area is relatively narrow, and a very fast scan speed, to the extent of being required of SLO imaging, is not required. Therefore, in at least one of the X direction scanning and the Y direction scanning, a scan speed at which the second optical scanner 24 scans the OCT light is configured to be slower than a scan speed at which the first optical scanner 22 scans the SLO light. Note that, the scan speed described here denotes a scan time per unit area. Scanning the entirety of an ultra-wide-angle fundus imaging area, i.e. UWF, at high speed is required of SLO imaging, the maximum scanning angle of the first optical scanner 22 for SLO is determined in accordance with the fundus imaging area. On the other hand, a limited partial area that requires tomographic imaging is scanned in OCT imaging, but the maximum scanning angle of the second optical scanner 24 for OCT is preferably configured based on the relationship of the above conditional expressions, such that an entire ultra-wide-angle fundus area, which is similar to the imaging area of SLO imaging, can be imaged on a partial area basis.

The imaging optical system 19 having scan speeds set as described above is preferably configured to satisfy the above conditional expression (1). The imaging optical system 19 is preferably configured to satisfy at least one of the conditional expressions (2) and (3). In the same manner, the imaging optical system 19 having scan speeds set as described above is preferably configured to satisfy the above conditional expression (4). The imaging optical system 19 is preferably configured to satisfy at least one of the conditional expressions (5) and (6).

A configuration related to the above conditional expressions (2), (3), (5), and (6) is not limited to a case in which the wide angle optical system 30 has the complex objective lens system for SLO and OCT, but is effective in a case where the SLO objective lens system 31 and the OCT objective lens system 32 are configured separately. Thus, according to the conditions indicated by the conditional expressions (2) and (3) described above, the paraxial angular magnification of the UWF objective lens is preferably larger than 1.5, and is larger than 1.8 to be advantageous in terms of practical use.

In the above configuration, the third lens group G3, which is the common lens group 28, mainly corrects a pupil aberration, as a fundamental function of an SLO objective lens and an OCT objective lens, in order to form a substantial afocal system in which the pupil of the eye 12 and the scanner have a conjugate relationship. The first lens group G1 has, by the combined use with the third lens group G3, the function of ensuring the above-described magnification relationships required of the SLO objective lens system 31, and the function of correcting a chromatic aberration. The second lens group G2 has, by the combined use with the third lens group G3, the function of ensuring the above-described magnification relationships required of the OCT objective lens system 32, and the function of correcting a chromatic aberration. This lens configuration is suitable for an ultra-wide-angle objective lens system having an external irradiation angle of more than 120 degrees, but in the case of a narrow angle of view, the configuration of each lens may be more simplified, as a matter of course.

Figure 6A:
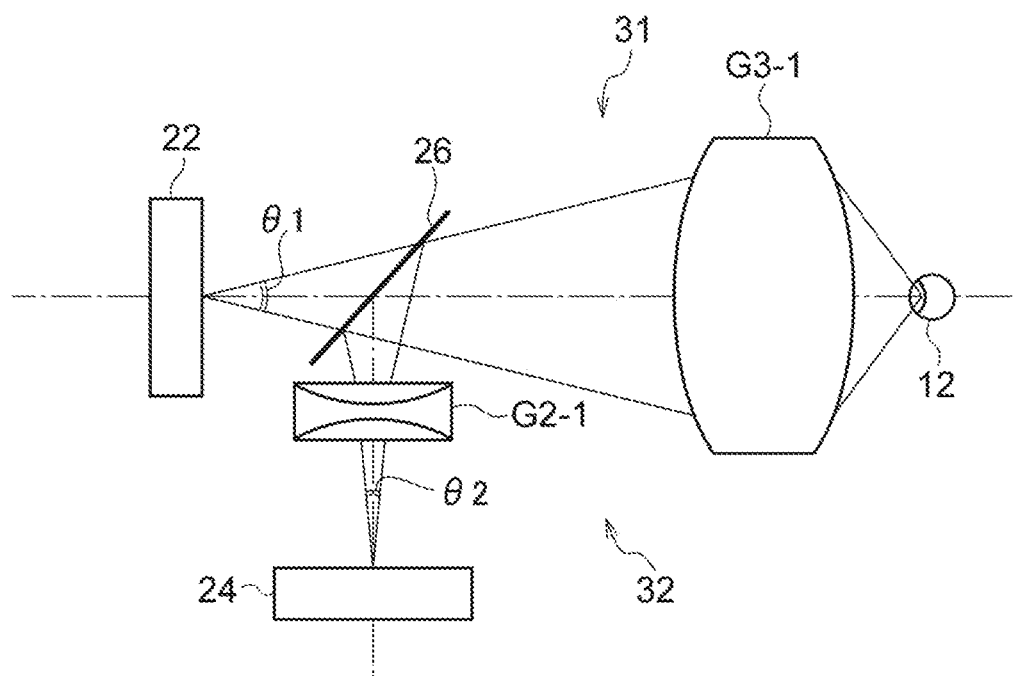
FIG. 6A is a schematic diagram showing the configuration of a modification example of the complex objective lens system.

Note that, in the configuration of FIG. 2, both of the SLO objective lens system 31 and the OCT objective lens system 32 have the lens groups on the sides of the scanners (i.e. on the side of the light sources) relative to the beam combiner 26, but, by appropriately designing the common lens group 28, any one of the SLO objective lens system 31 and the OCT objective lens system 32 may be configured not to have a lens group on the side of the light source, i.e. on the side of the scanner, relative to the beam combiner 26. FIGS. 6A and 6B are schematic diagrams of a first modification example and a second modification example of the complex objective lens system, respectively.

In the configuration shown in FIG. 6A, as compared to the configuration of FIG. 2, no lens group is disposed between the first optical scanner 22 for SLO and the beam combiner 26, and the third lens group G3 of FIG. 2 is substituted with a third lens group G3-1, and the second lens group G2 of FIG. 2 is substituted with a second lens group G2-1. In the configuration of FIG. 6A, the third lens group G3-1 corresponds to the common lens group 28, and the SLO objective lens system 31 is constituted of only the third lens group G3-1, while the OCT objective lens system 32 is constituted of the second lens group G2-1 and the third lens group G3-1. In this configuration, the third lens group G3-1 corrects an aberration in the visible light region for SLO. The second lens group G2-1 of the OCT objective lens system 32 is required to have such a lens configuration as to correct an aberration in the infrared region for OCT, in the composite system with the third lens group G3-1, and is preferably configured to basically have a negative refractive power. Considering the circumstances described above even in this modification example, the maximum scanning angle θ2 of the second optical scanner 24 for OCT is smaller than the maximum scanning angle θ1 of the first optical scanner 22 for SLO, in other words, θ2<θ1 holds true.

In the configuration shown in FIG. 6B, as compared to the configuration of FIG. 2, no lens group is disposed between the second optical scanner 24 and the beam combiner 26, and the third lens group G3 of FIG. 2 is substituted with a third lens group G3-2, and the first lens group G1 of FIG. 2 is substituted with a first lens group G-1. In the configuration of FIG. 6B, the third lens group G3-2 corresponds to the common lens group 28, and the SLO objective lens system 31 is constituted of the first lens group G1-1 and the third lens group G3-2, while the OCT objective lens system 32 is constituted of only the third lens group G3-2. In this configuration, the third lens group G3-2 corrects an aberration in the infrared region for OCT. The first lens group G1-1 of the SLO objective lens system 31 for SLO is required to have such a lens configuration as to connect an aberration in the visible light region for SLO, in the composite system with the third lens group G3-2, and is preferably configured to basically have a positive refractive power. Considering the circumstances described above even in this modification example, the maximum scanning angle θ2 of the second optical scanner 24 for OCT is smaller than the maximum scanning angle θ1 of the first optical scanner 22 for SLO, in other words, θ2<θ1 holds true.

Note that, the forms of optical paths shown in FIGS. 2, 6A, and 6B are just examples. The technology of the present disclosure may adopt optical paths of other forms. For example, by appropriately setting the wavelength characteristics of the beam combiner 26, the SLO objective lens system 31 may have a bent optical path, while the OCT objective lens system 32 may have a straight optical path.

<SLO or OCT Objective Lens System>

Next, an objective lens system used in the imaging optical system 19 will be described. Note that, the following embodiment is not limited to a case in which the wide angle optical system 30 has the complex objective lens system shown in FIGS. 2, 6A, and 6B, but may be applied to a case in which the SLO objective lens system 31 and the OCT objective lens system 32 are configured separately. Note that, in the following description, for the sake of convenience of the description, in a case where the SLO objective lens system 31 and the OCT objective lens system 32 are not required to be distinguished in the description, the SLO objective lens system 31 and the OCT objective lens system 32 are simply referred to as "objective lens system". In a case where the first optical scanner 22 and the second optical scanner 24 are not required to be distinguished in the description, the first optical scanner 22 and the second optical scanner 24 are simply referred to as "scanner".

The SLO objective lens system and the OCT objective lens system having the above-described common lens group 28 are independently designed. In the following embodiment, in each of the SLO objective lens system 31 and the OCT objective lens system 32, the angular distribution of the angular magnification is appropriately designed. The angular distribution of the angular magnification will be described.

By way of example, FIG. 7 is a drawing of an objective lens system 300. The objective lens system 300 is a refractive optical system including eleven lenses L1 to L11. The objective lens system 300 is basically an afocal optical system. FIG. 7 also shows a scanning center position Ps in which one reflective plane included in a scanner is situated, and a pupil plane Pp of an eye 12. The objective lens system 300 is configured such that the scanning center position Ps of the scanner and the position of the pupil plane Pp have a conjugate relationship. A light beam incident from the scanner on the objective lens system 300 is approximately parallel light. FIG. 7 shows a state of a light beam that is scanned by the scanner and incident on the pupil plane Pp through the objective lens system 300 at a maximum angle of view.

As shown in FIG. 7, ωin represents an angle formed between an incident light ray 44i from the side of the scanner into the objective lens system 300 and an optical axis AX of the objective lens system 300, and ωout represents an angle formed between an exit light ray 44o from the objective lens system 300 to the side of the eye 12 and the optical axis AX. M is defined as M=|ωout/ωin|. The following conditional expression (7) is satisfied:

$$Mpar < Mmax \quad (7)$$

where, Mpar represents M in a case that the incident light ray 44i is a paraxial ray, and Mmax represents M in a case that the incident light ray 44i is a ray at a maximum angle of view.

The conditional expression (7) denotes that M of the light ray at the maximum angle of view is larger than the angular magnification in a paraxial region. By satisfying the conditional expression (7), it becomes easy to have an aberration configuration in which the angular distribution of the angular magnification increases in conjunction with an increase in an exit angle of a peripheral light ray. According to the configuration having such a distribution of the angular magnification, the maximum scanning angle of the scanner becomes larger, and the objective lens system easily has a larger external irradiation angle, and therefore the imaging optical system 19 has such a viewing angle in the findus oculi that can observe a wide fundus area from the center of a fundus oculi to the periphery of the findus oculi.

Furthermore, the following conditional expression (8) is preferably satisfied.

$$1.1 \times Mpar < Mmax \quad (8)$$

ωout is the angle of a light ray that is incident from the objective lens system 300 on the eye 12. By satisfying the conditional expression (8), the angle ωout of the incident light ray from the objective lens system 300 into the eye 12 can be efficiently increased, thus facilitating having a large external irradiation angle.

The following conditional expression (9) is preferably satisfied.

$$Mmax < 2 \times Mpar \quad (9)$$

By satisfying the conditional expression (9), the difference between resolution of the ophthalmic device having a small ωin and resolution of the ophthalmic device having a maximum ωin is easily confined within an allowable range. Note that, as the configuration of the ophthalmic device for UWF, the conditional expressions (8) and (9) are preferably satisfied at the same time.

The following conditional expressions (10) and (11) are preferably satisfied.

$$1 < Mpar \quad (10)$$

$$1 < Mmax \quad (11)$$

Satisfying the conditional expressions (10) and (11) facilitates having a large external irradiation angle. Furthermore, Mmax more preferably satisfies the following conditional expression (11A). Even more preferably, the lower limit value and the upper limit value of the conditional expression (11A) are respectively set to be 2.5 and 3.

$$2 < Mmax < 5 \quad (11A)$$

Considering the above conditional expression (7) from the viewpoint of an area of the eye 12 to be scanned, in a case where Mc represents M at a central area containing an intersection of the eye 12 and the optical axis AX, and Mp represents M at a peripheral area of the eye 12, the following conditional expression (7A) is preferably satisfied.

$$Mc < Mp \quad (7A)$$

Mpar and Mc are approximate values. When a light ray at a maximum angle of view reaches the peripheral area of the eye 12, Mmax and Mp become the same value. Satisfying the conditional expression (7A) provides the same effects as those in the case of satisfying the conditional expression (7).

Figure 8:
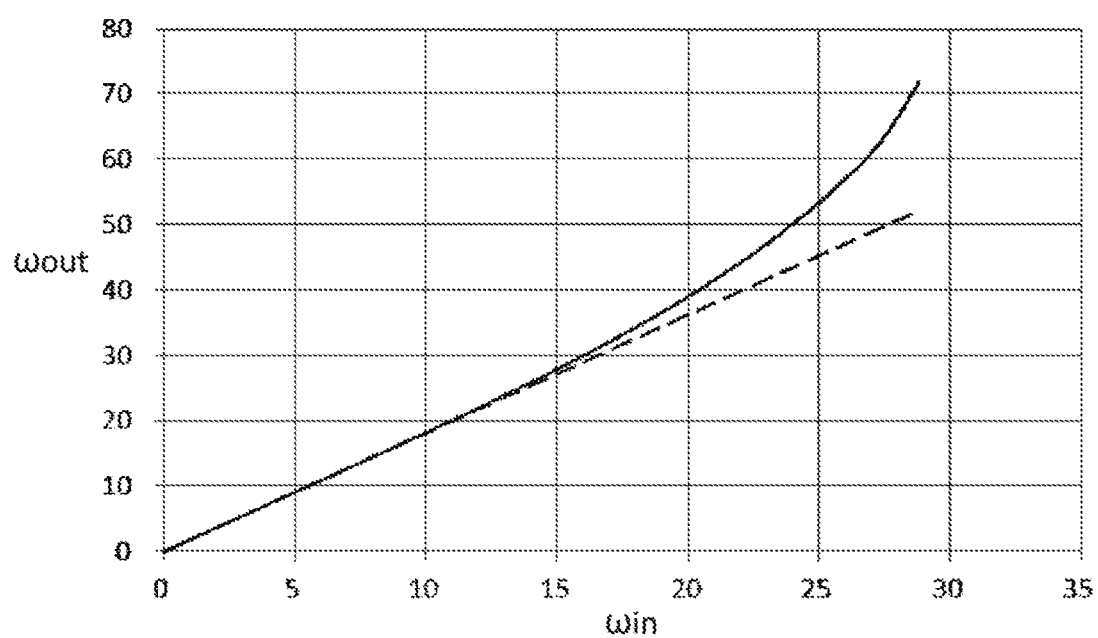
FIG. 8 is a graph showing an example of the relationship between ωin and ωout in the objective lens system.

In FIG. 8, a solid line represents an example of the relationship between ωin and ωout in an objective lens system according to an example of this embodiment. In the graph of FIG. 8, a horizontal axis represents ωin, and a vertical axis represents wont. Although a galvano mirror or a polygon mirror is used as a scanner, there is a demand for maximizing ωout, while keeping ωin at the smallest possible value, in order to prevent increases in the size and cost of a device. Therefore, in this example, the ratio M between ωin and ωout is inconstant. Note that, for the sake of comparison, in FIG. 8, a broken line represents the relationship between ωin and ωout in a comparative example in which M is a constant value at any angle of view. Although the value of M depicts a straight line in the comparative example, the exit angle ωout sharply increases in conjunction with an increase in the incident angle ωin in the example of this embodiment.

Figure 9:
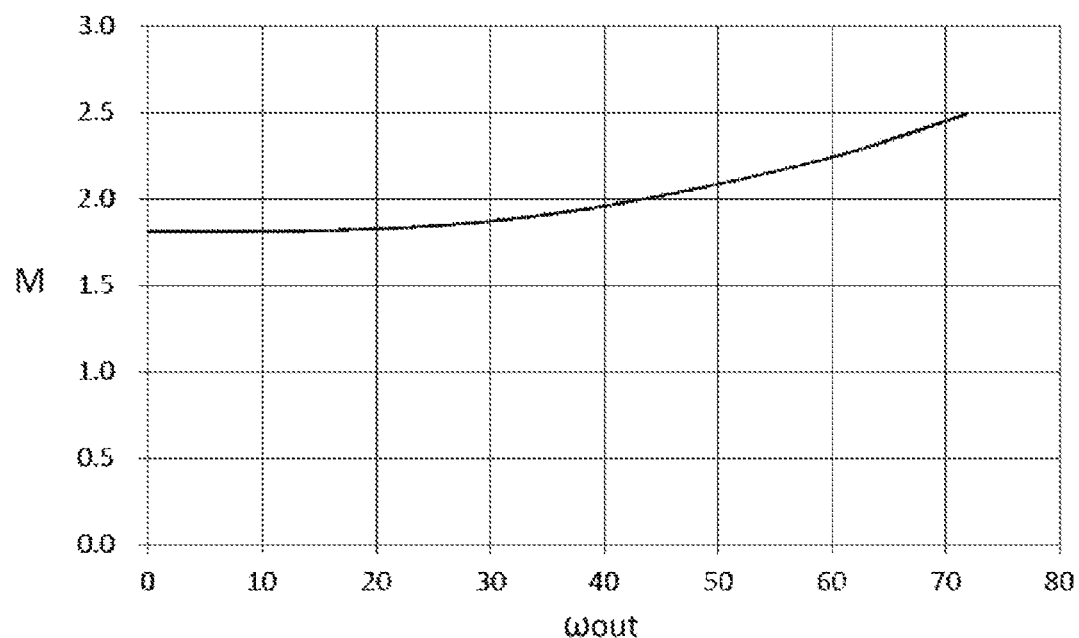
FIG. 9 is a graph showing an example of the relationship between ωout and M in the objective lens system.

The graph of FIG. 9 shows an example of the relationship between ωout and M in the objective lens system according to the example of this embodiment. In FIG. 9, a horizontal axis represents ωout, and a vertical axis represents M. The example shown in FIGS. 8 and 9 satisfies the above conditional expressions (7) to (11). In the example, a range between Mpar and Mmax includes a range within which M increases in conjunction with an increase in ωin. Note that, M preferably increases in conjunction with an increase in ωin within an entire range between Mpar and Mmax.

The above-described angular distribution of the angular magnification is suitable for an objective lens system that maintains an external irradiation angle of the order of 100 degrees or more, as well as the objective lens system shown in FIG. 7. As described above in relation to the conditions indicated by the conditional expressions (2) and (3), the paraxial angular magnification of the UWF objective lens is preferably larger than 1.5. Furthermore, the conditional expression 1.5<Mpar<5.0 related to the paraxial angular magnification Mpar preferably holds true. The lower limit value of the paraxial angular magnification is advantageously larger than 1.8 in terms of practical use. The upper limit value is advantageously smaller than 4.0 to prevent the scanning angle of the scanning unit as the UWF from being excessively large.

Next, the diameter of a light beam applied from the wide angle optical system 30 to the pupil plane of the eye 12 will be considered. In the ophthalmic device, even if the scanning angle ωin varies, the diameter of the light beam is preferably equal to or lower than a desired value in the pupil plane of the eye 12. If the diameter of the light beam exceeds the desired value, there is a problem that the light beam does not enter the pupil of the eye 12. Since a peripheral light beam, i.e. the light beam having a large ωin passes through peripheral portions of lenses of the objective lens system 300, the peripheral light beam is susceptible to the effect of an aberration of the objective lens system 300, so the light beam likely moves in a meridional direction on the pupil plane of the eye 12 and produces wobbling.

Therefore, in this embodiment, the following conditional expression (12) is satisfied:

$$P\max < P\min \times 0.7 / (\cos(\omega\max)) \quad (12)$$

where, ωmax represents a maximum value of an angle formed between an exit light beam that exits from the objective lens system 300 to the eye 12 and an optical axis AX of the objective lens system 300, Pmax represents the diameter of the exit light beam in the meridional direction at the position of the pupil plane Pp of the eye 12, in a case where the exit light beam forms an angle of ωmax with respect to the optical axis AX, and Pmin represents the diameter of the exit light beam in the meridional direction at the position of the pupil plane Pp of the eye 12, in a case where the exit light beam forms a minimum angle with respect to the optical axis AX.

By satisfying the conditional expression (12), the diameter of the light beam becomes small in the meridional direction on the pupil of the eye 12, thus facilitating entrance of the light beam into the pupil of the eye 12.

Figure 10:
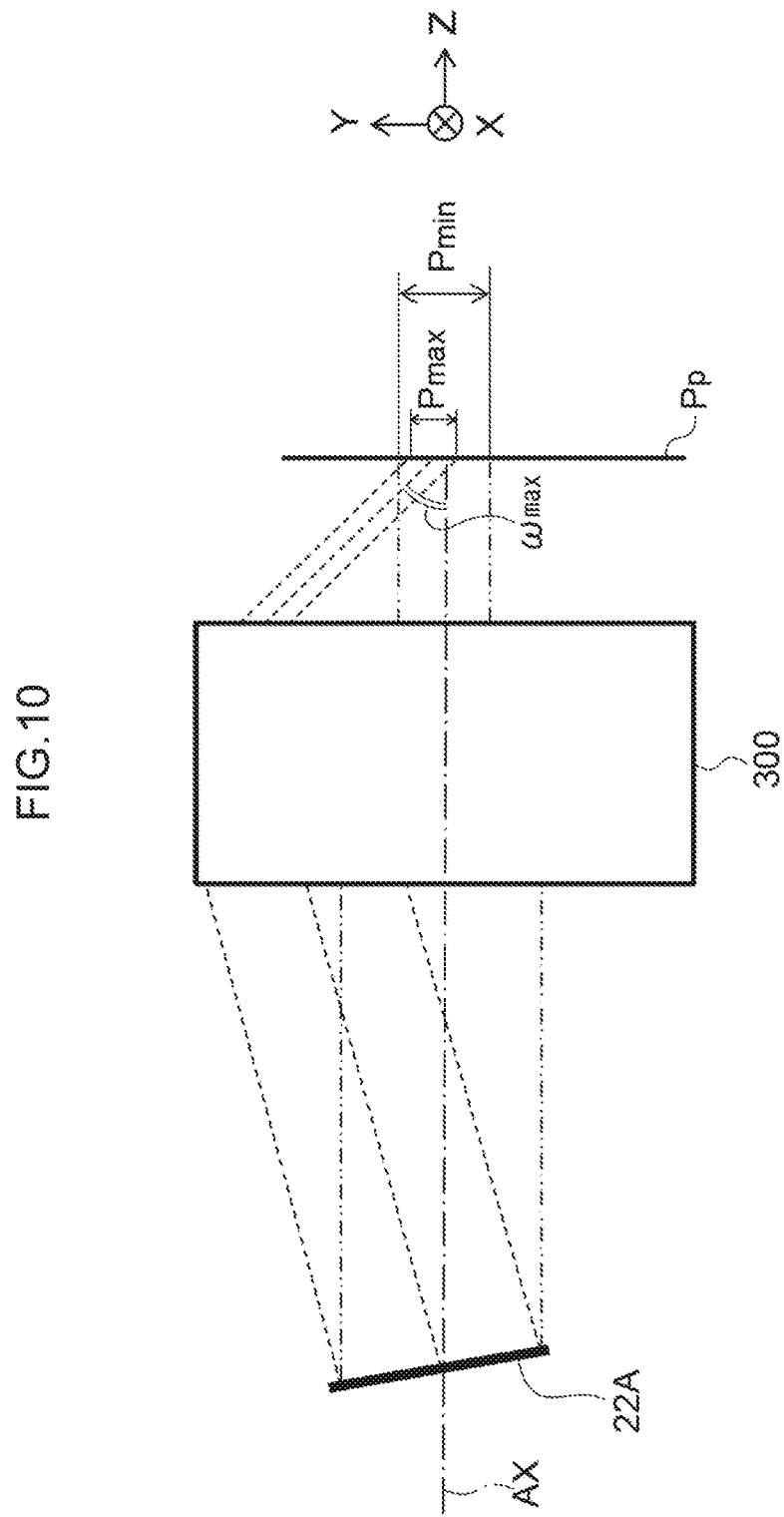
FIG. 10 is a schematic diagram showing a light beam at a maximum angle of view and a paraxial light beam, in which the light beams are incident from a scanner through the objective lens system on a pupil plane of an eye.

FIG. 10 is a schematic diagram of a light beam that exits from a reflective plane 22A of the scanner and is incident on the pupil plane Pp through the objective lens system 300. FIG. 10 shows a YZ plane, and the direction of the optical axis AX corresponds to the Z direction, and the scanning direction by the reflective plane 22A of the scanner corresponds to the Y direction. Namely, in the configuration shown in FIG. 10, the Y direction corresponds to the meridional direction. In FIG. 10, broken lines represent a light beam in a case where the angle formed between the exit light beam and the optical axis AX is a maximum angle ωmax, and chain double-dashed lines represent a light beam in a case where the angle formed between the exit light beam and the optical axis AX is minimum. As described above in the description relating to FIG. 7, the objective lens system 300 is configured such that the scanning center position Ps of the scanner and the position of the pupil plane Pp have an optically conjugate relationship in the paraxial region. In FIG. 7, the pupil position is represented as a plane orthogonal to the optical axis AX, i.e. the position of the pupil plane Pp. Thus, a scanning light beam reflected from the reflective plane 22A arranged on the optical axis AX passes through the objective lens system 300, and intersects the pupil plane Pp. In the configuration of FIG. 10, Pmin corresponds to the diameter of a cross section of a light beam represented by the chain double-dashed lines that is approximately in parallel with the optical axis, in the meridional direction on the pupil plane Pp. Pmax corresponds to the diameter of a cross section of the exit light beam having the maximum angle ωmax from the objective lens system 300, which is represented by the broken lines, in the meridional direction on the pupil plane Pp.

Figure 11:
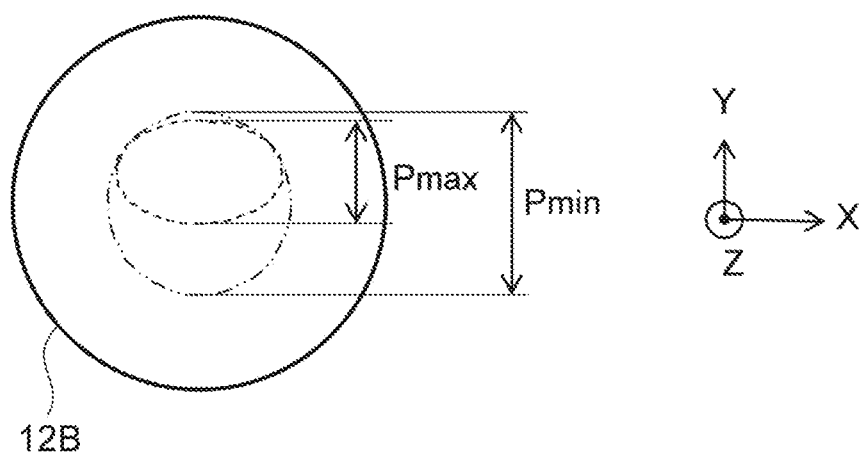
FIG. 11 is a drawing showing an example of the shapes of light beams at a minimum angle and a maximum angle in cross section, in the pupil plane of the eye.

FIG. 11 schematically shows the shapes of the two light beams represented by the broken lines and the chain double-dashed lines, on the pupil plane of the eye 12. FIG. 11 shows an XY plane, and the Y direction coincides with the vertical direction of the drawing. In FIG. 11, a solid line represents the shape of the pupil 12B of the eye 12, a broken line represents the shape of the light beam in a case where the angle formed between the exit light beam and the optical axis AX is the maximum angle ωmax, and a chain double-dashed line represents the shape of the light beam in a case where the angle formed between the exit light beam and the optical axis AX is minimum. While the shape of the light beam represented by the chain double-dashed line is approximately circular, the shape of the light beam represented by the broken line is shrunk in the Y direction, i.e. the meridional direction. Owing to the shape, it becomes easy to apply the exit light beam from the objective lens system 300 to the pupil 12B of the eye 12, even during the occurrence of wobbling. Note that, FIG. 11 is based on the assumption that the light beam is angularly scanned in the Y direction, for the sake of explanation, but an actual light beam is angularly scanned in an XY two-dimensional direction with respect to the axial position of the pupil plane Pp. Therefore, the Y direction shown in FIG. 11 does not always coincide with the scanning direction of the scanner, and the diameter of the light beam is a diameter in the meridional direction.

To apply the light beam to the pupil 12B of the eye 12 with high efficiency, the following conditional expression (13) is preferably satisfied.

$$P\max < P\min \quad (13)$$

If the conditional expression (13) is not satisfied, it is required, in designing and manufacturing, to manage the position of the light beam in a case where the angle formed between the exit light beam and the optical axis AX is ωmax, on the pupil, thus increasing the degree of difficulty in manufacturing.

The following conditional expression (14) is preferably satisfied.

$$0.2 \times P\min < P\max \quad (14)$$

If the conditional expression (14) is not satisfied, variations in the diameter of the light beam become too conspicuous on the retina. The configuration of the ophthalmic device preferably satisfies the conditional expressions (13) and (14) at the same time.

Figure 12:
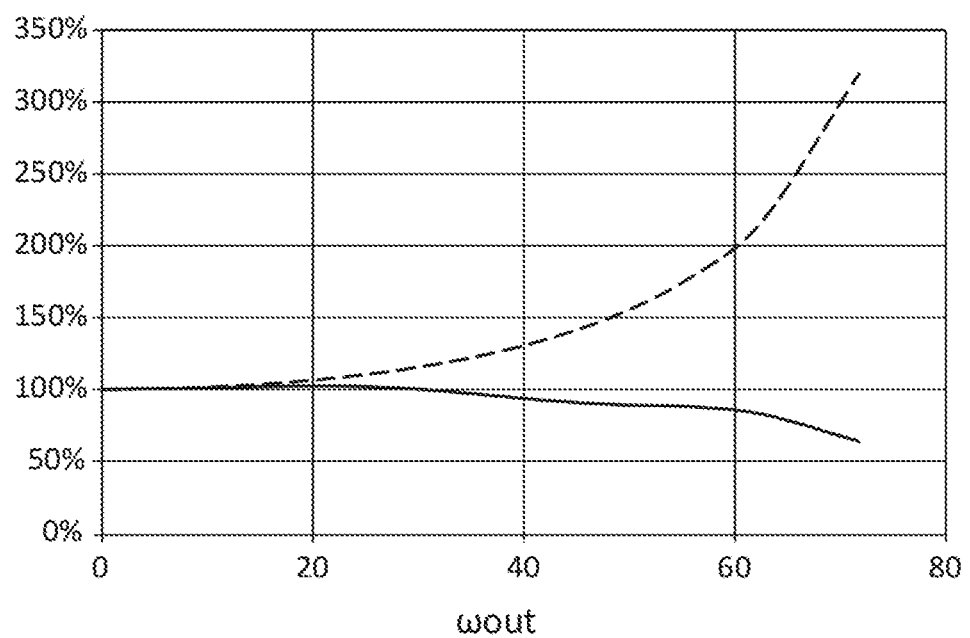
FIG. 12 is a graph showing an example of the relationship between wont and Pmax/Pmin in the objective lens system.

In FIG. 12, a solid line represents the relationship between ωout and Pmax/Pmin in the objective lens system according to the example of this embodiment. In FIG. 12, a horizontal axis represents the angle ωout that a light beam incident on the pupil plane Pp through the objective lens system forms with the optical axis AX, and a vertical axis represents Pmax/Pmin. In a system that does not consider the diameter of a light beam, in contrast to this embodiment, the diameter of the light beam in the meridional direction on the pupil 12B of the eye 12 has a relationship of 1/cos(ωout). In FIG. 12, a broken line represents the characteristic of the system that does not consider the diameter of the light beam, as a comparative example.

As shown in FIG. 12 as an example, in a case where ωout is a maximum angle of 72 degrees, Pmax/Pmin is 320% in the comparative example represented by the broken line. On the contrary, in this embodiment represented by the solid line, the objective lens system is appropriately designed so as to make Pmax/Pmin 1 or less, and specifically approximately 64%.

Next, a configuration of an objective lens system according to the present embodiment will be described with reference to FIG. 13. The concept of the expression " consisting of " in the description on the configuration of the lens system in this specification, is applied only to the lenses as the components, meaning that the concept does not apply to elements other than lenses (such as an optical member such as a filter or a prism having no refractive power and aperture stop for example). Thus, the expression "the objective lens system consists of a front group and a rear group" indicates that the objective lens system only includes the front group and the rear group as the lens groups, but that the objective lens system may further include the elements other than lenses.

Figure 13:
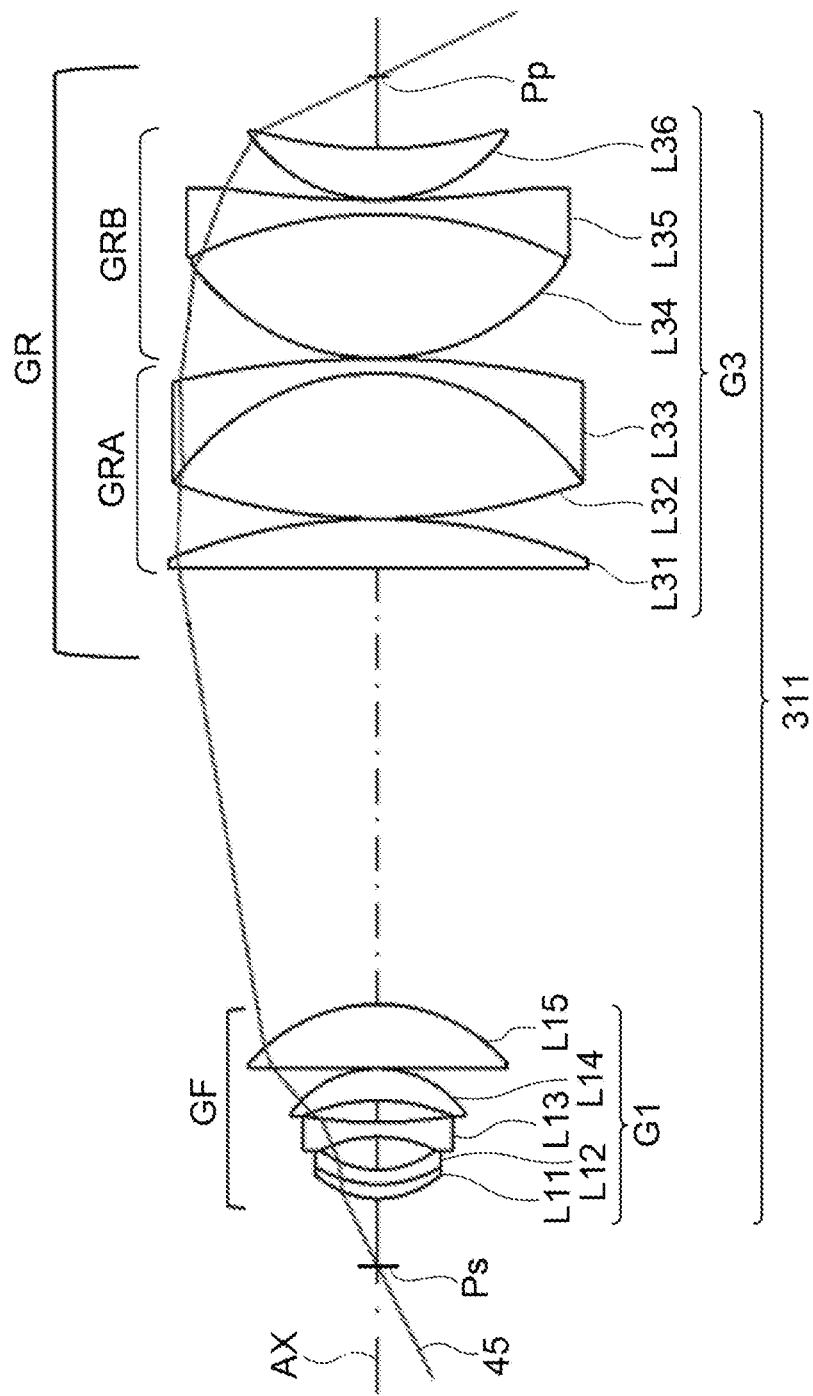
FIG. 13 is a drawing showing the configuration of an objective lens system according to a practical example 1-1.

FIG. 13 is a diagram showing a configuration of an objective lens system according to the present embodiment, and also showing a configuration according to practical example 1-1 described later. Here, an overall configuration and a group configuration are mainly described. A detailed configuration of each lens will be described in the section of practical examples described later. An objective lens system 311 shown in FIG. 13 includes, in the following order from the side of the scanner, a first lens group G1 and a third lens group G3. The first lens group G1 and the third lens group G3 are separated by a maximum air gap in the objective lens system 311. The third lens group G3 is an example of the common lens group 28. The maximum air gap is suitable for disposing a beam combiner 26, e.g. a dichroic mirror or the like, having light combining and separating functions, thus allowing configuring a complex objective lens system for SLO and OCT.

By separating the groups with the above maximum air gap, it can be regarded that the objective lens system 311 consists of a front group GF having positive refractive power and a rear group GR having positive refractive power and being disposed on the side of the eye of the front group GF, with the front group GF and the rear group GR being separated from each other by the maximum air gap on the optical axis between the lens surfaces in the objective lens system 311. In the example shown in FIG. 13, the first lens group G1 corresponds to the front group GF and the third lens group G3 corresponds to the rear group GR. In the example of the OCT objective lens system 32 constituted of the second lens group G2 and the third lens group G3 as shown in FIG. 3, the second lens group G2 corresponds to the front group GF and the third lens group G3 corresponds to the rear group GR. Note that when there are two or more maximum air gaps on the optical axis between lens surfaces in the objective lens system 311, the front group GF and the rear group GR are assumed to be the lens groups separated from each other by the nearest maximum air gap to the eye.

The front group GF has a function of converting an inclination angle of an incident light ray from the side of the light source into a small angle and transmitting the light ray to the rear group GR. As shown in FIG. 13, a light ray 45 at a maximum angle of view has a smaller angle, relative to the optical axis AX, when exiting from the front group GF than the angle thereof at the time of entrance to the front group GF. On the other hand, the angle of the light ray exiting from the rear group GR toward the eye, relative to the optical axis AX is extremely large. Thus, a configuration suitable as the UWF objective lens is obtained.

The objective lens system according to the present embodiment suitable to be an optical system for guiding light from the light source toward the eye as described above is configured to satisfy the following conditional expression (15), where TL represents a geometrical distance, on the optical axis, between the nearest lens surface to the light source in the objective lens system and the nearest lens surface to the eye in the objective lens system, and f represents the focal length of the objective lens system. Note that TL is equivalent to what is called a lens total length. The conditional expression (15) is one condition satisfied by the objective lens system as an afocal optical system. With the condition of the afocal optical system satisfied, an approximately parallel light beam can be made incident on the eye. Accordingly, the eye can be favorably observed with an effect of individual difference such as a shape and a size of the eye suppressed.

$$-1 < TL/f < 1 \tag{15}$$

Furthermore, the objective lens system according to the present embodiment preferably satisfies, as the UWF objective lens, the following conditional expression (16), where fF represents the focal length of the front group GF and fR represents the focal length of the rear group GR.

$$1 < fF/fR < 4 \tag{16}$$

When the light ray between the front group GF and the rear group GR is approximately parallel to the optical axis AX, fF/fR is substantially equivalent to the paraxial angular magnification Mpar. With the above described conditional expression related to Mmax as well as conditional expression (16) satisfied, a large external irradiation angle can be obtained. The UWF objective lens more preferably has fF/R larger than 1.5.

The objective lens system according to the present embodiment preferably satisfies the following conditional expression (17), where D represents the maximum air gap by which the front group GF and the rear group GR are separated from each other on the optical axis, and TL represents a geometrical distance, on the optical axis, between the nearest lens surface to the light source in the objective lens system and the nearest lens surface to the eye in the objective lens system.

$$0.1 < D/TL < 0.5 \tag{17}$$

If the lower limit of the conditional expression (17) is not satisfied a lens density within a predetermined lens total length is high, resulting in a heavy weight. If the upper limit of the conditional expression (17) is not satisfied, lens components required for aberration correction cannot be provided within a predetermined lens total length.

More specifically, the rear group GR consists of an A group GRA having positive refractive power and a B group GRB having positive refractive power and being disposed on the side of the eye of the A group GRA. The A group GRA includes at least one cemented lens having positive refractive power as whole, and the lens surface on the side of the eye of the nearest lens to the eye in the A group GRA is a convex surface or a flat surface. The B group GRB consists of one or a plurality of positive meniscus-shaped lens components having a concave surface facing the side of the eye. With the B group GRB having such a configuration, the light ray aberration can be favorably corrected.

The following conditional expression (18) is preferably satisfied where fB represents the focal length of the B group GRB, and fR represents the focal length of the rear group GR.

$$0.4 < fB/fR < 2.5 \quad (18)$$

If the lower limit of the conditional expression (18) is not satisfied, the chromatic aberration and the high-order aberration are difficult to correct. If the upper limit of the conditional expression (18) is not satisfied, the lens system as a whole is large and heavy. The lower limit value and the upper limit value of the conditional expression (18) are more preferably 0.5 and 1.75 respectively, and are even more preferably 0.8 and 1.1 respectively.

All the positive lenses in all the cemented lenses in the A group GRA preferably satisfy the following conditional expression (19), where fAp represents the focal length of a positive lens constituting a cemented lens in the A group GRA, and fR represents the focal length of the rear group GR.

$$0.9 < fAp/fR < 3.7 \quad (19)$$

If the lower limit of the conditional expression (19) is not satisfied, the volume of the glass material is large, resulting in a high cost and heavy weight. If the upper limit of the conditional expression (19) is not satisfied, the chromatic aberration cannot be sufficiently corrected. The lower limit value and the upper limit value of the conditional expression (19) are more preferably 1.7 and 3 respectively.

The front group GF preferably has a lens surface of negative refractive power and a lens surface of positive refractive power disposed on the side of the eye of this lens surface. With this configuration, high-order light ray aberration on the wide angle of view side, that is, the curvature of field and comma aberration in particular can be more favorably corrected.

For example, when the front group GF has a positive meniscus lens having a convex surface facing the side of the eye, a concave surface of this positive meniscus lens facing the side of the scanner is the lens surface having the negative refractive power, and the convex surface of this positive meniscus lens facing the side of the eye is the lens surface having the positive refractive power. Thus, the high-order light ray aberration on the wide angle of view side can be corrected.

When the front group GF has a meniscus lens having a convex surface facing the side of the scanner, the front group GF preferably further has a negative lens and a positive lens on the side of the eye of this meniscus lens. With this configuration, correction of the lateral chromatic aberration can be achieved depending on the glass material selected, in addition to the effect of correcting the high-order light ray aberration on the wide angle of view side. When the lateral chromatic aberration needs not to be corrected, the high-order light ray aberration of the wide angle of view can be more accurately corrected.

Furthermore, the front group GF preferably includes a negative lens and a positive lens disposed on the side of the eye of this negative lens, and has an air lens having negative refractive power formed between these negative and positive lenses. With this configuration, high-order light ray aberration on the wide angle of view side, that is, the curvature of field and comma aberration in particular can be corrected. In the configuration in which the air lens is formed as described above, the negative lens and the positive lens are preferably arranged to have their concave surfaces facing each other. With this configuration, high-order light ray aberration on the wide angle of view side, that is, the curvature of field and comma aberration in particular can be corrected. In the configuration in which the air lens is formed as described above, a meniscus lens having a concave surface facing the side of the eye is preferably further provided on the side of the scanner of the negative lens defining the air lens, and a positive lens is preferably further provided on the side of the eye of the positive lens defining the air lens. With this configuration, correction of the lateral chromatic aberration can be achieved depending on the glass material selected, in addition to the effect of correcting the high-order light ray aberration on the wide angle of view side. When the lateral chromatic aberration needs not to be corrected, the high-order light ray aberration of the wide angle of view can be more accurately corrected.

The A group GRA of the rear group GR preferably includes one or more cemented lenses. With this configuration, axial chromatic aberration and pupil chromatic aberration can be corrected. The A group GRA preferably includes two or more cemented lenses. With this configuration, axial chromatic aberration and pupil chromatic aberration can be corrected more accurately.

The B group GRB of the rear group GR preferably includes one or more positive meniscus-shaped single lenses. Such a lens enables aplanatic reception of the nearest light ray at a wide angle of view to the eye, and bending it without causing the high-order light ray aberration, that is, the curvature of field and comma aberration in particular. The single lens would not involve unnecessary light ray aberration caused by a cemented surface. To enhance such an effect, the B group GRB preferably includes one or a plurality of positive meniscus-shaped single lenses only.

The objective lens system 311 shown in FIG. 13 has a plurality of the preferable configurations described above, with an angle between an exit light ray that is the light ray 45 at the maximum angle of view exiting the objective lens system 311 toward the eye and the optical axis AX of the objective lens system being 50 degrees or more. This means that the objective lens system 311 is an optical system with a wide angle of view for a fundus oculi.

Description of Preferable Practical Examples

Next, numerical practical examples of objective lens systems according to the technology of the present disclosure will be described. Out of practical examples described below, a practical example 1-1, a practical example 2-1, a practical example 3-1, a practical example 4-1, a practical example 5-1, a practical example 6-1, a practical example 7-1, a practical example 8-1, a practical example 9-1, a practical example 10-1, and a practical example 11-1 are practical examples of an SLO objective lens system, and a practical example 1-2, a practical example 2-2, and a practical example 3-2 are practical examples of an OCT objective lens system. The practical example 1-1 and the practical example 1-2 have common lens groups, and the practical example 1-1 and the practical example 1-2 can configure a practical example 1 of the complex objective lens system. In the same manner, the practical example 2-1 and the practical example 2-2 have common lens groups, and the practical example 2-1 and the practical example 2-2 can configure a practical example 2 of the complex objective lens system. In the same manner, the practical example 3-1 and the practical example 3-2 have common lens groups, and the practical example 3-1 and the practical example 3-2 can configure a practical example 3 of the complex objective lens system.

Each practical example is an ultra-wide-angle objective lens system in which the above-described ωmax is well over 60 degrees and reaches 72 degrees. The external irradiation angle can be twice as large as ωmax. Thus, the following practical examples can implement an ultra-wide angle ophthalmic device having a field of view with the external irradiation angle being 120 to 144 degrees, and enabling fundus imaging with the internal irradiation angle exceeding 200 degrees.

Practical Example 1-1

The practical example 1-1 is an objective lens system 311 that assumes an SLO objective lens system for a wavelength range of 450 m to 650 nm and a standard wavelength of 520 nm. FIG. 13 shows the lens configuration of the objective lens system 311 according to the practical example 1-1, together with a scanning center position Ps of a scanner and a pupil plane Pp of an eye 12. Note that. Ps and Pp are shown in the drawing for the purpose of indicating their positions in an optical axis direction, not for the purpose of indicating their shapes and sizes. The objective lens system 311 includes, in the following order from the side of the scanner, a first lens group G1 and a third lens group G3. The first lens group G1 and the third lens group G3 are separated by a maximum air gap in the objective lens system 311.

The first lens group G1 includes a meniscus lens L11 having a convex surface facing the side of the scanner, a meniscus lens L12 having a convex surface facing the side of the scanner, a negative lens L13 having a concave surface facing the side of the scanner, a positive meniscus lens L14 having a convex surface facing the side of the eye, and a positive lens L15. The lens L1 and the lens L12 are cemented to each other so as to form a meniscus-shaped lens component having a convex surface facing the side of the scanner, and the nearest lens surface to the scanner is aspherical. The third lens group G3 includes a positive lens L31, a positive lens L32, a negative lens L33, a positive lens L34, and a biconcave negative lens L35, and a positive meniscus lens L36 having a concave surface facing the side of the eye. More specifically, as for the shape of the positive lens L34, the absolute value of the radius of curvature of a lens surface on the side of the scanner is smaller than the absolute value of the radius of curvature of a lens surface on the side of the eye. The lens L32 and the lens L33 are cemented to each other, and the lens L34 and the lens L35 are cemented to each other. More specifically, the cemented lenses L32 and L33 form a biconvex lens component, and the cemented lenses L34 and L35 form a positive lens component having a convex surface facing the side of the scanner.

The objective lens system 311 can be regarded as consisting of the front group GF and the rear group GR described above. The front group GF corresponds to the first lens group G1, and the rear group GR corresponds to the third lens group G3. The A group GRA consists of the lens L31, the lens L32, and the lens L33. The B group GRB consists of the lens L34, the lens L35, and the lens L36.

Table 1 lists lens data of the practical example 1-1. The lens data lists, in the following order from the left column, a surface number, the radius of curvature, the distance between surfaces on the optical axis, a refractive index with respect to the d-line (a wavelength of 587.56 nm), and an Abbe number with respect to the d-line. A first surface of the lens data is the scanning center position Ps, and a value in the last row of the "thickness" column indicates a distance between the nearest lens surface to the eye 12 of the table and the pupil plane Pp on the optical axis.

TABLE 1

| surface number | radius | thickness | index | abbe number |
|---|---|---|---|---|
| 1 | ∞ | 23.41 | | |
| (ASP) 2 | 33.702 | 4.92 | 1.8513 | 40.1 |
| 3 | 44.620 | 4.97 | 1.6516 | 58.6 |
| 4 | 33.891 | 11.37 | | |
| 5 | −46.127 | 5.05 | 1.8000 | 29.8 |
| 6 | 171.416 | 7.43 | | |
| 7 | −67.910 | 11.04 | 2.0006 | 25.5 |
| 8 | −38.376 | 0.16 | | |
| 9 | 1.00E+18 | 22.06 | 1.6516 | 58.6 |
| 10 | −60.524 | 150.56 | | |
| 11 | 1.00E+18 | 16.70 | 1.6031 | 60.6 |
| 12 | −202.592 | 0.20 | | |
| 13 | 218.409 | 50.07 | 1.5163 | 64.1 |
| 14 | −87.895 | 5.00 | 1.6889 | 31.1 |
| 15 | −330.235 | 0.20 | | |
| 16 | 82.775 | 49.57 | 1.6584 | 50.9 |
| 17 | −153.617 | 5.00 | 1.8467 | 23.8 |
| 18 | 365.192 | 0.20 | | |
| 19 | 57.078 | 17.54 | 1.8830 | 40.8 |
| 20 | 153.597 | 25.00 | | |

In Table 1, (ASP) written in the "surface number" column indicates an aspherical surface. The aspherical surface is represented by the equation below:

$$zs=(c \cdot h^2)/[1+\{1-(1+k) \cdot h^2 \cdot c^2\}^{1/2}]+A \cdot h^4+B \cdot h^6+C \cdot h^8+D \cdot h^{10}+E \cdot h^{12}$$

where, "h" represents a height in a direction orthogonal to the optical axis, "zs" represents the distance (sag amount) between a tangent plane at a vertex of the aspherical surface and a position in the aspherical surface at the height h, "c" represents the reciprocal of a paraxial radius of curvature, "k" represents a conic constant, "A" represents a fourth-order aspherical-surface coefficient, "B" represents a sixth-order aspherical-surface coefficient, "C" represents an eighth-order aspherical-surface coefficient, "D" represents a tenth-order aspherical-surface coefficient, and "E" represents a twelfth-order aspherical-surface coefficient.

Table 2 lists the aspherical-surface coefficients of the aspherical surface according to the practical example 1-1. In Table 2, "E-n" (n is an integer) denotes "$-10^{-n}$".

TABLE 2

| surface number | 2 |
|---|---|
| Conic Constant | 0.000E+00 |
| 4th Order Coefficient | 1.981E−07 |
| 6th Order Coefficient | −2.865E−09 |

TABLE 2-continued

| surface number | 2 |
|---|---|
| 8th Order Coefficient | 7.929E−13 |
| 10th Order Coefficient | 0.000E+00 |
| 12th Order Coefficient | 0.000E+00 |

Note that, the manner of listing the lens data and the aspherical-surface coefficients and the manner of showing the configuration diagram described above are basically the same in the following practical examples.

Figure 14:
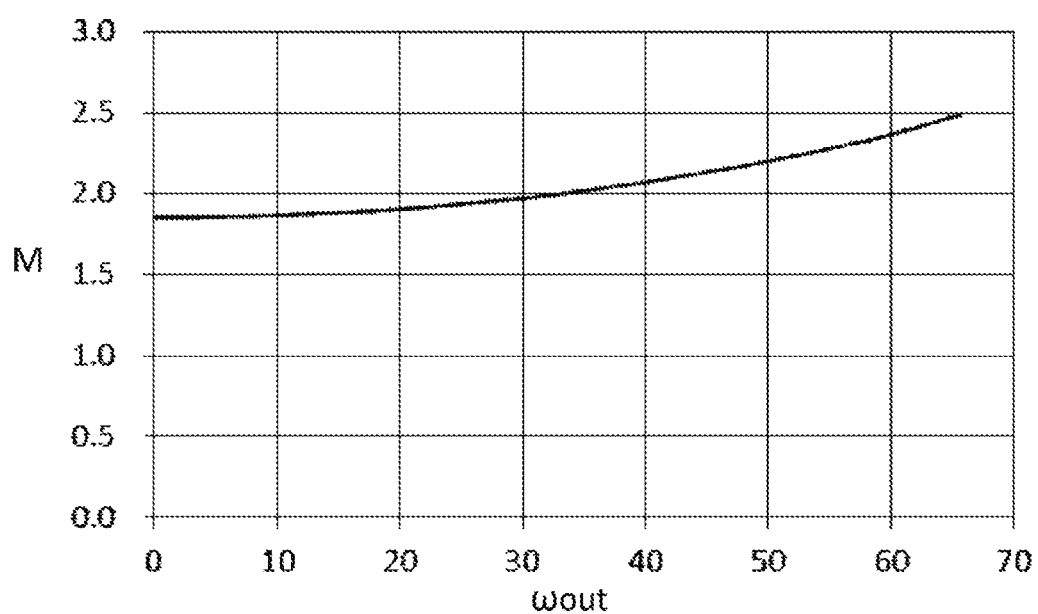
FIG. 14 is a graph showing the relationship between ωout and M in the objective lens system according to the practical example 1-1.
Figure 15:
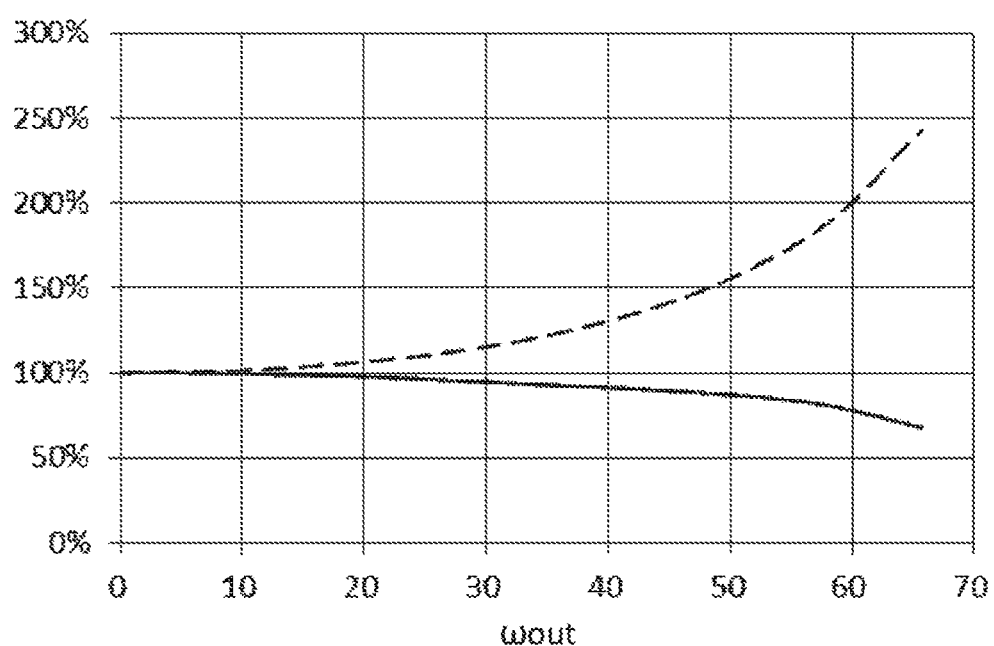
FIG. 15 is a graph showing the relationship between ωout and Pmax/Pmin in the objective lens system according to the practical example 1-1.

FIG. 14 shows the relationship between ωout and M according to the practical example 1-1. In FIG. 15, a solid line represents the relationship between ωout and Pmax/Pmin according to the practical example 1-1, and a broken line represents a curve of I/cos(ωout). The practical example 1-1 is an SLO objective lens system having an external irradiation angle of 132 degrees, and it is apparent from FIGS. 14 and 15 that the practical example 1-1 has superior performance, as a UWF objective lens.

Practical Example 1-2

Figure 16:
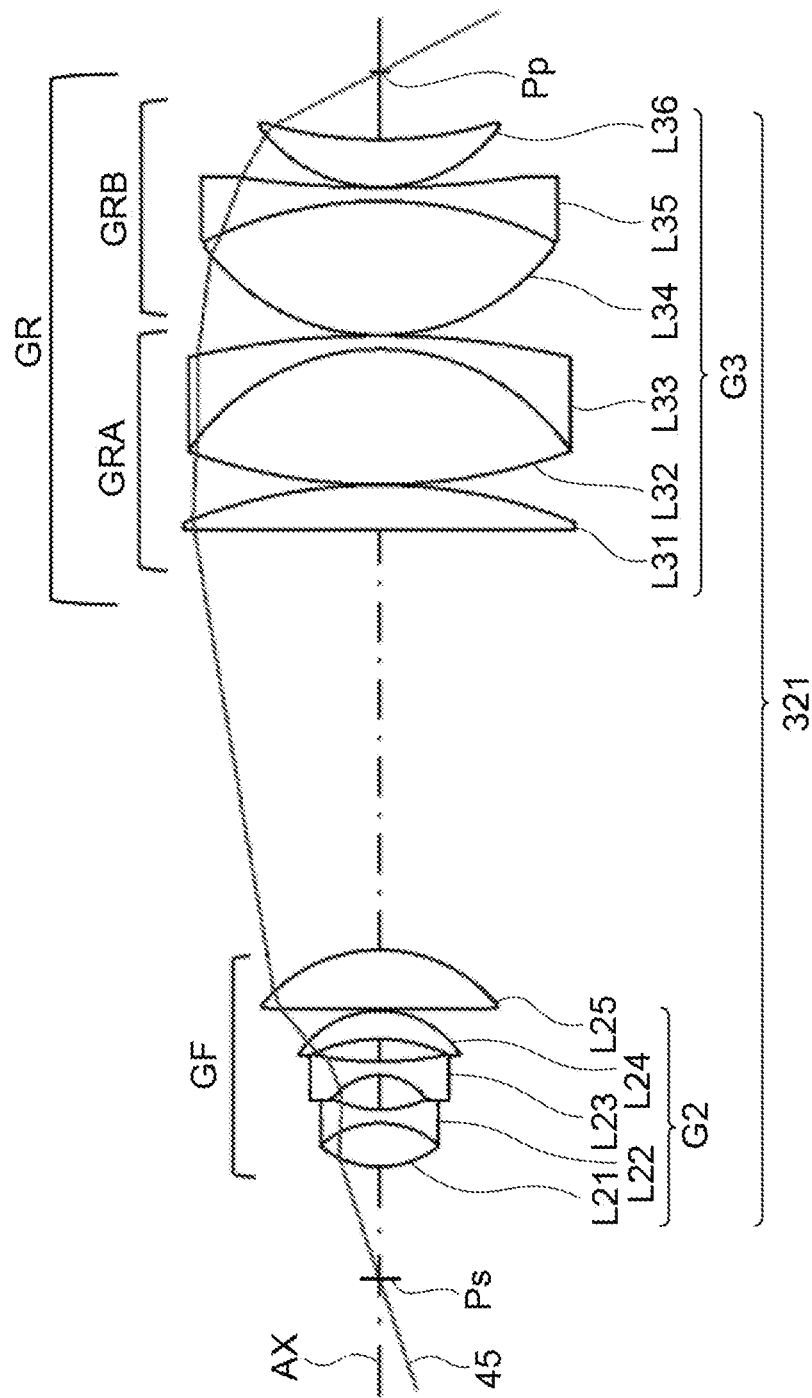
FIG. 16 is a drawing showing the configuration of an objective lens system according to a practical example 1-2.

The practical example 1-2 is an objective lens system 321 that assumes an OCT objective lens system for a wavelength range of 900 nm to 1050 nm and a standard wavelength of 1000 nm. FIG. 16 shows the lens configuration of the objective lens system 321 according to the practical example 1-2. The objective lens system 321 includes, in the following order from the side of the scanner, a second lens group G2 and a third lens group G3. The second lens group G2 and the third lens group G3 are separated by a maximum air gap in the objective lens system 321. The maximum air gap is suitable for disposing a beam combiner 26, e.g. a dichroic mirror or the like, having light combining and separating functions, thus allowing configuring a complex objective lens system for SLO and OCT.

The second lens group G2 has a similar configuration to the first lens group G1 according to the above practical example 1-1, except that the nearest meniscus-shaped lens component to the scanner, having a convex surface facing the side of the scanner, is a cemented lens constituted of a biconvex positive lens L21 and a biconcave negative lens L22. The third lens group G3 according to the practical example 1-2 is identical to the third lens group G3 according to the practical example 1-1.

The objective lens system 321 can be regarded as consisting of the front group GF and the rear group GR described above. The front group GF corresponds to the second lens group G2, and the rear group GR corrsponds to the third lens group G3. The lenses constituting the A group GRA and the B group GRB are the same as those of the practical example 1-1.

Table 3 lists lens data of the practical example 1-2.

TABLE 3

| surface number | radius | thickness | index | abbe number |
|---|---|---|---|---|
| 1 | ∞ | 41.48 | | |
| (ASP) 2 | 36.806 | 16.15 | 1.8513 | 40.1 |
| 3 | −34.380 | 5.01 | 1.7552 | 27.5 |
| 4 | 41.976 | 12.68 | | |
| 5 | −22.172 | 5.00 | 1.8010 | 35.0 |
| 6 | 126.002 | 8.31 | | |
| 7 | −61.667 | 10.55 | 2.0006 | 25.5 |
| 8 | −36.800 | 0.51 | | |
| 9 | 2.31E+03 | 22.01 | 1.6180 | 63.3 |
| 10 | −58.558 | 155.30 | | |
| 11 | 1.00E+18 | 16.70 | 1.6031 | 60.6 |
| 12 | −202.592 | 0.20 | | |
| 13 | 218.409 | 50.07 | 1.5163 | 64.1 |
| 14 | −87.895 | 5.00 | 1.6889 | 31.1 |
| 15 | −330.235 | 0.20 | | |
| 16 | 82.775 | 49.57 | 1.6584 | 50.9 |
| 17 | −153.617 | 5.00 | 1.8467 | 23.8 |
| 18 | 365.192 | 0.20 | | |
| 19 | 57.078 | 17.54 | 1.8830 | 40.8 |
| 20 | 153.597 | 25.08 | | |

Table 4 lists the aspherical-surface coefficients of the aspherical surface according to the practical example 1-2.

TABLE 4

| surface number | 2 |
|---|---|
| Conic Constant | 0.000E+00 |
| 4th Order Coefficient | 3.722E−07 |
| 6th Order Coefficient | −8.329E−10 |
| 8th Order Coefficient | 2.642E−12 |
| 10th Order Coefficient | 0.000E+00 |
| 12th Order Coefficient | 0.000E+00 |

Figure 17:
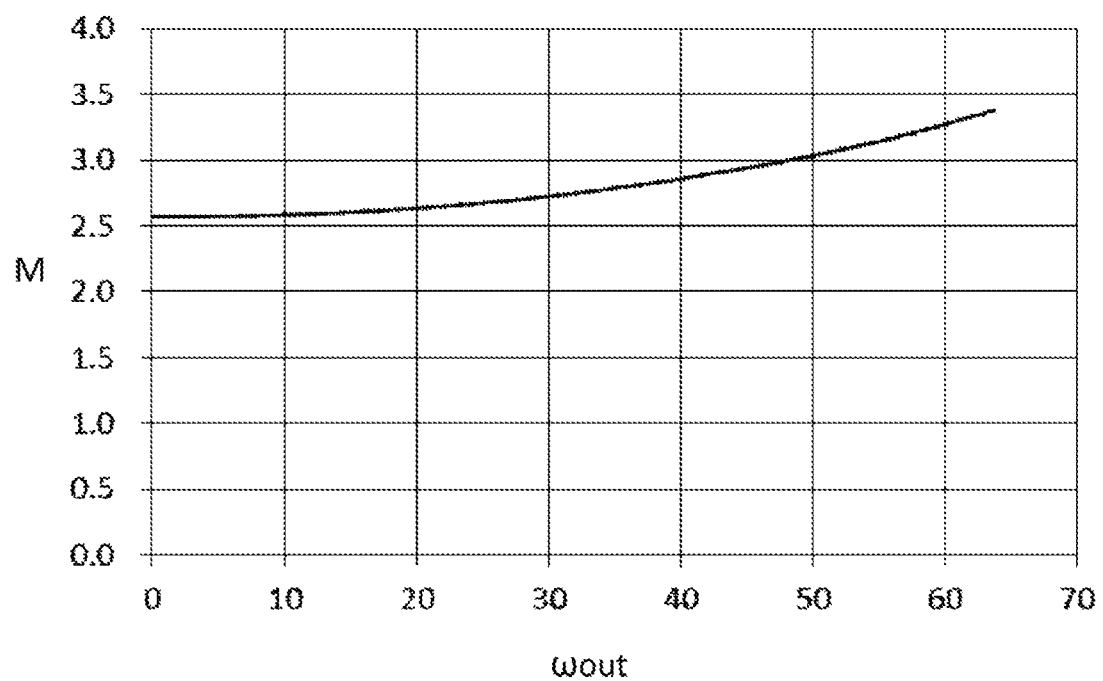
FIG. 17 is a graph showing the relationship between ωout and M in the objective lens system according to the practical example 1-2.
Figure 18:
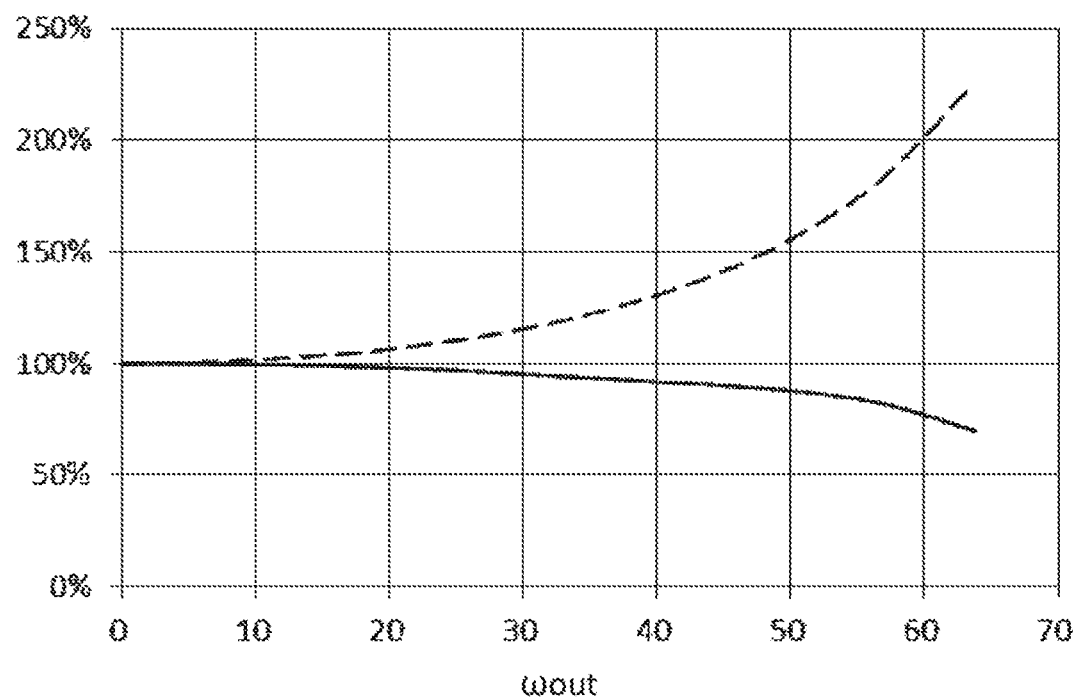
FIG. 18 is a graph showing the relationship between ωout and Pmax/Pmin in the objective lens system according to the practical example 1-2.

FIG. 17 shows the relationship between ωout and M according to the practical example 1-2. In FIG. 18, a solid line represents the relationship between ωout and Pmax/Pmin according to the practical example 1-2, and a broken line represents a curve of I/cos(ωout). The practical example 1-2 is an OCT objective lens system having an external irradiation angle of 128 degrees, and it is apparent from FIGS. 17 and 18 that the practical example 1-2 has superior performance, as a UWF objective lens.

Practical Example 2-1

Figure 19:
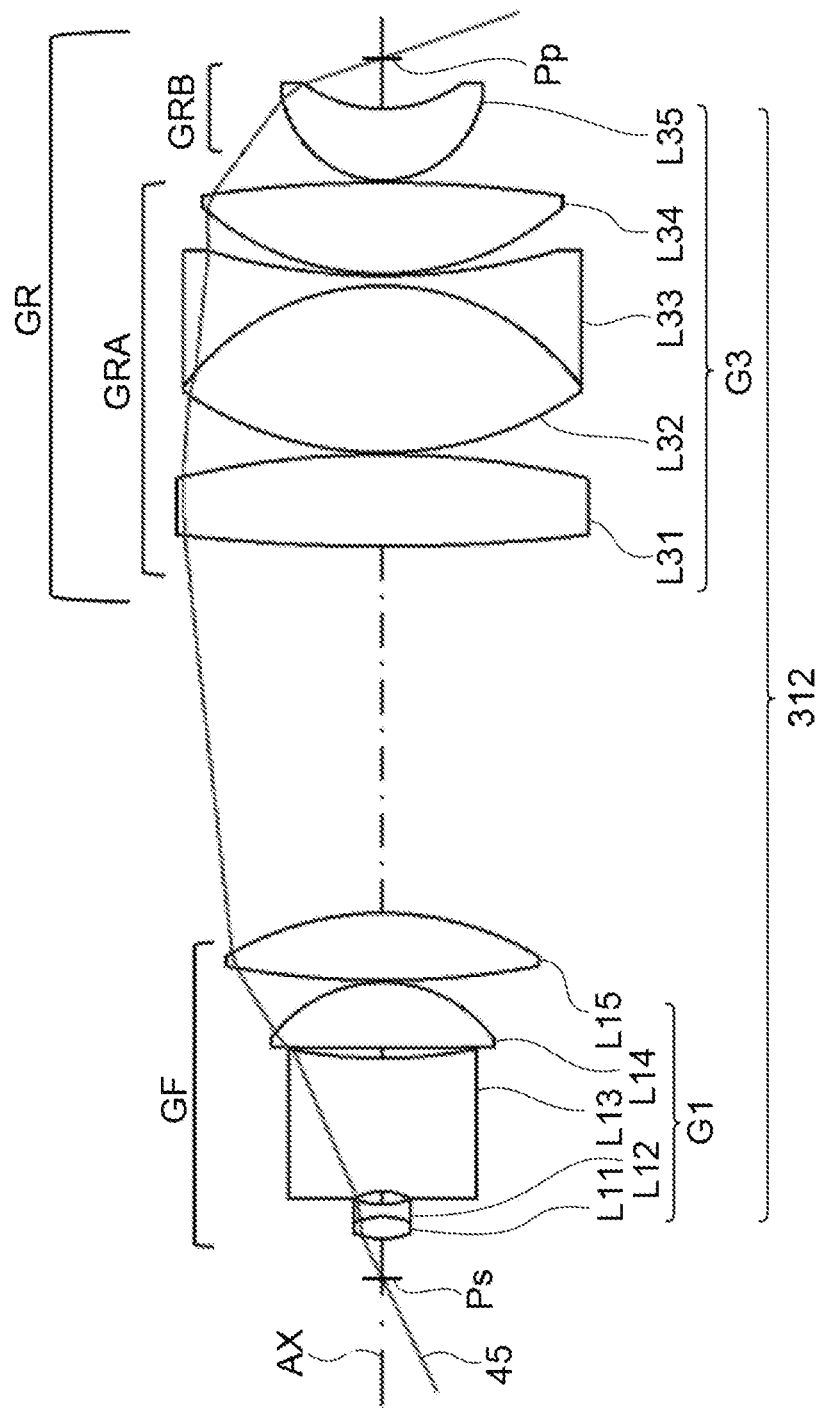
FIG. 19 is a drawing showing the configuration of an objective lens system according to a practical example 2-1.

The practical example 2-1 is an objective lens system 312 that assumes the SLO objective lens system. FIG. 19 shows the lens configuration of the objective lens system 312 according to the practical example 2-1. The objective lens system 312 includes, in the following order from the side of the scanner, a first lens group G1 and a third lens group G3. The first lens group G1 and the third lens group G3 are separated by a maximum air gap in the objective lens system 312.

The first lens group G1 includes a biconvex positive lens L11, a biconcave negative lens L12, a biconcave negative lens L13, a positive lens L14 having a convex surface facing the side of the eye, and a positive lens L15. The lens L11 and the lens L12 are cemented to each other so as to form a meniscus-shaped lens component having a convex surface facing the side of the scanner, and the nearest lens surface to the scanner is aspherical. The third lens group G3 includes a positive lens L31, a biconvex positive lens L32, a biconcave negative lens L33, a positive lens L34 having a convex surface facing the side of the scanner, and a positive meniscus lens L35 having a concave surface facing the side of the eye. The lens L32 and the lens L33 are cemented to each other so as to form a meniscus-shaped lens component having a convex surface facing the side of the scanner.

The objective lens system 312 can be regarded as consisting of the front group GF and the rear group GR described above. The front group GF corresponds to the first lens group G1, and the rear group GR corresponds to the third lens group G3. The A group GRA consists of the lens L31, the lens L32, the lens L33, and the lens L34. The B group GRB consists of the lens L35.

Table 5 lists lens data of the practical example 2-1.

TABLE 5

| surface number | radius | thickness | index | abbe number |
|---|---|---|---|---|
| 1 | ∞ | 19.39 | | |
| (ASP) 2 | 35.450 | 10.88 | 1.7620 | 40.1 |
| 3 | −35.551 | 6.00 | 1.6127 | 44.5 |
| 4 | 38.552 | 6.30 | | |
| 5 | −30.427 | 65.31 | 1.7408 | 27.7 |
| 6 | 244.101 | 5.00 | | |
| 7 | 2819.264 | 32.13 | 1.4978 | 82.6 |
| 8 | −70.370 | 1.00 | | |
| 9 | 438.700 | 33.00 | 1.5750 | 41.5 |
| 10 | −154.053 | 179.69 | | |
| 11 | 930.895 | 45.00 | 1.5891 | 61.2 |
| 12 | −459.976 | 1.00 | | |
| 13 | 180.153 | 81.60 | 1.6230 | 58.1 |
| 14 | −124.896 | 5.00 | 1.7847 | 25.6 |
| 15 | 315.278 | 1.00 | | |
| 16 | 140.845 | 44.68 | 1.7130 | 54.0 |
| 17 | −626.441 | 1.00 | | |
| 18 | 51.156 | 35.15 | 1.7130 | 54.0 |
| 19 | 69.870 | 25.00 | | |

Table lists the aspherical-surface coefficients of the aspherical surface according to the practical example 2-1.

TABLE 6

| surface number | 2 |
|---|---|
| Conic Constant | 0.000E+00 |
| 4th Order Coefficient | −1.078E−05 |
| 6th Order Coefficient | 4.006E−08 |
| 8th Order Coefficient | −8.501E−11 |
| 10th Order Coefficient | 0.000E+00 |
| 12th Order Coefficient | 0.000E+00 |

Figure 20:
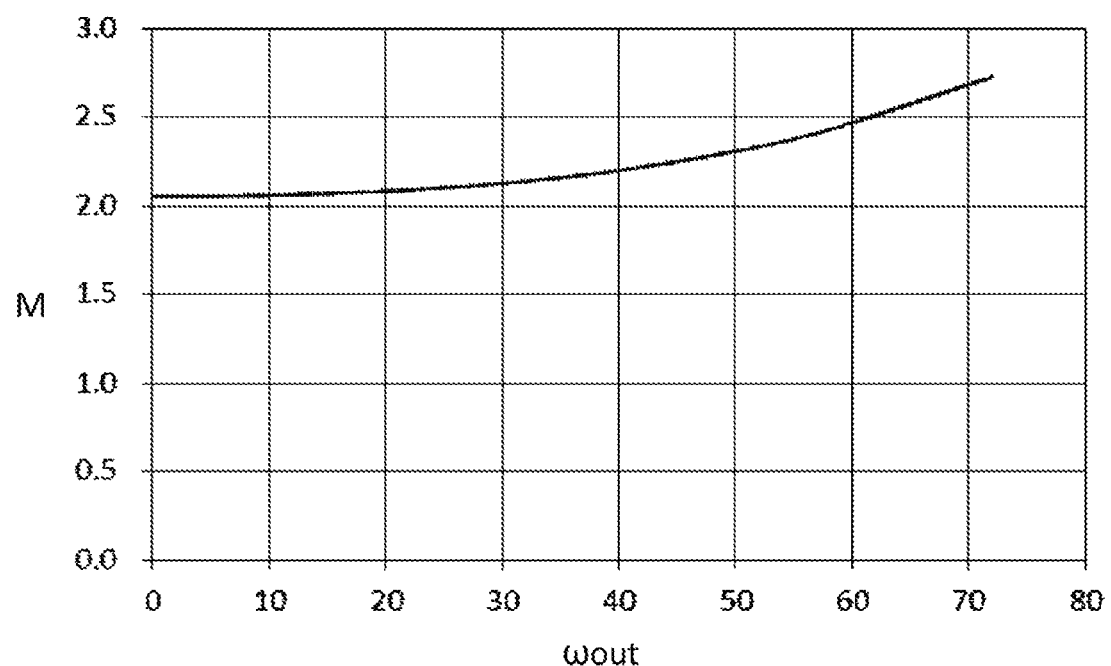
FIG. 20 is a graph showing the relationship between ωout and M in the objective lens system according to the practical example 2-1.
Figure 21:
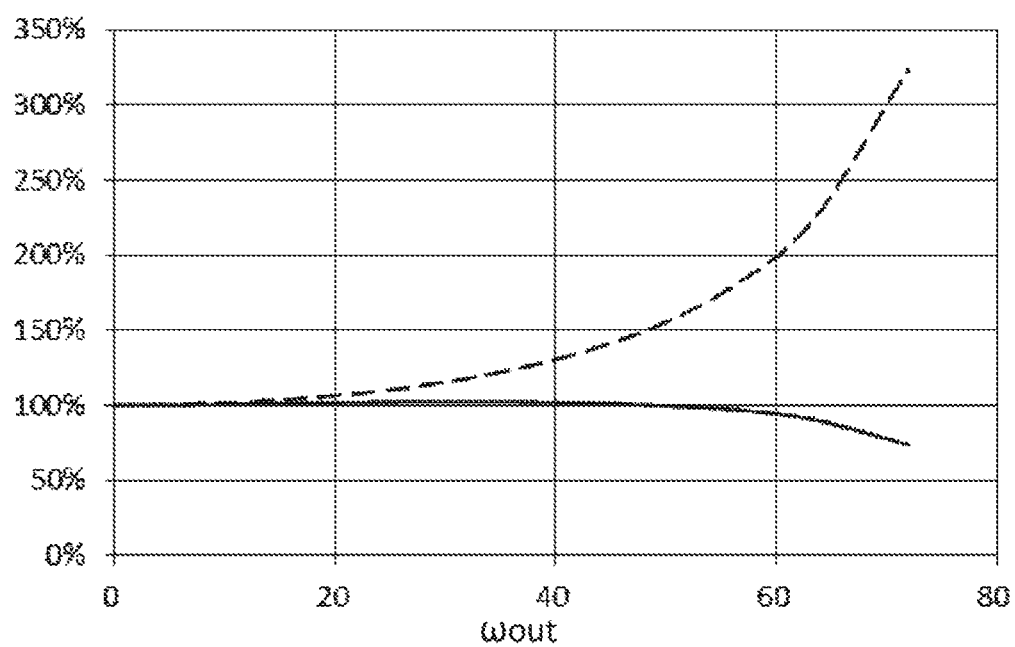
FIG. 21 is a graph showing the relationship between ωout and Pmax/Pmin in the objective lens system according to the practical example 2-1.

FIG. 20 shows the relationship between ωout and M according to the practical example 2-1. In FIG. 21, a solid line represents the relationship between ωout and Pmax/Pmin according to the practical example 2-1, and a broken line represents a curve of 1/cos((out). The practical example 2-1 is an SLO objective lens system having an external irradiation angle of 144 degrees, and it is apparent from FIGS. 20 and 21 that the practical example 2-1 has superior performance, as a UWF objective lens.

Practical Example 2-2

Figure 22:
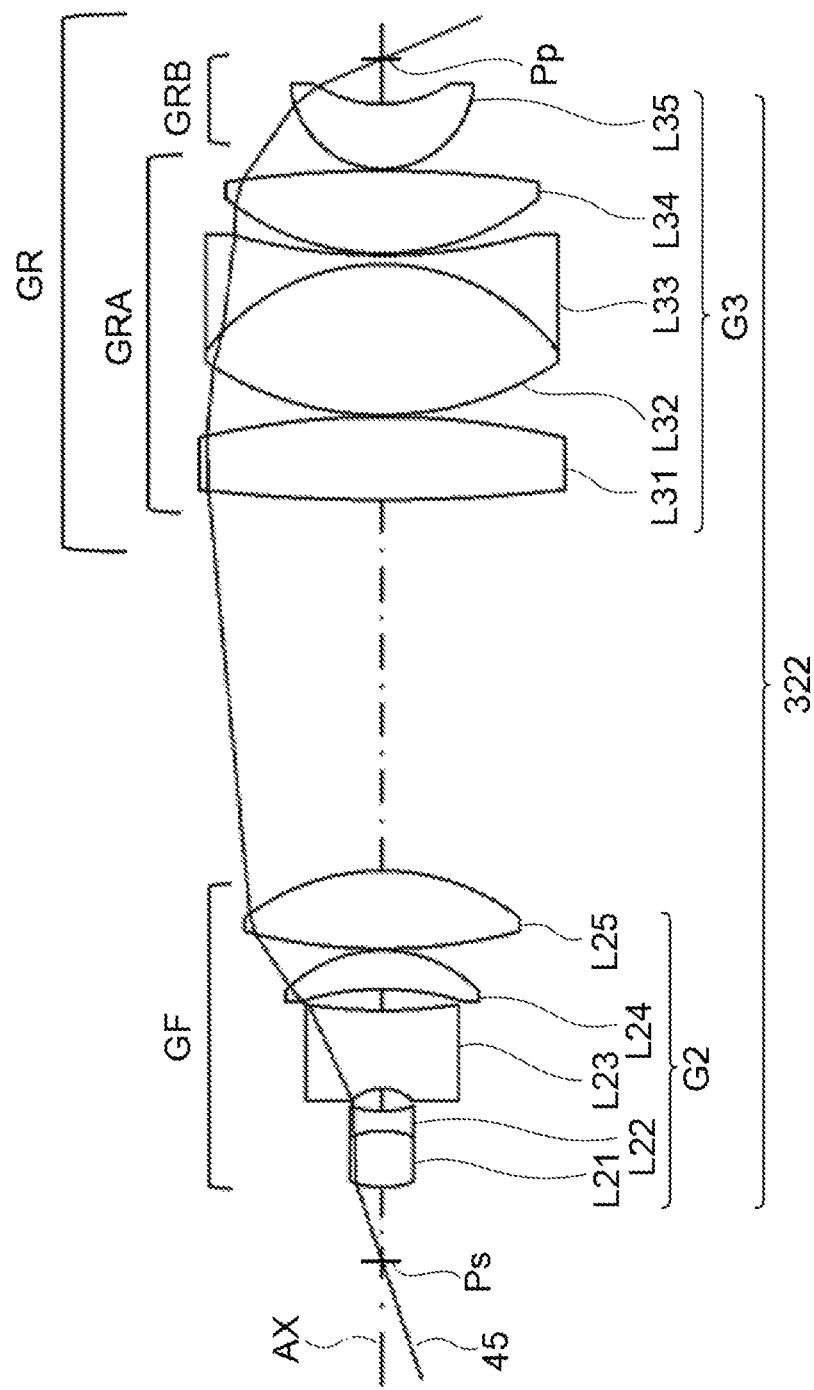
FIG. 22 is a drawing showing the configuration of an objective lens system according to a practical example 2-2.

The practical example 2-2 is an objective lens system 322 that assumes the OCT objective lens system. FIG. 22 shows the lens configuration of the objective lens system 322 according to the practical example 2-2. The objective lens system 322 includes, in the following order from the side of the scanner, a second lens group G2 and a third lens group G3. The second lens group G2 and the third lens group G3 are separated by a maximum air gap in the objective lens system 322. The second lens group G2 has a similar configuration to the first lens group G1 according to the above practical example 2-1 shown in FIG. 19. The third lens group G3 according to the practical example 2-2 is identical to the third lens group G3 according to the practical example 2-1.

The objective lens system 322 can be regarded as consisting of the front group GF and the rear group GR described above. The front group GF corresponds to the second lens group G2, and the rear group GR corresponds to the third lens group G3. The lenses constituting the A group GRA and the B group GRB are the same as those of the practical example 2-1.

Table 7 lists lens data of the practical example 2-2.

TABLE 7

| surface number | radius | thickness | index | abbe number |
|---|---|---|---|---|
| 1 | ∞ | 39.91 | | |
| (ASP) 2 | 52.124 | 30.55 | 1.7620 | 40.1 |
| 3 | −45.402 | 10.67 | 1.6127 | 44.5 |
| 4 | 59.213 | 12.20 | | |
| 5 | −24.669 | 42.39 | 1.7408 | 27.7 |
| 6 | 296.498 | 11.41 | | |
| 7 | −157.302 | 21.04 | 2.0006 | 25.5 |
| 8 | −75.886 | 0.87 | | |
| 9 | 312.301 | 42.29 | 1.4978 | 82.6 |
| 10 | −126.843 | 200.97 | | |
| 11 | 930.895 | 45.00 | 1.5891 | 61.2 |
| 12 | −459.976 | 1.00 | | |
| 13 | 180.153 | 81.60 | 1.6230 | 58.1 |
| 14 | −124.896 | 5.00 | 1.7847 | 25.6 |
| 15 | 315.278 | 1.00 | | |
| 16 | 140.845 | 44.68 | 1.7130 | 54.0 |
| 17 | −626.441 | 1.00 | | |
| 18 | 51.156 | 35.15 | 1.7130 | 54.0 |
| 19 | 69.870 | 25.00 | | |

Table 8 lists the aspherical-surface coefficients of the aspherical surface according to the practical example 2-2.

TABLE 8

| surface number | 2 |
|---|---|
| Conic Constant | 0.000E+00 |
| 4th Order Coefficient | 4.875E−07 |
| 6th Order Coefficient | −1.307E−10 |
| 8th Order Coefficient | 8.134E−13 |
| 10th Order Coefficient | 0.000E+00 |
| 12th Order Coefficient | 0.000E+00 |

Figure 23:
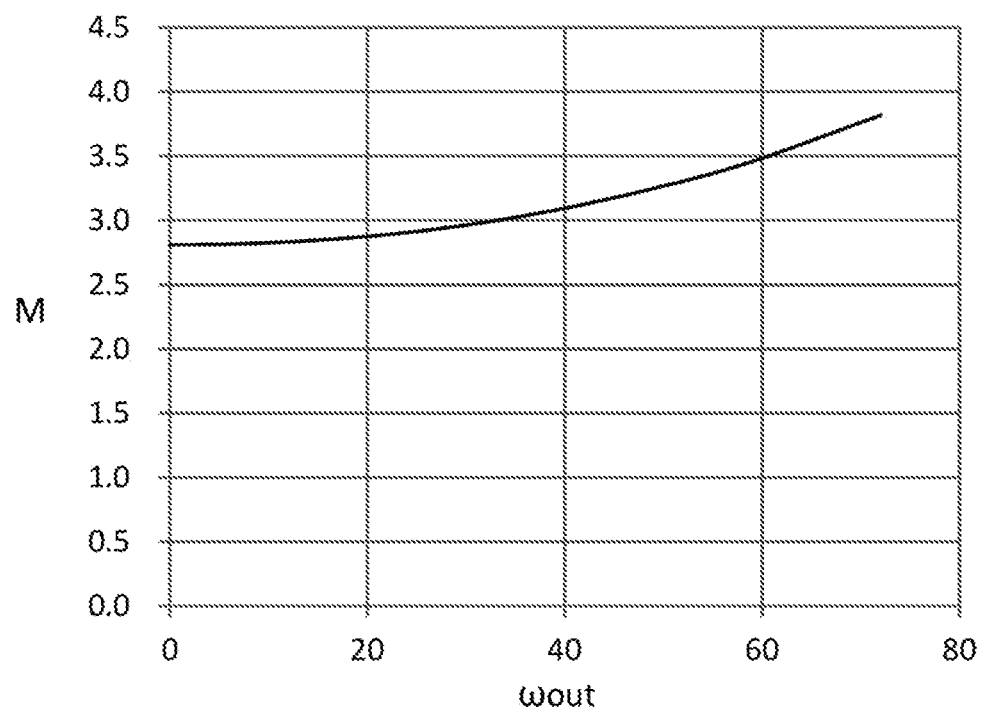
FIG. 23 is a graph showing the relationship between ωout and M in the objective lens system according to the practical example 2-2.
Figure 24:
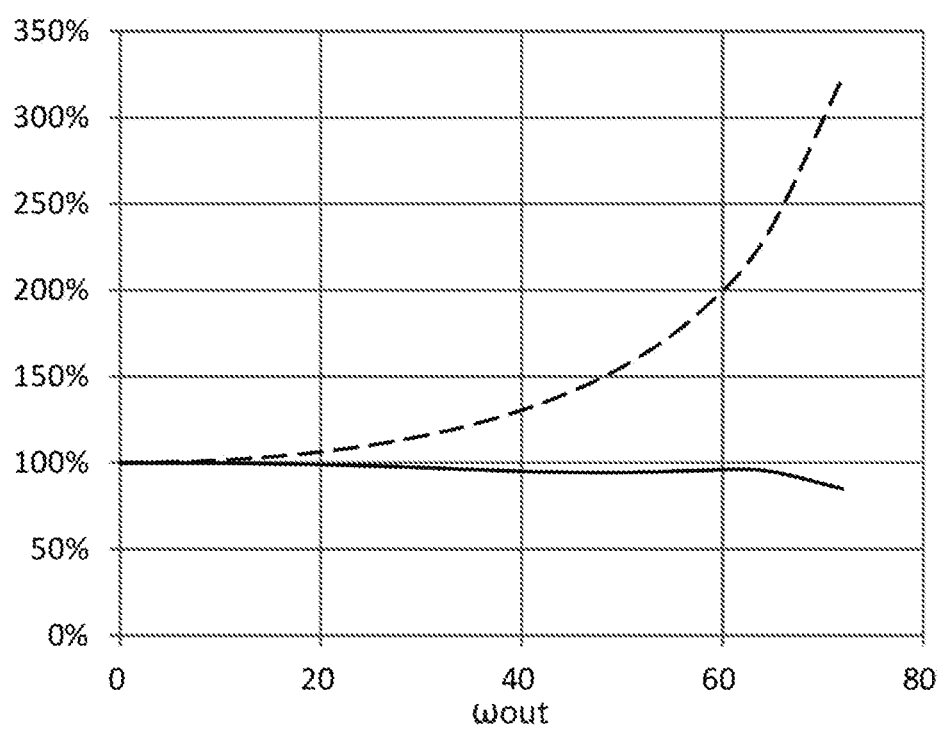
FIG. 24 is a graph showing the relationship between ωout and Pmax/Pmin in the objective lens system according to the practical example 2-2.

FIG. 23 shows the relationship between ωout and M according to the practical example 2-2. In FIG. 24, a solid line represents the relationship between ωout and Pmax/Pmin according to the practical example 2-2, and a broken line represents a curve of 1/cos(ωout). The practical example 2-2 is an OCT objective lens system having an external irradiation angle of 144 degrees, and it is apparent from FIGS. 23 and 24 that the practical example 2-2 has superior performance, as a UWF objective lens.

Practical Example 3-1

Figure 25:
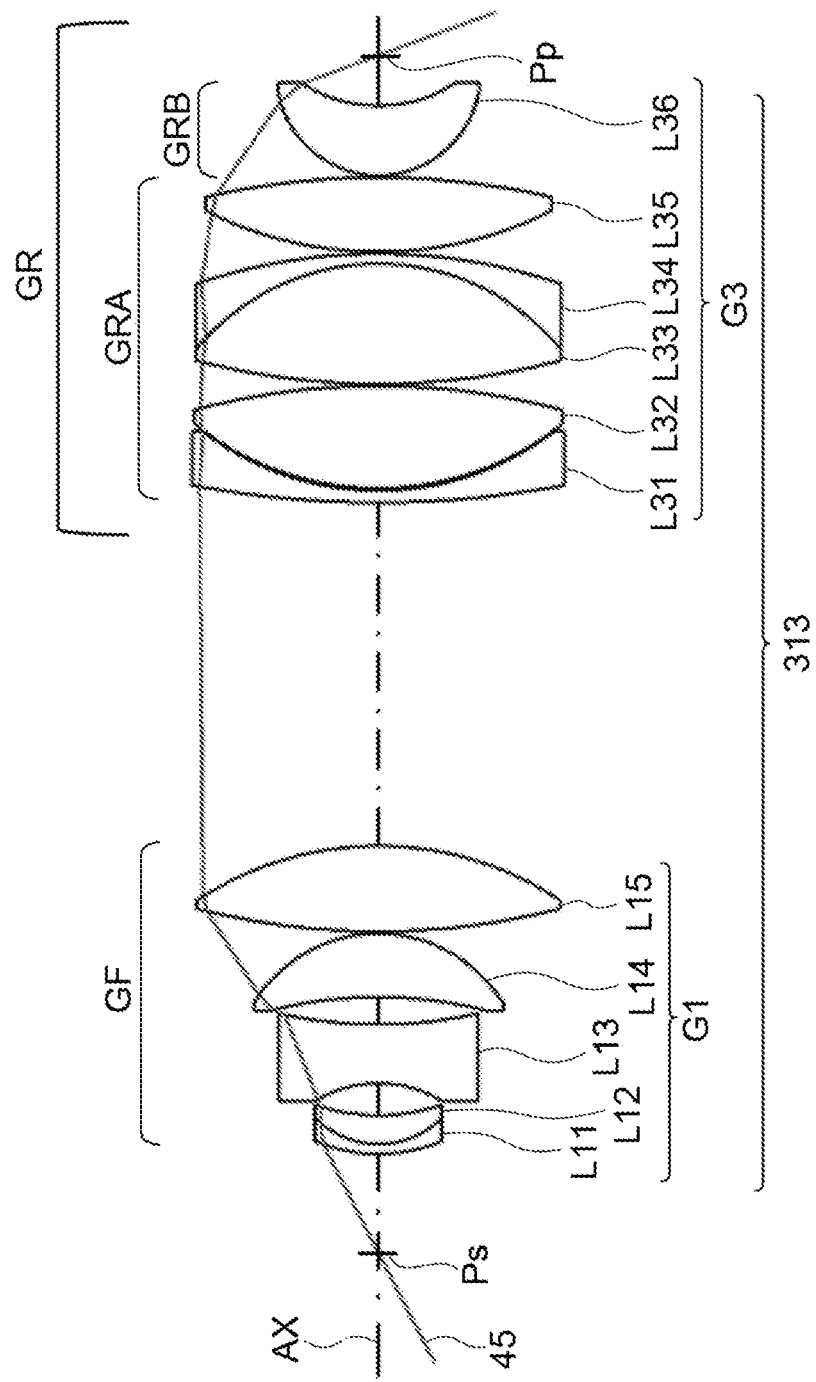
FIG. 25 is a drawing showing the configuration of an objective lens system according to a practical example 3-1.

The practical example 3-1 is an objective lens system 313 that assumes the SLO objective lens system. FIG. 25 shows the lens configuration of the objective lens system 313 according to the practical example 3-1. The objective lens system 313 includes, in the following order from the side of the scanner, a first lens group G1 and a third lens group G3. The first lens group G1 and the third lens group G3 are separated by a maximum air gap in the objective lens system 313.

The first lens group G1 includes a negative meniscus lens L11 having a convex surface facing the side of the scanner, a positive meniscus lens L12 having a convex surface facing the side of the scanner, a biconcave negative lens L13, a positive lens L14 having a convex surface facing the side of the eye, and a positive lens L15. The lens L11 and the lens L12 are cemented to each other so as to form a meniscus-shaped lens component having a convex surface facing the side of the scanner. The third lens group G3 includes a negative meniscus lens L31 having a convex surface facing the side of the scanner, a biconvex positive lens L32, a biconvex positive lens L33, a negative meniscus lens L34 having a convex surface facing the side of the eye, a positive lens L35 having a convex surface facing the side of the scanner, and a positive meniscus lens L36 having a concave surface facing the side of the eye. The lens L31 and the lens L32 are cemented to each other so as to form a biconvex positive lens component, and the lens L33 and the lens L34 are cemented to each other so as to form a biconvex positive lens component. The third lens group G3 according to the practical example 3-1 has the two cemented lenses, as in the case of the above practical example 1-1 (FIG. 13), and, while two cemented surfaces of the third lens group G3 according to the practical example 1-1 are arranged such that their convex surfaces face the side of the eye, two cemented surfaces of the third lens group G3 according to the practical example 3-1 are arranged such that their concave surfaces face each other. The nearest lens surface to the eye is aspherical.

The objective lens system 311 can be regarded as consisting of the front group GF and the rear group GR described above. The front group GF corresponds to the first lens group G1, and the rear group GR corresponds to the third lens group G3. The A group GRA consists of the lens L31, the lens L32, the lens L33, the lens L34, and the lens L35. The B group GRB consists of the lens L36.

Table 9 lists lens data of the practical example 3-1.

TABLE 9

| surface number | radius | thickness | index | abbe number |
|---|---|---|---|---|
| 1 | ∞ | 50.00 | | |
| 2 | 85.463 | 5.00 | 1.5530 | 55.1 |
| 3 | 47.235 | 14.52 | 1.7847 | 25.6 |
| 4 | 101.009 | 16.24 | | |
| 5 | −63.727 | 29.65 | 1.7618 | 26.6 |
| 6 | 233.733 | 13.97 | | |
| 7 | −228.024 | 32.12 | 1.7618 | 26.6 |
| 8 | −76.550 | 1.00 | | |
| 9 | 385.923 | 43.28 | 1.6188 | 63.7 |
| 10 | −173.520 | 173.62 | | |
| 11 | 529.570 | 6.00 | 1.7847 | 25.6 |
| 12 | 151.818 | 1.24 | | |
| 13 | 154.748 | 51.80 | 1.5168 | 64.1 |
| 14 | −375.360 | 1.00 | | |
| 15 | 380.170 | 60.77 | 1.5168 | 64.1 |
| 16 | −124.356 | 5.00 | 1.7847 | 25.6 |
| 17 | −299.529 | 1.00 | | |
| 18 | 202.435 | 37.61 | 1.6188 | 63.7 |
| 19 | −407.052 | 1.00 | | |
| 20 | 53.068 | 35.31 | 1.7725 | 49.6 |
| (ASP) 21 | 80.000 | 25.00 | | |

Table 10 lists the aspherical-surface coefficients of the aspherical surface according to the practical example 3-1.

TABLE 10

| surface number | 21 |
|---|---|
| Conic Constant | 0.000E+00 |
| 4th Order Coefficient | 8.315E−07 |
| 6th Order Coefficient | −4.003E−10 |
| 8th Order Coefficient | 1.001E−13 |
| 10th Order Coefficient | 0.000E+00 |
| 12th Order Coefficient | 0.000E+00 |

Figure 26:
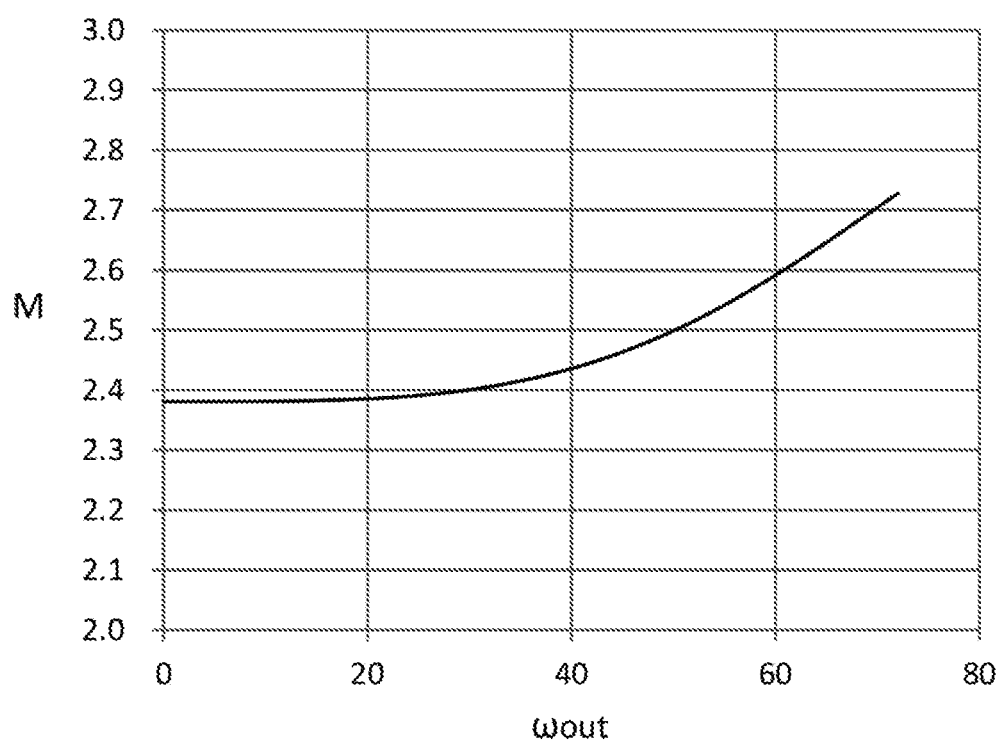
FIG. 26 is a graph showing the relationship between ωout and M in the objective lens system according to the practical example 3-1.
Figure 27:
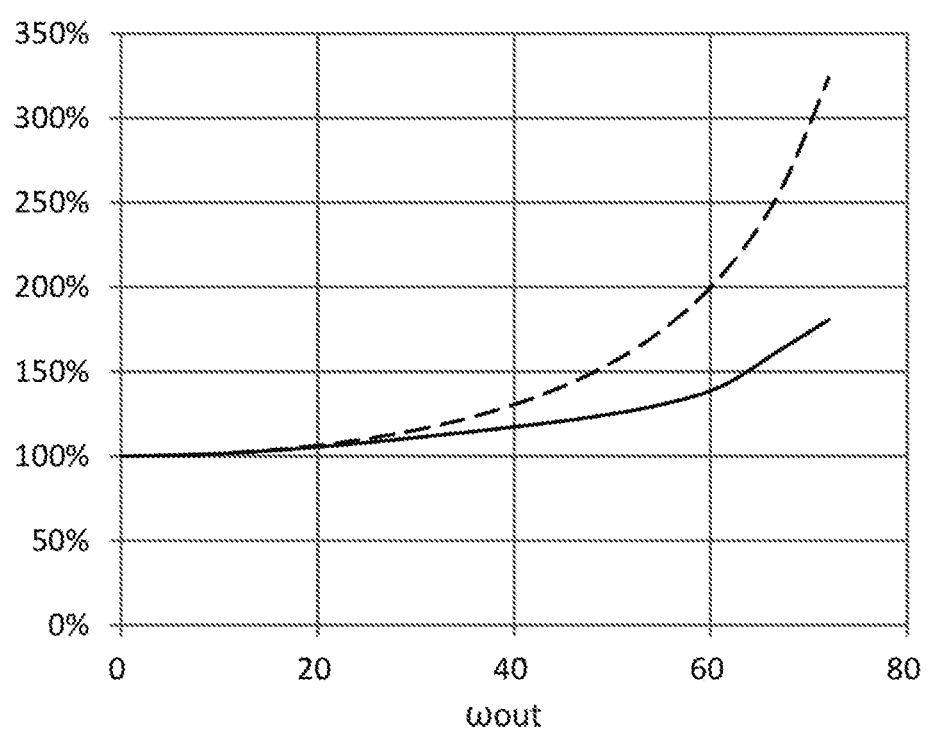
FIG. 27 is a graph showing the relationship between ωout and Pmax/Pmin in the objective lens system according to the practical example 3-1.

FIG. 26 shows the relationship between ωout and M according to the practical example 3-1. In FIG. 27, a solid line represents the relationship between ωout and Pmax/Pmin according to the practical example 3-1, and a broken line represents a curve of 1/cos(out). The practical example 3-1 is an SLO objective lens system having an external irradiation angle of 144 degrees, and it is apparent from FIGS. 26 and 27 that the practical example 3-1 has superior performance, as a UWF objective lens.

Practical Example 3-2

Figure 28:
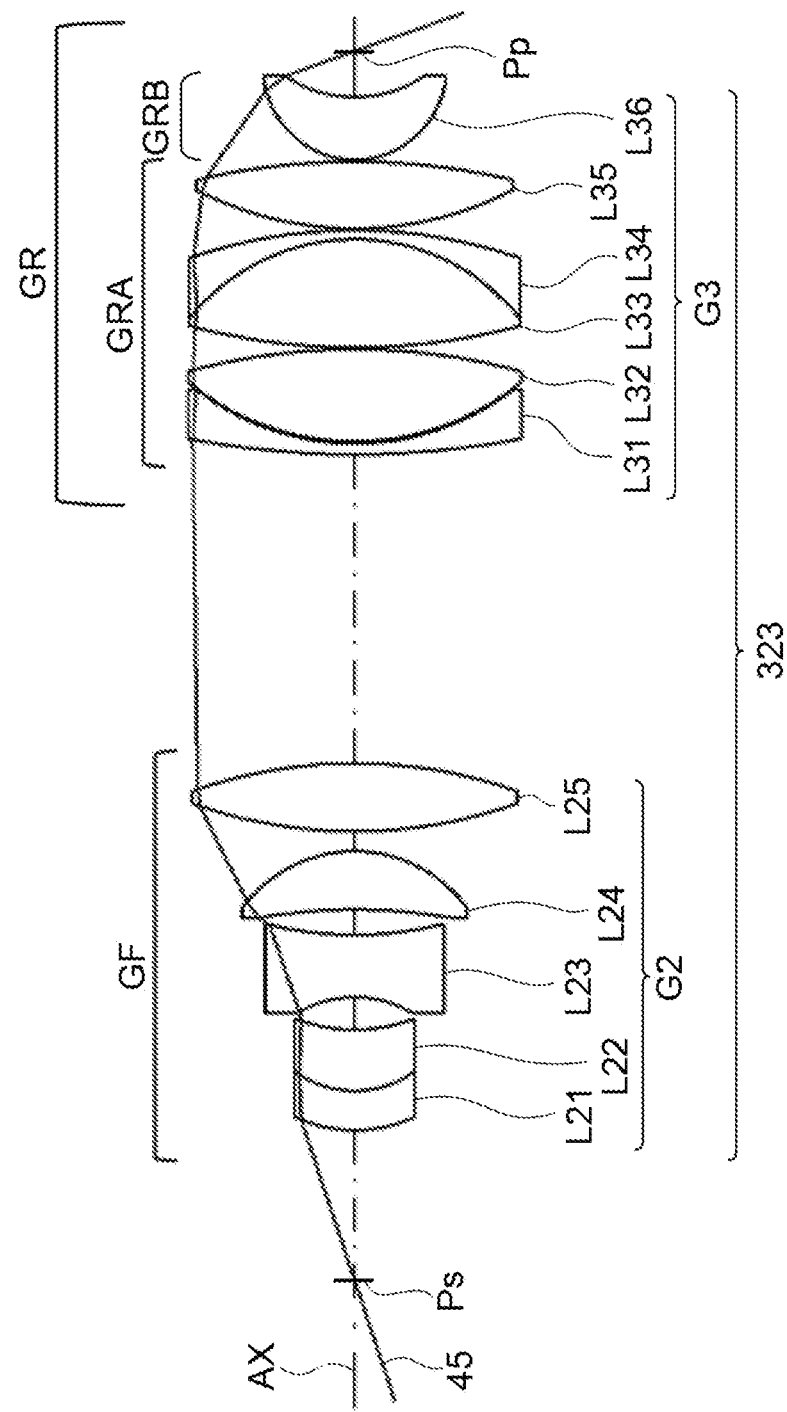
FIG. 28 is a drawing showing the configuration of an objective lens system according to a practical example 3-2.

The practical example 3-2 is an objective lens system 323 that assumes the OCT objective lens system. FIG. 28 shows the lens configuration of the objective lens system 323 according to the practical example 3-2. The objective lens system 323 includes, in the following order from the side of the scanner, a second lens group G2 and a third lens group G3. The second lens group G2 and the third lens group G3 are separated by a maximum air gap in the objective lens system 323. The second lens group G2 has a similar configuration to the first lens group G1 shown in FIG. 25. However, the meniscus lens component of the first lens group G1 that is the nearest to the scanner and has a convex surface facing the side of the scanner has the thickest center thickness in the first lens group G1 according to the practical example 3-2, though has the thinnest center thickness in the first lens group G1 according to the practical example 3-1. The third lens group G3 according to the practical example 3-2 is identical to the third lens group G3 according to the practical example 3-1.

The objective lens system 323 can be regarded as consisting of the front group GF and the rear group GR described above. The front group GF corresponds to the second lens group G2, and the rear group GR corresponds to the third lens group G3. The lenses constituting the A group GRA and the B group GRB are the same as those of the practical example 3-1.

Table 11 lists lens data of the practical example 3-2.

TABLE 11

| surface number | radius | thickness | index | abbe number |
|---|---|---|---|---|
| 1 | ∞ | 84.47 | | |
| 2 | 82.086 | 22.21 | 1.5530 | 55.1 |
| 3 | 60.141 | 34.30 | 1.7847 | 25.6 |
| 4 | 94.801 | 18.24 | | |
| 5 | −66.764 | 35.00 | 1.7618 | 26.6 |
| 6 | 212.352 | 14.29 | | |
| 7 | −330.004 | 32.72 | 1.6968 | 55.5 |
| 8 | −81.792 | 11.23 | | |
| 9 | 287.705 | 38.19 | 1.6188 | 63.7 |
| 10 | −287.068 | 173.62 | | |
| 11 | 529.570 | 6.00 | 1.7847 | 25.6 |
| 12 | 151.818 | 1.24 | | |
| 13 | 154.748 | 51.80 | 1.5168 | 64.1 |
| 14 | −375.360 | 1.00 | | |
| 15 | 380.170 | 60.77 | 1.5168 | 64.1 |
| 16 | −124.356 | 5.00 | 1.7847 | 25.6 |
| 17 | −299.529 | 1.00 | | |
| 18 | 202.435 | 37.61 | 1.6188 | 63.7 |

TABLE 11-continued

| surface number | radius | thickness | index | abbe number |
|---|---|---|---|---|
| 19 | −407.052 | 1.00 | | |
| 20 | 53.068 | 35.31 | 1.7725 | 49.6 |
| (ASP) 21 | 80.000 | 25.00 | | |

Table 12 lists the aspherical-surface coefficients of the aspherical surface according to the practical example 3-2.

TABLE 12

| surface number | 21 |
|---|---|
| Conic Constant | 0.000E+00 |
| 4th Order Coefficient | 8.315E−07 |
| 6th Order Coefficient | −4.003E−10 |
| 8th Order Coefficient | 1.001E−13 |
| 10th Order Coefficient | 0.000E+00 |
| 12th Order Coefficient | 0.000E+00 |

Figure 29:
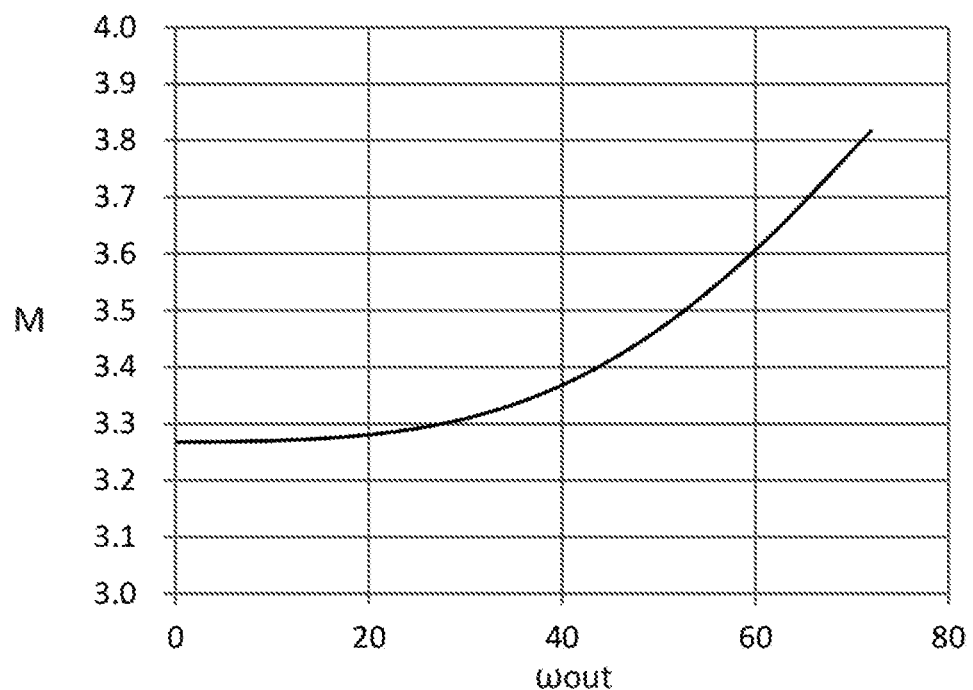
FIG. 29 is a graph showing the relationship between ωout and M in the objective lens system according to the practical example 3-2.
Figure 30:
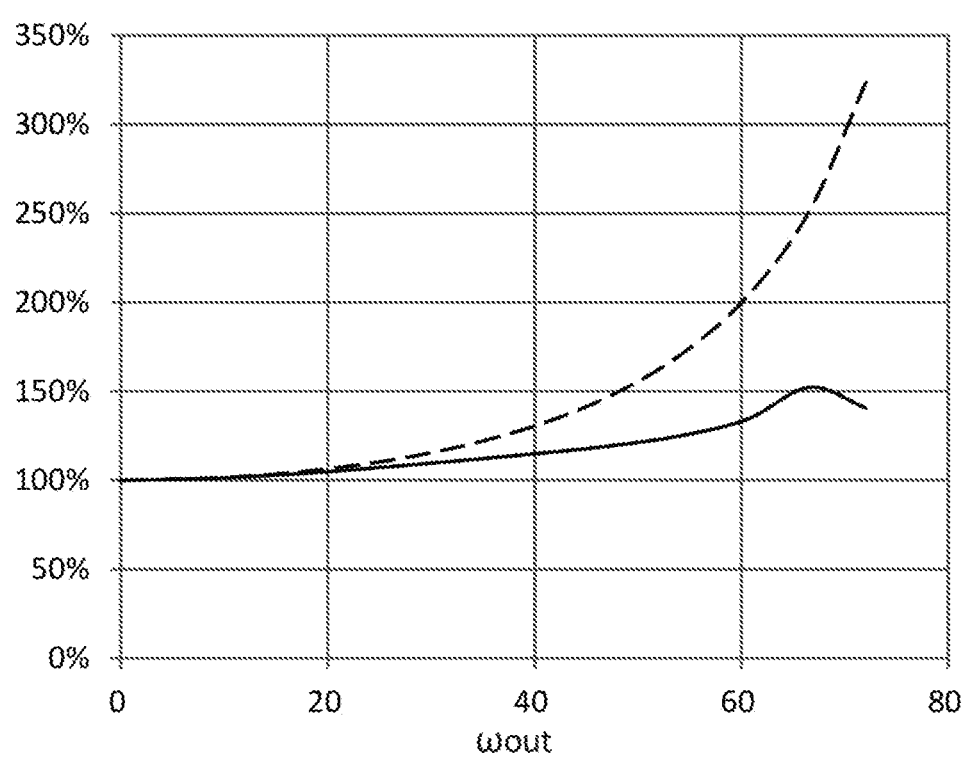
FIG. 30 is a graph showing the relationship between ωout and Pmax/Pmin in the objective lens system according to the practical example 3-2.

FIG. 29 shows the relationship between ωout and M according to the practical example 3-2. In FIG. 30, a solid line represents the relationship between ωout and Pmax/Pmin according to the practical example 3-2, and a broken line represents a curve of 1/cos(ωout). The practical example 3-2 is an OCT objective lens system having an external irradiation angle of 144 degrees, and it is apparent from FIGS. 29 and 30 that the practical example 3-2 has superior performance, as a UWF objective lens.

Practical Example 4-1

Figure 31:
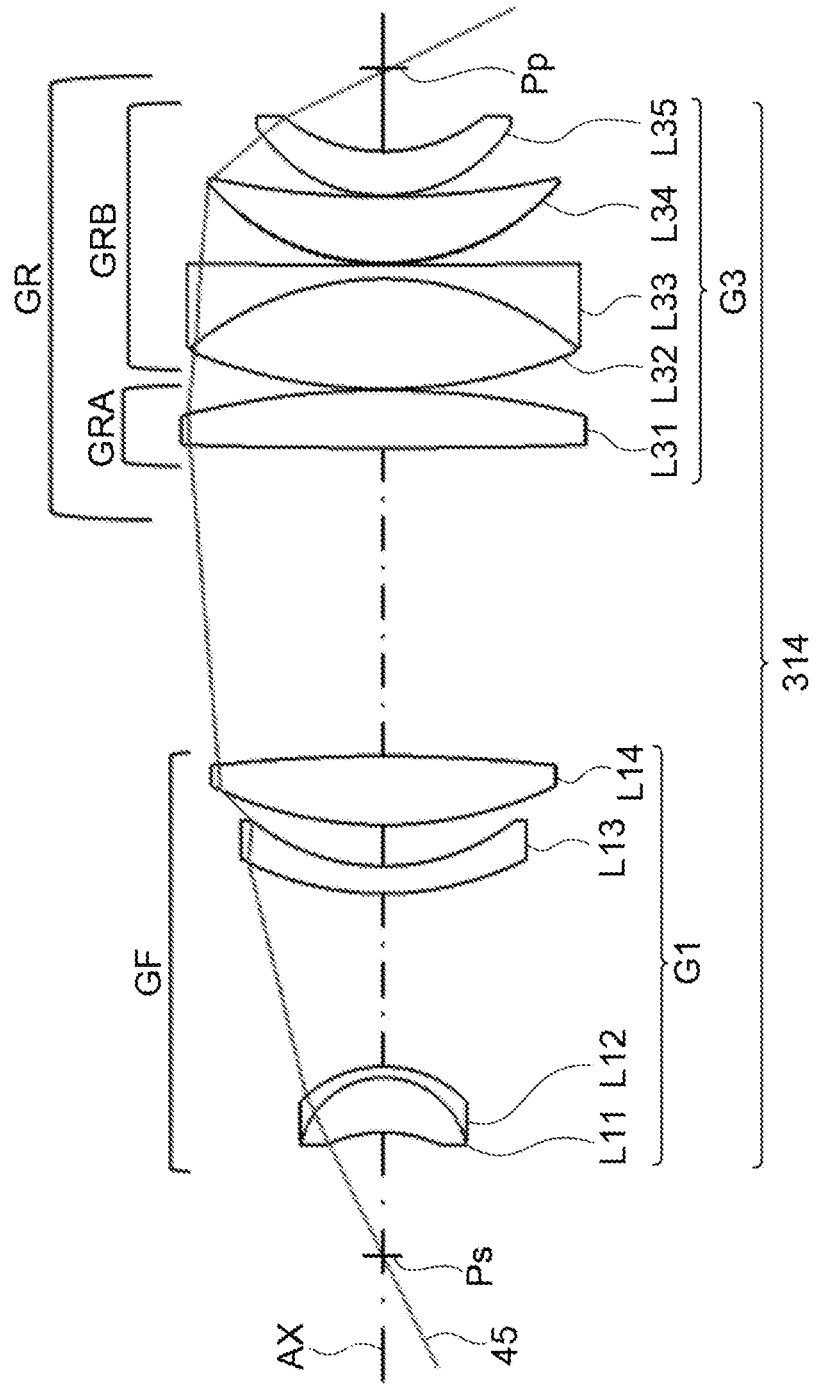
FIG. 31 is a drawing showing the configuration of an objective lens system according to a practical example 4-1.

The practical example 4-1 is an objective lens system 314 that assumes the SLO objective lens system. FIG. 31 shows the lens configuration of the objective lens system 314 according to the practical example 4-1. The objective lens system 314 includes, in the following order from the side of the scanner, a first lens group G1 and a third lens group G3. The first lens group G1 and the third lens group G3 are separated by a maximum air gap in the objective lens system 314.

The first lens group G1 includes a positive meniscus lens L11 having a concave surface facing the side of the scanner, a negative meniscus lens L12 having a concave surface facing the side of the scanner, a negative meniscus lens L13 having a convex surface facing the side of the scanner, and a positive lens L14. The lens L11 and the lens L12 are cemented to each other so as to form a meniscus-shaped lens component having a concave surface facing the side of the scanner. The third lens group G3 includes a positive lens L31, a biconvex positive lens L32, a negative lens L33 having a concave surface facing the side of the scanner, a positive meniscus lens L34 having a concave surface facing the side of the eye, and a positive meniscus lens L35 having a concave surface facing the side of the eye. The lens L32 and the lens L33 are cemented to each other so as to form a positive lens component. The positive meniscus lens L34 according to the practical example 4-1 is provided with a diffractive optical element (DOE for short) on a convex surface on the side of the scanner. Providing the diffractive optical element on the lens surface does not only facilitate correcting a chromatic aberration, but also utilizes refraction of the lens surface and diffraction of the diffractive optical element, thus allowing a reduction in the effective diameter of the lens. The diffractive optical element may be provided in another lens surface, and, for example, may be effectively provided in a lens having a large effective diameter, such as the lens L31, or the lens L11 or L12 that constitutes the nearest lens component to the scanner.

The objective lens system 314 can be regarded as consisting of the front group GF and the rear group GR described above. The front group GF corresponds to the first lens group G1, and the rear group GR corresponds to the third lens group G3. The A group GRA consists of the lens L31. The B group GRB consists of the lens L32, the lens L33, the lens L34, and the lens L35.

Table 13 lists lens data of the practical example 4-1.

TABLE 13

| surface number | radius | thickness | index | abbe number |
|---|---|---|---|---|
| 1 | ∞ | 45.00 | | |
| 2 | −50.839 | 20.00 | 1.6968 | 55.5 |
| 3 | −30.992 | 4.00 | 1.8052 | 25.5 |
| 4 | −42.597 | 62.93 | | |
| 5 | 114.445 | 10.00 | 1.8467 | 23.8 |
| 6 | 78.281 | 15.00 | | |
| 7 | 147.444 | 25.00 | 1.9108 | 35.3 |
| 8 | −597.164 | 112.16 | | |
| 9 | 2416.929 | 21.00 | 1.6400 | 60.2 |
| 10 | −300.000 | 0.50 | | |
| 11 | 190.000 | 40.00 | 1.7292 | 54.6 |
| 12 | −112.723 | 5.00 | 2.0010 | 29.1 |
| 13 | 3077.584 | 0.50 | | |
| (DOE) 14 | 85.566 | 24.00 | 2.0010 | 29.1 |
| 15 | 300.000 | 0.50 | | |
| 16 | 55.748 | 16.00 | 1.9537 | 32.3 |
| 17 | 60.000 | 30.00 | | |

In Table 13, (DOE) written in the "surface number" column indicates a surface having a diffractive optical element. The phase shape y of a diffractive surface is represented by the following equation:

$$\psi(h,m)=[2\pi/(m\times\lambda 0)]\times(C2\cdot h+C4\cdot h^4+C6\cdot h)$$

where, "h" represents a height in a direction orthogonal to the optical axis "m" represents a diffraction order of diffracted light, "λ0" represents a design wavelength, "C2" represents a second-order phase coefficient, "C4" represents a fourth-order phase coefficient, and "C6" represents a sixth-order phase coefficient.

Table 14 lists the phase coefficients of the diffractive surface according to the practical example 4-1. In Table 20, "E-n" (n is an integer) denotes "−10$^{-n}$".

TABLE 14

| surface number | 14 |
|---|---|
| m | 1 |
| C2 | −3.953E−04 |
| C4 | 0.000E+00 |
| C6 | 0.000E+00 |

Figure 32:
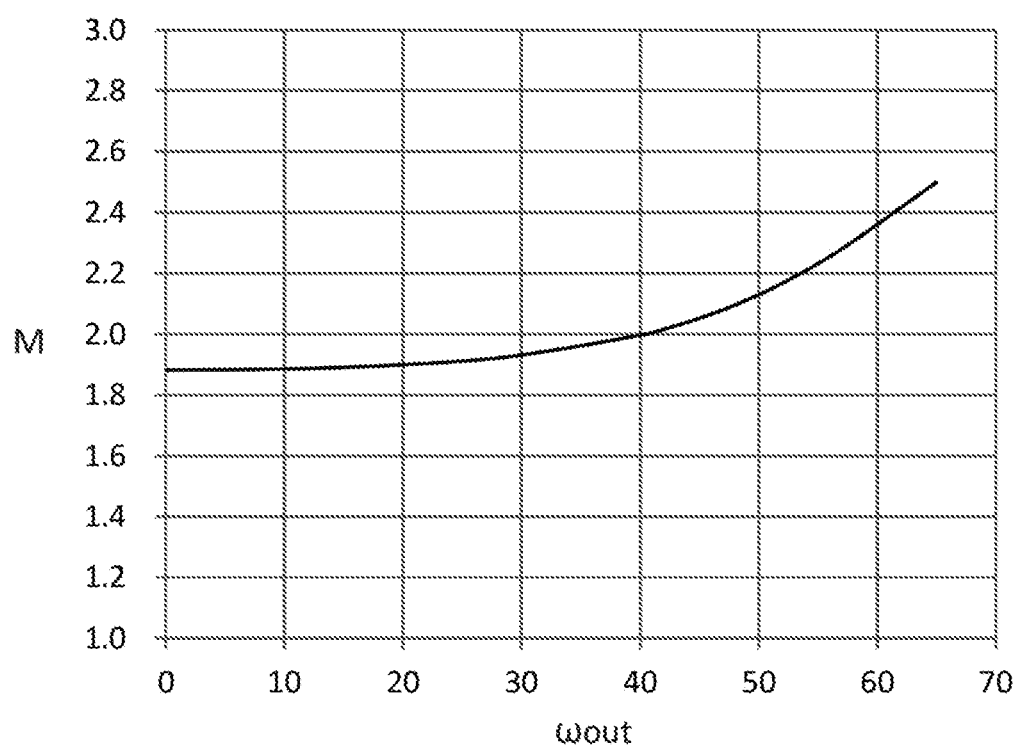
FIG. 32 is a graph showing the relationship between ωout and M in the objective lens system according to the practical example 4-1.
Figure 33:
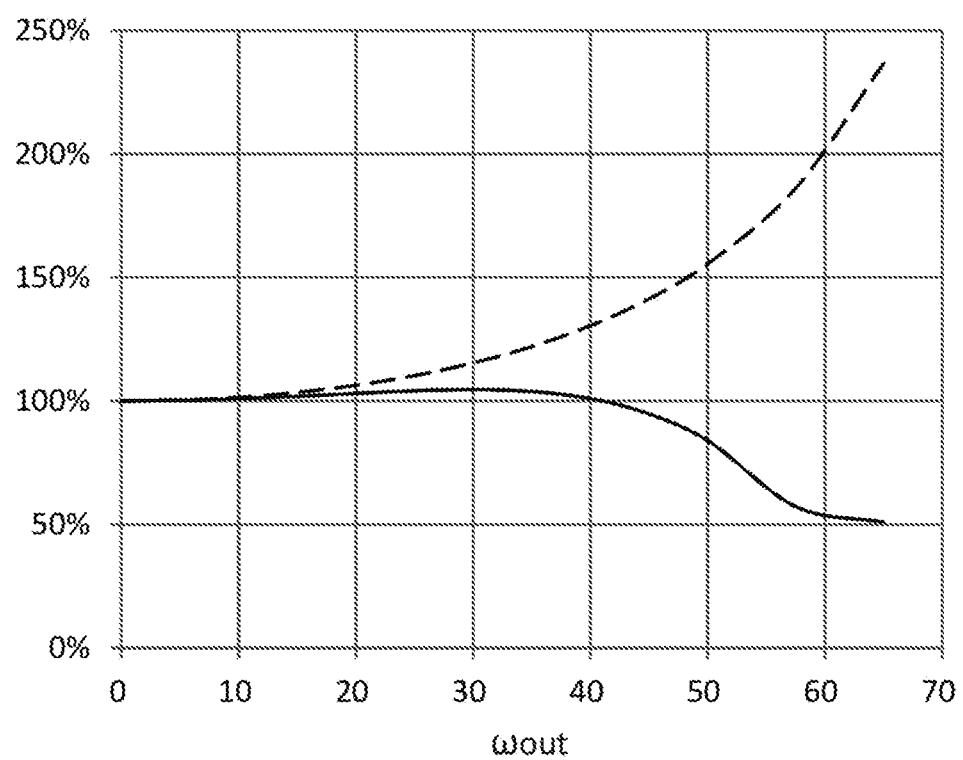
FIG. 33 is a graph showing the relationship between ωout and Pmax/Pmin in the objective lens system according to the practical example 4-1.

FIG. 32 shows the relationship between ωout and M according to the practical example 4-1. In FIG. 33, a solid line represents the relationship between ωout and Pmax/Pmin according to the practical example 4-1, and a broken line represents a curve of 1/cos(ωout). The practical example 4-1 is an SLO objective lens system having an external irradiation angle of 130 degrees, and it is apparent from FIGS. 32 and 33 that the practical example 4-1 has superior performance, as a UWF objective lens.

Practical Example 5-1

Figure 34:
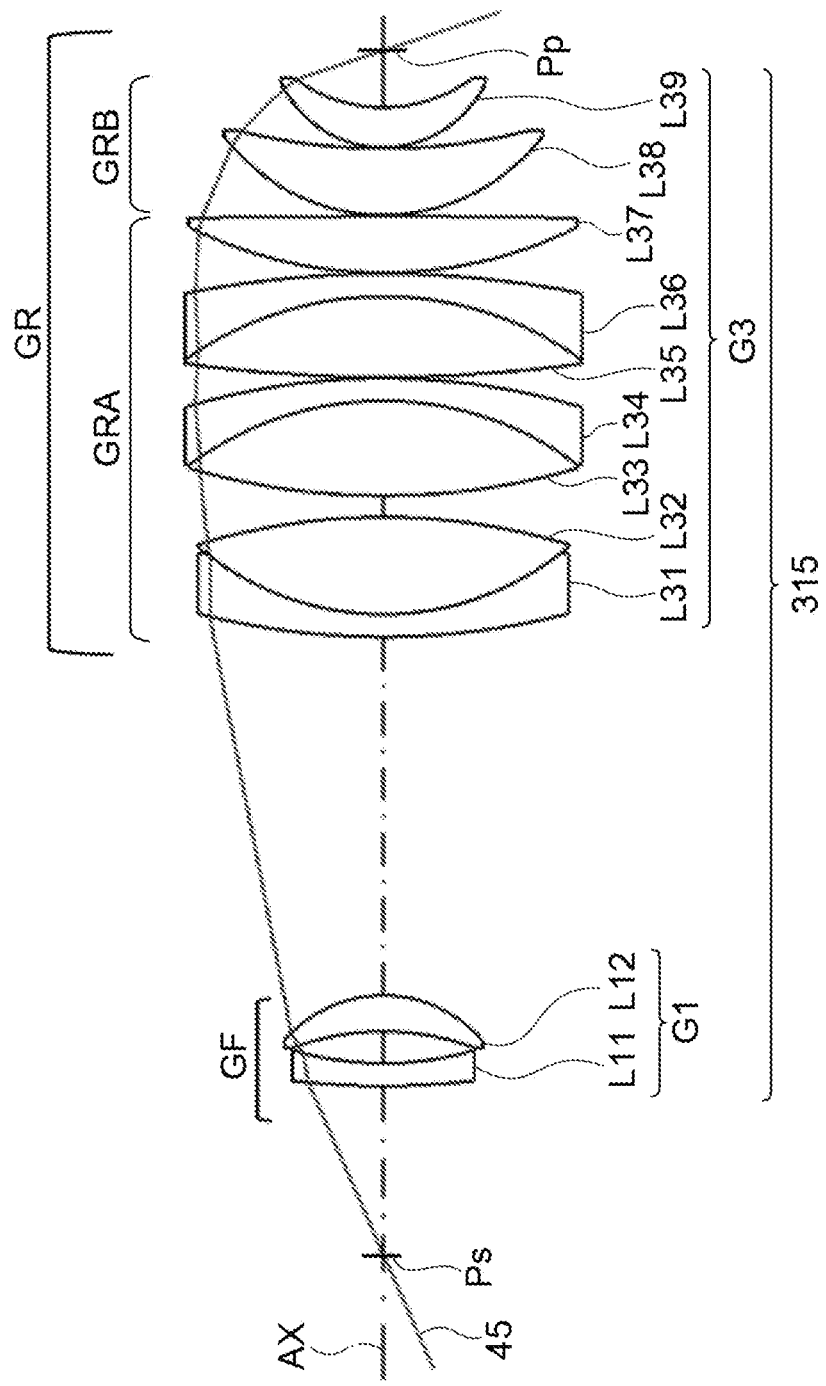
FIG. 34 is a drawing showing the configuration of an objective lens system according to a practical example 5-1.

The practical example 5-1 is an objective lens system 315 that assumes the SLO objective lens system. FIG. 34 shows the lens configuration of the objective lens system 315 according to the practical example 5-1. The objective lens system 315 includes, in the following order from the side of the scanner, a first lens group G1 and a third lens group G3. The first lens group G1 and the third lens group G3 are separated by a maximum air gap in the objective lens system 315.

The first lens group G1 includes a negative meniscus lens L11 having a convex surface facing the side of the scanner, and a positive meniscus lens L12 having a convex surface facing the side of the eye. The third lens group G3 includes a negative meniscus lens L31 having a convex surface facing the side of the scanner, a biconvex positive lens L32, a biconvex positive lens L33, a negative meniscus lens L34 having a convex surface facing the side of the eye, a biconvex positive lens L35, a negative meniscus lens L36 having a convex surface facing the side of the eye, a positive lens L37 having a convex surface facing the side of the scanner, a positive meniscus lens L38 having a concave surface facing the side of the eye, and a positive meniscus lens L39 having a concave surface facing the side of the eye. The lens L31 and the lens L32 are cemented to each other so as to form a biconvex positive lens component. The lens L33 and the lens L34 are cemented to each other so as to form a biconvex positive lens component. The lens L35 and the lens L36 are cemented to each other so as to form a biconvex positive lens component.

The objective lens system 315 can be regarded as consisting of the front group GF and the rear group GR described above. The front group GF corresponds to the first lens group G1, and the rear group GR corresponds to the third lens group G3. The A group GRA consists of the lens L31, the lens L32, the lens L33, the lens L34, the lens L35, the lens L36 and the lens L37. The B group GRB consists of the lens L38 and the lens L39.

Table 15 lists lens data of the practical example 5-1.

TABLE 15

| surface number | radius | thickness | index | abbe number |
|---|---|---|---|---|
| 1 | ∞ | 74.45 | | |
| 2 | 383.09 | 10.00 | 1.8467 | 23.8 |
| 3 | 148.22 | 14.08 | | |
| 4 | −119.89 | 16.00 | 1.9020 | 25.3 |
| 5 | −59.76 | 158.55 | | |
| 6 | 342.87 | 10.00 | 1.8467 | 23.8 |
| 7 | 131.43 | 43.00 | 1.5168 | 64.1 |
| 8 | −292.47 | 9.40 | | |
| 9 | 321.37 | 42.00 | 1.5168 | 64.1 |
| 10 | −149.01 | 10.00 | 1.8467 | 23.8 |
| 11 | −317.09 | 0.50 | | |
| 12 | 671.80 | 35.63 | 1.5168 | 64.1 |
| 13 | −156.43 | 10.00 | 1.8467 | 23.8 |
| 14 | −466.64 | 0.50 | | |
| 15 | 199.00 | 25.00 | 1.7292 | 54.6 |
| 16 | −4943.10 | 0.52 | | |
| 17 | 91.12 | 29.42 | 1.6031 | 60.7 |
| 18 | 274.29 | 0.50 | | |
| 19 | 51.49 | 17.71 | 1.9538 | 32.3 |
| 20 | 69.12 | 25.00 | | |

The qualitative trend of the relationship between ωout and M in the practical example 5-1 is similar to those of practical example 1-1 to the practical example 4-1. The qualitative trend of the relationship between out and Pmax/Pmin in the practical example 5-1 is similar to that in the practical example 3-1. Still, in the practical example 5-1, the value of Pmax/Pmin is 140% or less when ωout is 70 degrees.

Practical Example 6-1

Figure 35:
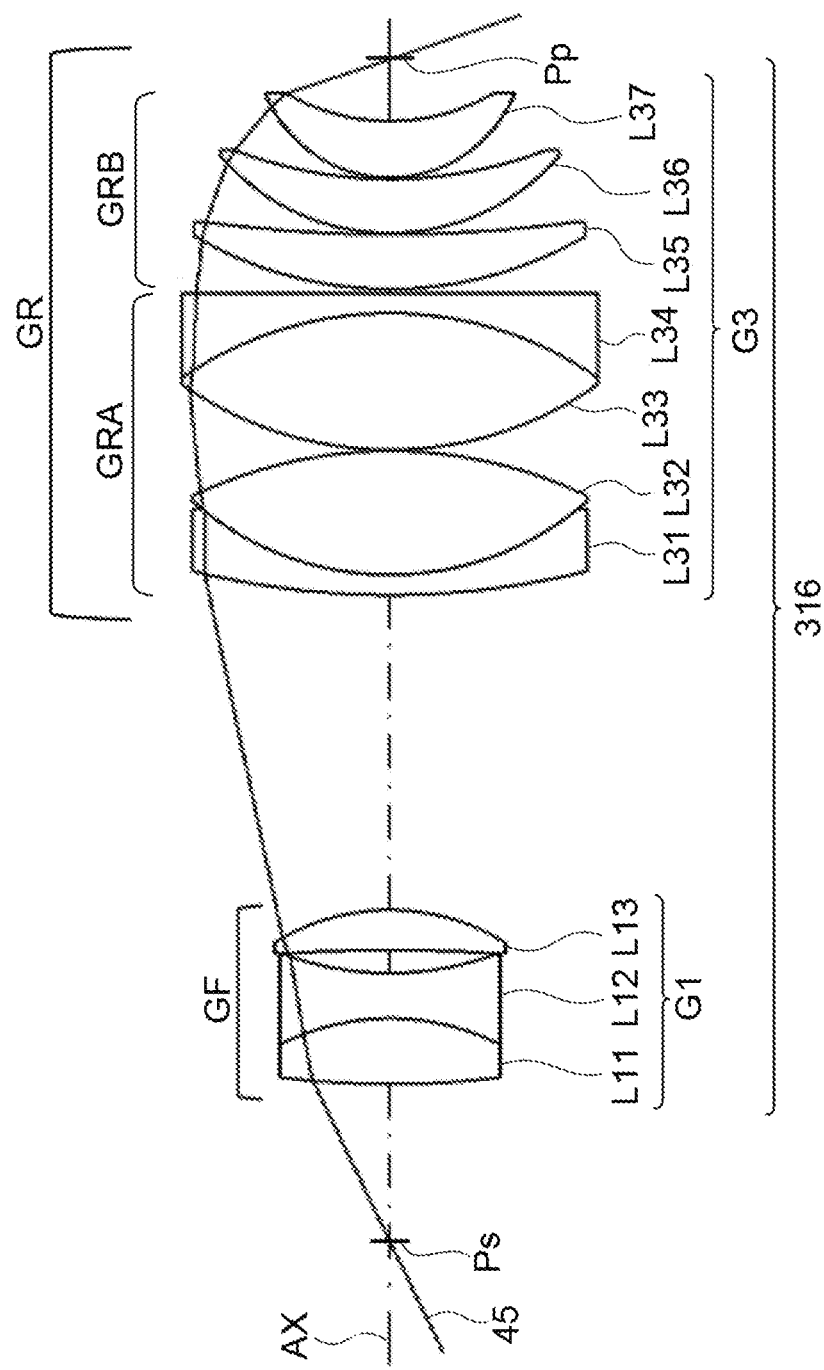
FIG. 35 is a drawing showing the configuration of an objective lens system according to a practical example 6-1.

The practical example 6-1 is an objective lens system 316 that assumes the SLO objective lens system. FIG. 35 shows the lens configuration of the objective lens system 316 according to the practical example 6-1. The objective lens system 316 includes, in the following order from the side of the scanner, a first lens group G1 and a third lens group G3. The first lens group G1 and the third lens group G3 are separated by a maximum air gap in the objective lens system 316.

The first lens group G1 includes a biconvex positive lens L11, a biconcave negative lens L12, and a positive meniscus lens L13 having a convex surface facing the side of the eye. The lens L11 and the lens L12 are cemented to each other so as to form a meniscus-shaped lens component having a convex surface facing the side of the scanner. The third lens group G3 includes a negative meniscus lens L31 having a convex surface facing the side of the scanner, a biconvex positive lens L32, a biconvex positive lens L33, a negative lens L34 having a concave surface facing the side of the scanner, a positive meniscus lens L35 having a concave surface facing the side of the eye, a positive meniscus lens L36 having a concave surface facing the side of the eye, and a positive meniscus lens L37 having a concave surface facing the side of the eye. The lens L31 and the lens L32 are cemented to each other so as to form a biconvex positive lens component. The lens L33 and the lens L34 are cemented to each other so as to form a biconvex positive lens component.

The objective lens system 316 can be regarded as consisting of the front group GF and the rear group GR described above. The front group GF corresponds to the first lens group G1, and the rear group GR corresponds to the third lens group G3. The A group GRA consists of the lens L31, the lens L32, the lens L33, and the lens L34. The B group GRB consists of the lens L35, the lens L36, and the lens L37.

Table 16 lists lens data of the practical example 6-1.

TABLE 16

| surface number | radius | thickness | index | abbe number |
|---|---|---|---|---|
| 1 | ∞ | 62.48 | | |
| 2 | 379.42 | 26.00 | 1.8348 | 42.7 |
| 3 | −100.76 | 18.00 | 1.6134 | 44.3 |
| 4 | 125.66 | 9.21 | | |
| 5 | −642.94 | 15.87 | 1.7725 | 49.6 |
| 6 | −90.17 | 125.00 | | |
| 7 | 338.00 | 8.00 | 1.8467 | 23.8 |
| 8 | 123.20 | 49.13 | 1.4970 | 81.6 |
| 9 | −187.72 | 0.50 | | |
| 10 | 148.72 | 54.24 | 1.5891 | 61.2 |
| 11 | −150.24 | 8.00 | 1.8467 | 23.8 |
| 12 | −29548.40 | 1.55 | | |
| 13 | 158.67 | 21.75 | 1.6584 | 50.9 |
| 14 | 574.91 | 0.50 | | |
| 15 | 92.05 | 21.47 | 1.7725 | 49.6 |
| 16 | 179.02 | 0.50 | | |
| 17 | 54.79 | 22.47 | 1.8919 | 37.1 |
| 18 | 85.00 | 25.00 | | |

The qualitative trend of the relationship between ωout and M in the practical example 6-1 is similar to those of practical example 1-1 to the practical example 4-1. The qualitative trend of the relationship between ωout and Pmax/Pmin in the practical example 6-1 is similar to that in the practical example 3-1. Still, in the practical example 6-1, the value of Pmax/Pmin is 140% or less when ωout is 70 degrees.

Practical Example 7-1

Figure 36:
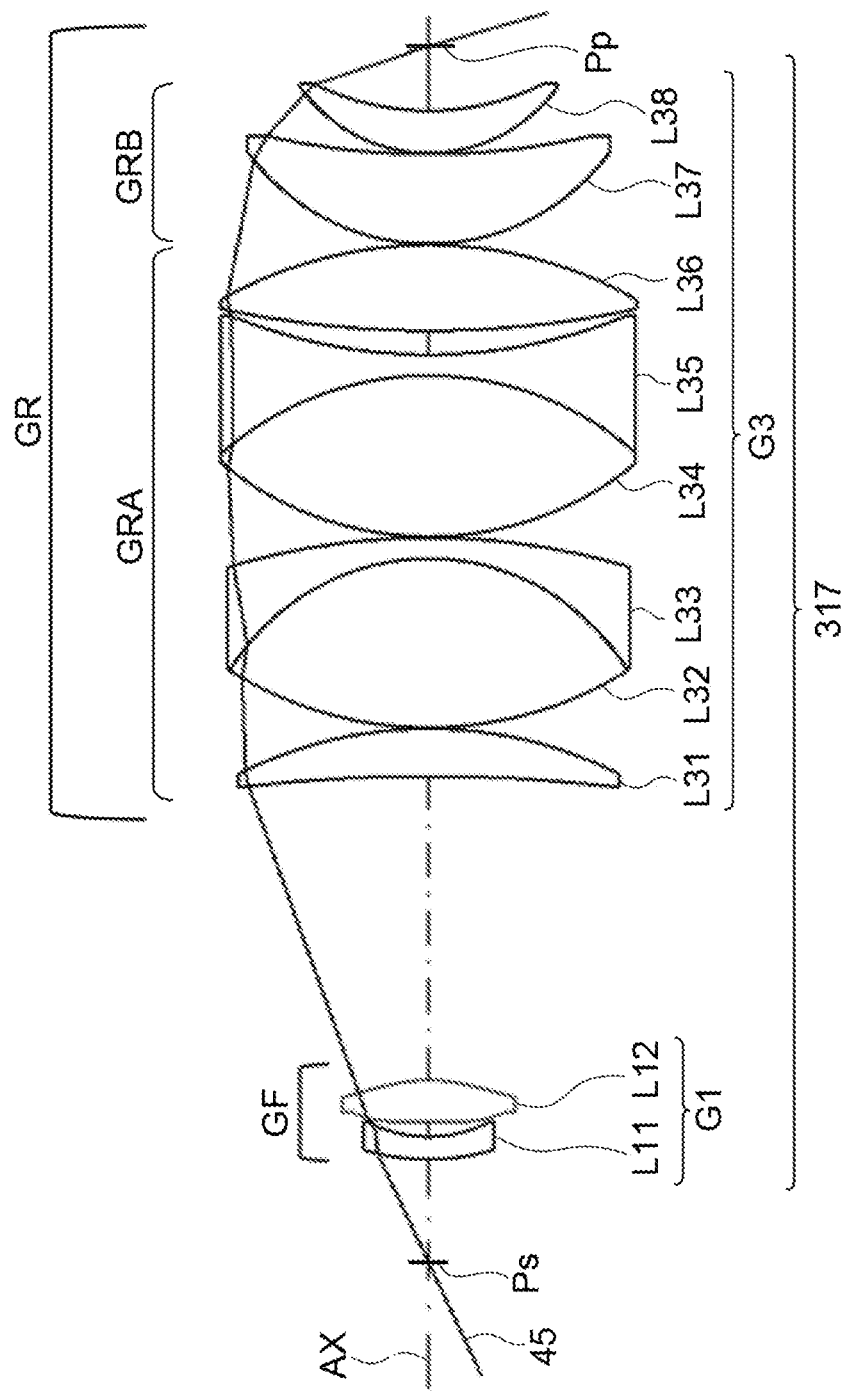
FIG. 36 is a drawing showing the configuration of an objective lens system according to a practical example 7-1.

The practical example 7-1 is an objective lens system 317 that assumes the SLO objective lens system. FIG. 36 shows the lens configuration of the objective lens system 317 according to the practical example 7-1 The objective lens system 317 includes, in the following order from the side of the scanner, a first lens group G1 and a third lens group G3. The first lens group G1 and the third lens group G3 are separated by a maximum air gap in the objective lens system 317.

The first lens group G1 includes a negative meniscus lens L1 having a convex surface facing the side of the scanner, and a positive lens L12 having a convex surface facing the side of the eye. The lens L12 has aspherical lens surfaces on the side of the scanner and on the side of the eye. The third lens group G3 includes a positive meniscus lens L31 having a convex surface facing the side of the eye, a biconvex positive lens L32, a negative meniscus lens L33 having a convex surface facing the side of the eye, a biconvex positive lens L34, a biconcave negative lens L35, a biconvex positive lens L36, a positive meniscus lens L37 having a concave surface facing the side of the eye, and a positive meniscus lens L38 having a concave surface facing the side of the eye. The lens L32 and the lens L33 are cemented to each other so as to form a biconvex positive lens component. The lens L34 and the lens L35 are cemented to each other so as to form a meniscus-shaped lens component having a concave surface facing the side of the eye.

The objective lens system 317 can be regarded as consisting of the front group GF and the rear group GR described above. The front group GF corresponds to the first lens group G1, and the rear group GR corresponds to the third lens group G3. The A group GRA consists of the lens L31, the lens L32, the lens L33, the lens L34, the lens L35, and the lens L36. The B group GRB consists of the lens L37 and the lens L38.

Table 17 lists lens data of the practical example 7-1.

TABLE 17

| surface number | radius | thickness | index | abbe number |
|---|---|---|---|---|
| 1 | ∞ | 44.38 | | |
| 2 | 100.92 | 9.71 | 1.8348 | 42.7 |
| 3 | 59.05 | 6.39 | | |
| (ASP) 4 | −451.46 | 17.92 | 1.5829 | 59.5 |
| (ASP) 5 | −65.79 | 130.59 | | |
| 6 | −732.63 | 20.50 | 1.9020 | 25.3 |
| 7 | −187.14 | 0.50 | | |
| 8 | 167.46 | 72.54 | 1.5168 | 64.1 |
| 9 | −103.18 | 9.00 | 2.0006 | 25.5 |
| 10 | −311.18 | 0.50 | | |
| 11 | 145.98 | 69.14 | 1.4875 | 70.3 |
| 12 | −140.05 | 9.00 | 1.8467 | 23.8 |
| 13 | 232.19 | 10.27 | | |
| 14 | 444.03 | 36.86 | 1.7725 | 49.6 |
| 15 | −187.67 | 0.50 | | |
| 16 | 99.59 | 38.52 | 1.7550 | 52.3 |
| 17 | 323.97 | 0.50 | | |
| 18 | 70.25 | 18.20 | 2.0006 | 25.5 |
| 19 | 115.41 | 25.00 | | |

Table 18 lists the aspherical-surface coefficients of the aspherical surface according to the practical example 7-1.

TABLE 18

| surface number | 4 | 5 |
|---|---|---|
| Conic Constant | −8.379 | 0.919 |
| 4th Order Coefficient | 5.655E−06 | 2.337E−06 |
| 6th Order Coefficient | −6.421E−10 | 1.232E−09 |
| 8th Order Coefficient | −6.145E−13 | −5.666E−13 |
| 10th Order Coefficient | 0.000E+00 | 0.000E+00 |

The qualitative trend of the relationship between ωout and M in the practical example 7-1 is similar to those of practical example 1-1 to the practical example 4-1. The qualitative trend of the relationship between ωout and Pmax/Pmin in the practical example 7-1 is similar to that in the practical example 1-1.

Practical Example 8-1

Figure 37:
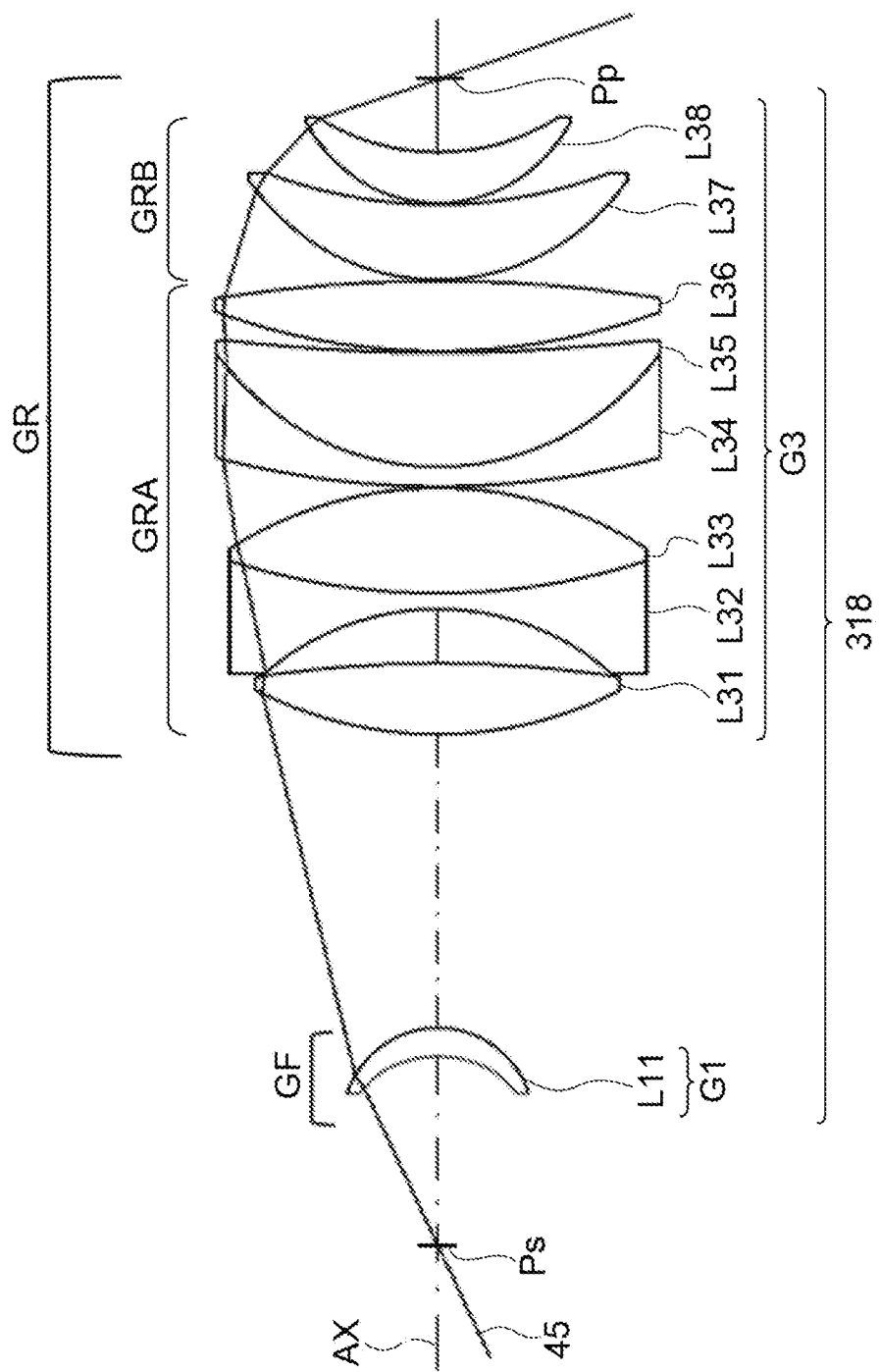
FIG. 37 is a drawing showing the configuration of an objective lens system according to a practical example 8-1.

The practical example 8-1 is an objective lens system 318 that assumes the SLO objective lens system. FIG. 37 shows the lens configuration of the objective lens system 318 according to the practical example 8-1. The objective lens system 318 includes, in the following order from the side of the scanner, a first lens group G1 and a third lens group G3. The first lens group G1 and the third lens group G3 are separated by a maximum air gap in the objective lens system 318.

The first lens group G1 includes a positive meniscus lens L11 having a concave surface facing the side of the scanner. The lens L11 has an aspherical lens surface on the side of the scanner. The third lens group G3 includes a biconvex positive lens L31, a biconcave negative lens L32, a biconvex positive lens L33, a negative meniscus lens L34 having a concave surface facing the side of the eye, a positive meniscus lens L35 having a concave surface facing the side of the eye, a biconvex positive lens L36, a positive meniscus lens L37 having a concave surface facing the side of the eye, and a positive meniscus lens L38 having a concave surface facing the side of the eye. The lens L32 and the lens L33 are cemented to each other so as to form a meniscus-shaped lens component having a convex surface facing the side of the eye. The lens L34 and the lens L35 are cemented to each other so as to form a meniscus-shaped lens component having a concave surface facing the side of the eye.

The objective lens system 318 can be regarded as consisting of the front group GF and the rear group GR described above. The front group GF corresponds to the first lens group G1, and the rear group GR corresponds to the third lens group G3. The A group GRA consists of the lens L31, the lens L32, the lens L33, the lens L34, the lens L35, and the lens L36. The B group GRB consists of the lens L37 and the lens L38.

Table 19 lists lens data of the practical example 8-1.

TABLE 19

| surface number | radius | thickness | index | abbe number |
|---|---|---|---|---|
| 1 | ∞ | 64.90 | | |
| (ASP) 2 | −41.48 | 9.84 | 1.8511 | 40.1 |
| 3 | −33.72 | 100.67 | | |
| 4 | 141.02 | 24.29 | 1.9027 | 35.7 |
| 5 | −432.22 | 18.65 | | |
| 6 | −93.96 | 5.41 | 1.8467 | 23.8 |
| 7 | 243.13 | 36.12 | 1.5891 | 61.2 |
| 8 | −137.28 | 0.50 | | |
| 9 | 309.35 | 6.75 | 1.8467 | 23.8 |
| 10 | 96.71 | 39.18 | 1.7880 | 47.4 |

TABLE 19-continued

| surface number | radius | thickness | index | abbe number |
|---|---|---|---|---|
| 11 | 654.71 | 0.50 | | |
| 12 | 230.36 | 23.97 | 1.7880 | 47.4 |
| 13 | −513.61 | 0.50 | | |
| 14 | 81.33 | 25.77 | 1.7880 | 47.4 |
| 15 | 170.18 | 0.50 | | |
| 16 | 52.12 | 17.45 | 1.9027 | 35.7 |
| 17 | 80.00 | 25.00 | | |

Table 20 lists the aspherical-surface coefficients of the aspherical surface according to the practical example 8-1.

TABLE 20

| surface number | 2 |
|---|---|
| Conic Constant | 0.42 |
| 4th Order Coefficient | 0.000E+00 |
| 6th Order Coefficient | −8.657E−09 |
| 8th Order Coefficient | 1.354E−11 |
| 10th Order Coefficient | −8.907E−15 |

The qualitative trend of the relationship between ωout and M in the practical example 8-1 is similar to those of practical example 1-1 to the practical example 4-1. The qualitative trend of the relationship between ωout and Pmax/Pmin in the practical example 8-1 is similar to those of practical example 1-1 to the practical example 2-2.

Practical Example 9-1

Figure 38:
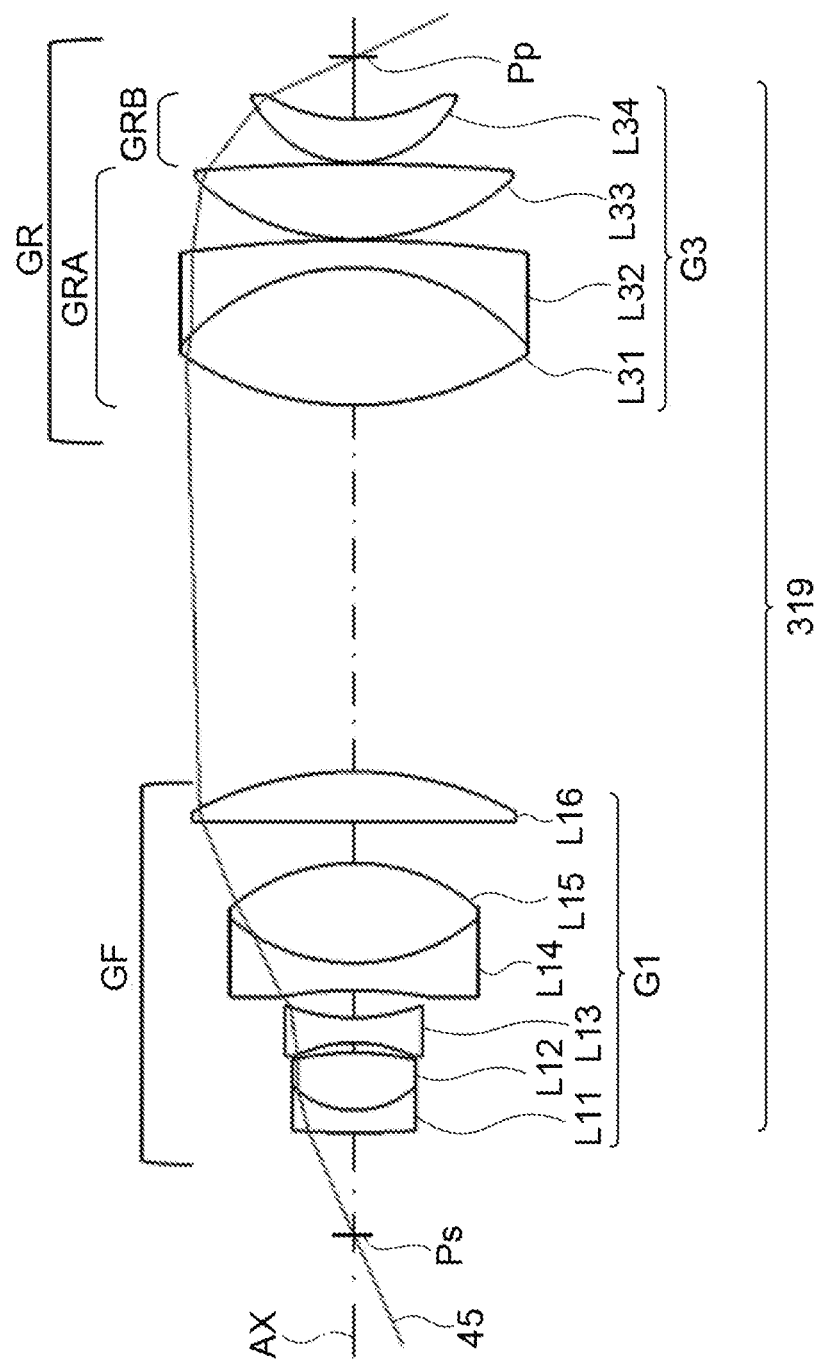
FIG. 38 is a drawing showing the configuration of an objective lens system according to a practical example 9-1.

The practical example 9-1 is an objective lens system 319 that assumes the SLO objective lens system. FIG. 38 shows the lens configuration of the objective lens system 319 according to the practical example 9-1. The objective lens system 319 includes, in the following order from the side of the scanner, a first lens group G1 and a third lens group G3. The first lens group G1 and the third lens group G3 are separated by a maximum air gap in the objective lens system 319.

The first lens group G1 includes a negative meniscus lens L11 having a convex surface facing the side of the scanner, a biconvex positive lens L12, a biconcave negative lens L13, a biconcave negative lens L14 a biconvex positive lens L15, and a positive lens L16 having a convex surface facing the side of the eye. The lens L11 and the lens L12 are cemented to each other so as to form a biconvex lens component. The lens L14 and the lens L15 are cemented to each other so as to form a meniscus-shaped lens component having a convex surface facing the side of the eye. The third lens group G3 includes a biconvex positive lens L31, a negative meniscus lens L32 having a convex surface facing the side of the eye, a biconvex positive lens L33, and a positive meniscus lens L34 having a concave surface facing the side of the eye. The lens L31 and the lens l32 are cemented to each other so as to form a biconvex positive lens component.

The objective lens system 319 can be regarded as consisting of the front group GF and the rear group GR described above. The front group GF corresponds to the first lens group G1, and the rear group GR corresponds to the third lens group G3. The A group GRA consists of the lens L31, the lens L32, and the lens L33. The B group GRB consists of the lens L34.

Table 21 lists lens data of the practical example 9-1.

TABLE 21

| surface number | radius | thickness | index | abbe number |
|---|---|---|---|---|
| 1 | ∞ | 40.76 | | |
| 2 | 326.99 | 9.00 | 1.4875 | 70.3 |
| 3 | 37.08 | 23.00 | 1.8467 | 23.8 |
| 4 | −117.47 | 4.05 | | |
| 5 | −55.03 | 10.00 | 1.8467 | 23.8 |
| 6 | 79.18 | 10.90 | | |
| 7 | −182.04 | 11.00 | 1.8467 | 23.8 |
| 8 | 78.91 | 40.00 | 1.7725 | 49.6 |
| 9 | −78.91 | 16.58 | | |
| 10 | 1.00E+18 | 20.00 | 1.7550 | 52.3 |
| 11 | −140.87 | 146.71 | | |
| 12 | 130.04 | 55.00 | 1.5891 | 61.2 |
| 13 | −94.10 | 11.00 | 1.8467 | 23.8 |
| 14 | −484.46 | 0.50 | | |
| 15 | 97.43 | 30.10 | 1.6030 | 65.4 |
| 16 | −738.15 | 0.50 | | |
| 17 | 46.43 | 17.30 | 1.8830 | 40.7 |
| 18 | 70.03 | 25.00 | | |

The qualitative trend of the relationship between ωout and M in the practical example 9-1 is similar to those of practical example 1-1 to the practical example 4-1. The qualitative trend of the relationship between ωout and Pmax/Pmin in the practical example 9-1 is similar to that in the practical example 1-1.

Practical Example 10-1

Figure 39:
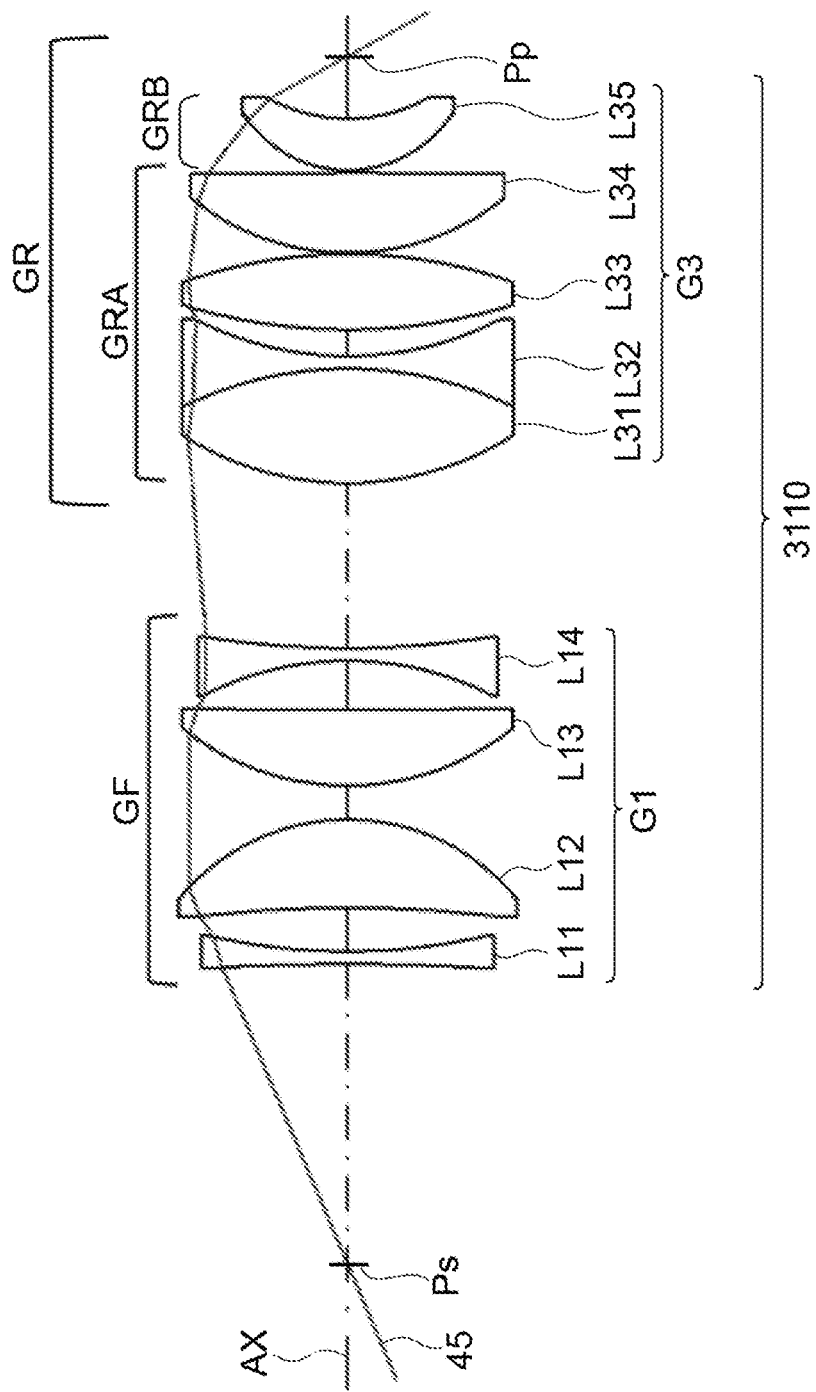
FIG. 39 is a drawing showing the configuration of an objective lens system according to a practical example 10-1.

The practical example 10-1 is an objective lens system 3110 that assumes the SLO objective lens system. FIG. 39 shows the lens configuration of the objective lens system 3110 according to the practical example 10-1. The objective lens system 3110 includes, in the following order from the side of the scanner, a first lens group G1 and a third lens group G3. The first lens group G1 and the third lens group G3 are separated by a maximum air gap in the objective lens system 3110.

The first lens group G1 includes a biconcave negative lens L11, a positive meniscus lens L12 having a convex surface facing the side of the eye, a positive meniscus lens L13 having a convex surface facing the side of the scanner, and a biconcave negative lens L4. The third lens group G3 includes a biconvex positive lens L31, a biconcave negative lens L32, a biconvex positive lens L33, a positive lens L34 having a convex surface facing the side of the scanner, and a positive meniscus lens L35 having a concave surface facing the side of the eye. The lens L31 and the lens L32 are cemented to each other so as to form a meniscus-shaped lens component.

The objective lens system 3110 can be regarded as consisting of the front group GF and the rear group GR described above. The front group GF corresponds to the first lens group G1, and the rear group GR corresponds to the third lens group G3. The A group GRA consists of the lens L31, the lens L32, the lens L33, and the lens L34. The B group GRB consists of the lens L35.

Table 22 lists lens data of the practical example 10-1.

TABLE 22

| surface number | radius | thickness | index | abbe number |
|---|---|---|---|---|
| 1 | ∞ | 119.18 | | |
| 2 | −970.44 | 5.00 | 1.4875 | 70.3 |
| 3 | 255.21 | 17.38 | | |

TABLE 22-continued

| surface number | radius | thickness | index | abbe number |
|---|---|---|---|---|
| 4 | −515.36 | 35.00 | 1.7550 | 52.3 |
| 5 | −89.83 | 13.46 | | |
| 6 | 109.15 | 30.00 | 1.7550 | 52.3 |
| 7 | 3238.08 | 19.60 | | |
| 8 | −130.77 | 5.00 | 1.7847 | 25.6 |
| 9 | 379.99 | 65.50 | | |
| 10 | 126.87 | 45.42 | 1.4970 | 81.7 |
| 11 | −155.12 | 5.00 | 1.7847 | 25.6 |
| 12 | 137.37 | 10.51 | | |
| 13 | 231.94 | 30.00 | 1.7550 | 52.3 |
| 14 | −205.63 | 0.50 | | |
| 15 | 102.97 | 31.73 | 1.7550 | 52.3 |
| 16 | −6066.30 | 1.08 | | |
| 17 | 51.24 | 20.44 | 1.9538 | 32.3 |
| 18 | 67.63 | 25.00 | | |

The qualitative trend of the relationship between ωout and M in the practical example 10-1 is similar to those of practical example 1-1 to the practical example 4-1. The qualitative trend of the relationship between ωout and Pmax/Pmin in the practical example 10-1 is similar to that in the practical example 1-1.

Practical Example 11-1

Figure 40:
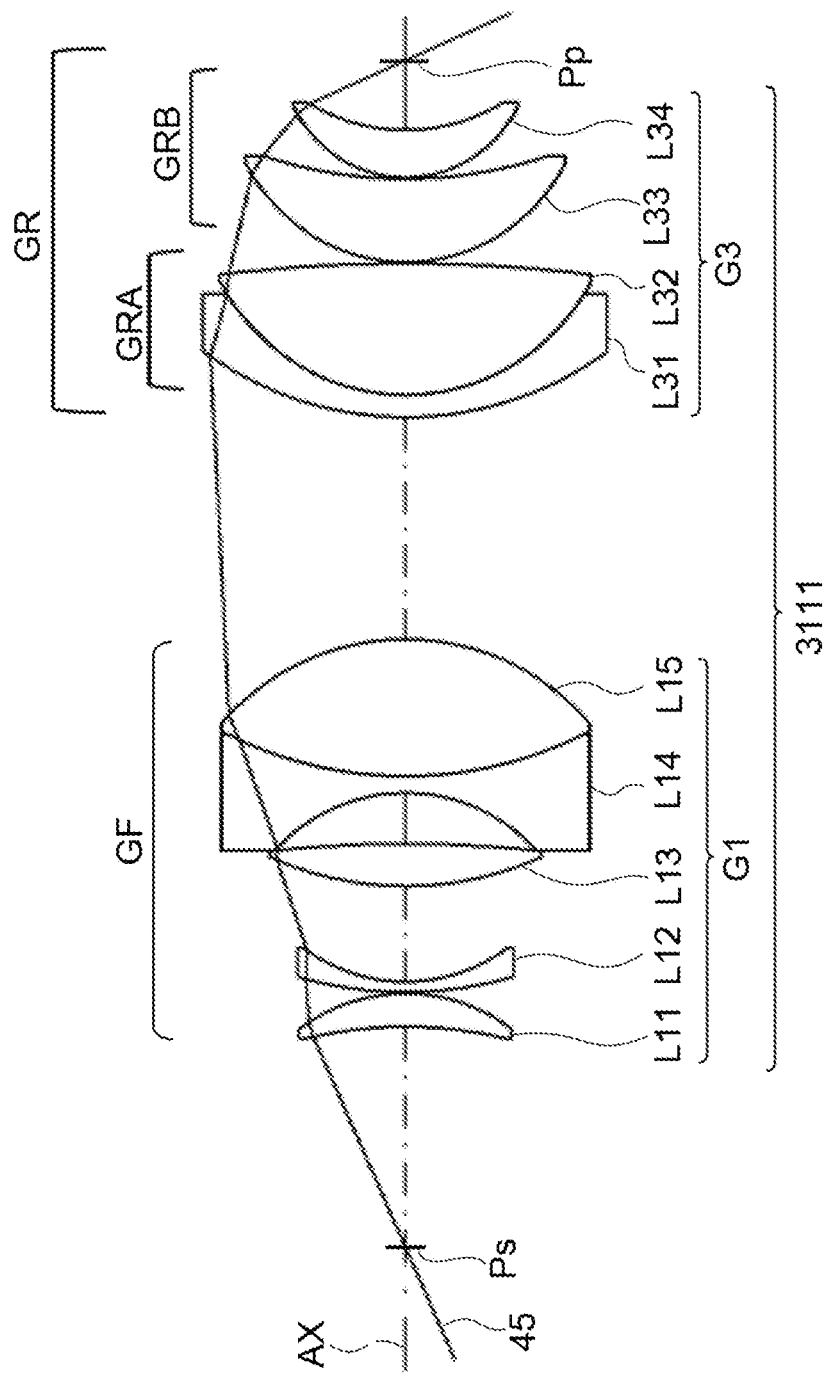
FIG. 40 is a drawing showing the configuration of an objective lens system according to a practical example 11-1.

The practical example 11-1 is an objective lens system 3111 that assumes the SLO objective lens system. FIG. 40 shows the lens configuration of the objective lens system 3111 according to the practical example 11-1. The objective lens system 3111 includes, in the following order from the side of the scanner, a first lens group G1 and a third lens group G3. The first lens group G1 and the third lens group G3 are separated by a maximum air gap in the objective lens system 3111.

The first lens group G1 includes a positive meniscus lens L11 having a convex surface facing the side of the eye, a negative meniscus lens L12 having a convex surface facing the side of the scanner, a positive lens L13 having a convex surface facing the side of the scanner, a biconcave negative lens L14, and a biconvex positive lens L5. The lens L14 and the lens L15 are cemented to each other so as to form a meniscus-shaped lens component. The third lens group G3 includes a negative meniscus lens L31 having a convex surface facing the side of the scanner, a biconvex positive lens L32, a positive meniscus lens L33 having a concave surface facing the side of the eye, and a positive meniscus lens L34 having a concave surface facing the side of the eye. The lens L31 and the lens L32 are cemented to each other so as to form a biconvex positive lens component.

The objective lens system 3111 can be regarded as consisting of the front group GF and the rear group GR described above. The front group GF corresponds to the first lens group G1, and the rear group GR corresponds to the third lens group G3. The A group GRA consists of the lens L31 and the lens L32. The B group GRB consists of the lens L33 and the lens L34.

Table 23 lists lens data of the practical example 11-1.

TABLE 23

| surface number | radius | thickness | index | abbe number |
|---|---|---|---|---|
| 1 | ∞ | 79.39 | | |
| 2 | −160.34 | 12.00 | 1.9500 | 29.4 |
| 3 | −65.43 | 0.50 | | |
| 4 | 142.92 | 3.77 | 1.5168 | 64.1 |
| 5 | 63.37 | 34.38 | | |
| 6 | 122.44 | 15.29 | 1.8348 | 42.7 |
| 7 | −470.86 | 18.36 | | |
| 8 | −65.69 | 6.00 | 1.8467 | 23.8 |
| 9 | 148.63 | 49.36 | 1.7440 | 44.9 |
| 10 | −90.40 | 80.00 | | |
| 11 | 127.50 | 8.00 | 1.8467 | 23.8 |
| 12 | 77.08 | 47.36 | 1.5891 | 61.2 |
| 13 | −576.12 | 0.50 | | |
| 14 | 65.96 | 30.00 | 1.5891 | 61.2 |
| 15 | 168.50 | 0.50 | | |
| 16 | 45.91 | 17.05 | 1.8348 | 42.7 |
| 17 | 69.38 | 25.00 | | |

The qualitative trend of the relationship between ωout and M in the practical example 11-1 is similar to those of practical example 1-1 to the practical example 4-1. The qualitative trend of the relationship between ωout and Pmax/Pmin in the practical example 11-1 is similar to that in the practical example 1-1.

Table 24 to Table 27 show corresponding values of the conditional expressions in practical examples. In Table 27, the minimum values of fAp/fR of practical examples are shown in the column fAp/fR (min), and the maximum values of fAp/fR of practical examples are shown in the column fAp/fR (max).

TABLE 24

| | | |M1| | |M2| | |β1| | |β2| |
|---|---|---|---|---|---|
| practical example 1 | practical example 1-1 | 1.85 | — | 0.54 | — |
| | practical example 1-2 | — | 2.57 | — | 0.39 |
| practical example 2 | practical example 2-1 | 2.05 | — | 0.49 | — |
| | practical example 2-2 | — | 2.81 | — | 0.36 |
| practical example 3 | practical example 3-1 | 2.38 | — | 0.42 | — |
| | practical example 3-2 | — | 3.27 | — | 0.31 |

TABLE 25

| | maximum value of ωin | maximum value of ωout (ωmax) | Mpar | Mmax | Mmax/Mpar |
|---|---|---|---|---|---|
| practical example 1-1 | 26.40 | 65.70 | 1.85 | 2.49 | 1.35 |
| practical example 1-2 | 18.86 | 63.76 | 2.57 | 3.38 | 1.32 |
| practical example 2-1 | 26.40 | 72.02 | 2.05 | 2.73 | 1.33 |
| practical example 2-2 | 18.86 | 71.99 | 2.81 | 3.82 | 1.36 |
| practical example 3-1 | 26.40 | 72.01 | 2.38 | 2.73 | 1.15 |
| practical example 3-2 | 18.86 | 71.99 | 3.27 | 3.82 | 1.17 |
| practical example 4-1 | 26.00 | 65.00 | 1.88 | 2.50 | 1.33 |
| practical example 5-1 | 24 | 72.01 | 2.56 | 3 | 1.17 |
| practical example 6-1 | 26 | 72 | 2.35 | 2.77 | 1.18 |

TABLE 25-continued

| | maximum value of ωin | maximum value of ωout (ωmax) | Mpar | Mmax | Mmax/Mpar |
|---|---|---|---|---|---|
| practical example 7-1 | 25.44 | 71.87 | 2.03 | 2.83 | 1.39 |
| practical example 8-1 | 25.5 | 72 | 1.94 | 2.82 | 1.45 |
| practical example 9-1 | 24 | 65.95 | 2.19 | 2.75 | 1.26 |
| practical example 10-1 | 23.3 | 62 | 2.13 | 2.66 | 1.25 |
| practical example 11-1 | 24 | 66 | 2.03 | 2.75 | 1.32 |

TABLE 26

| | Pmin | Pmax | Pmax/Pmin | 0.7/cos(ωmax) |
|---|---|---|---|---|
| practical example 1-1 | 0.95 | 0.64 | 0.68 | 1.70 |
| practical example 1-2 | 3.41 | 2.38 | 0.70 | 1.58 |
| practical example 2-1 | 0.85 | 0.63 | 0.74 | 2.27 |
| practical example 2-2 | 3.11 | 2.65 | 0.85 | 2.26 |
| practical example 3-1 | 2.63 | 4.74 | 1.81 | 2.27 |
| practical example 3-2 | 2.72 | 3.45 | 1.27 | 2.26 |
| practical example 4-1 | 1.06 | 0.54 | 0.51 | 1.66 |
| practical example 5-1 | 0.4 | 0.5 | 1.25 | 2.27 |
| practical example 6-1 | 0.4 | 0.51 | 1.28 | 2.27 |
| practical example 7-1 | 0.49 | 0.27 | 0.55 | 2.25 |
| practical example 8-1 | 0.41 | 0.29 | 0.71 | 2.27 |
| practical example 9-1 | 0.56 | 0.42 | 0.75 | 1.72 |
| practical example 10-1 | 0.56 | 0.45 | 0.80 | 1.49 |
| practical example 11-1 | 0.56 | 0.36 | 0.64 | 1.72 |

TABLE 27

| | TL/f | fF/fR | D/TL | fB/fR | fAp/fR (min) | fAp/fR (max) |
|---|---|---|---|---|---|---|
| practical example 1-1 | −0.02 | 1.82 | 0.42 | 1.16 | 1.94 | 1.94 |
| practical example 1-2 | 0.02 | 2.57 | 0.41 | 1.16 | 1.94 | 1.94 |
| practical example 2-1 | 0.06 | 2.06 | 0.32 | 1.75 | 1.54 | 1.54 |
| practical example 2-2 | −0.38 | 2.73 | 0.34 | 1.75 | 1.54 | 1.54 |
| practical example 3-1 | −0.74 | 2.08 | 0.33 | 1.82 | 2.66 | 2.66 |
| practical example 3-2 | −0.05 | 3.20 | 0.30 | 1.82 | 2.66 | 2.66 |
| practical example 4-1 | 0.41 | 1.89 | 0.31 | 1.14 | — | — |
| practical example 5-1 | −0.50 | 2.52 | 0.37 | 1.28 | 2.66 | 3.64 |
| practical example 6-1 | 0.01 | 2.35 | 0.33 | 1.07 | 2.14 | 2.49 |
| practical example 7-1 | 0.90 | 2.54 | 0.29 | 0.63 | 1.00 | 1.17 |
| practical example 8-1 | −0.05 | 1.93 | 0.32 | 1.11 | 2.03 | 2.24 |
| practical example 9-1 | −0.14 | 2.20 | 0.31 | 1.86 | 1.64 | 1.64 |
| practical example 10-1 | −0.09 | 2.13 | 0.19 | 2.30 | 2.50 | 2.50 |
| practical example 11-1 | 0.10 | 2.50 | 0.25 | 0.46 | 1.14 | 1.14 |

Each practical example described above provides a UWF optical system with the external irradiation angle exceeding 120 degrees. As what is known as a working distance, the axial distance between the nearest lens surface to the eye and the pupil plane Pp of 25 mm or more is secured. It is important to set the value of the working distance to be large for the practical use of the ophthalmic device including the UWF optical system. However, the effective diameter of the objective lens sharply increases as the working distance increases. Thus, the working distance of the UWF optical system is practically set to be 20 mm or more and preferably 22 mm or more. A larger upper limit value of the working distance results in a smaller load on the subject. Still, for the sake of performance, cost, and easy of manufacturing of the optical system, the upper limit should be 42 mm <Another Embodiment Using Relay System>

Figure 41:
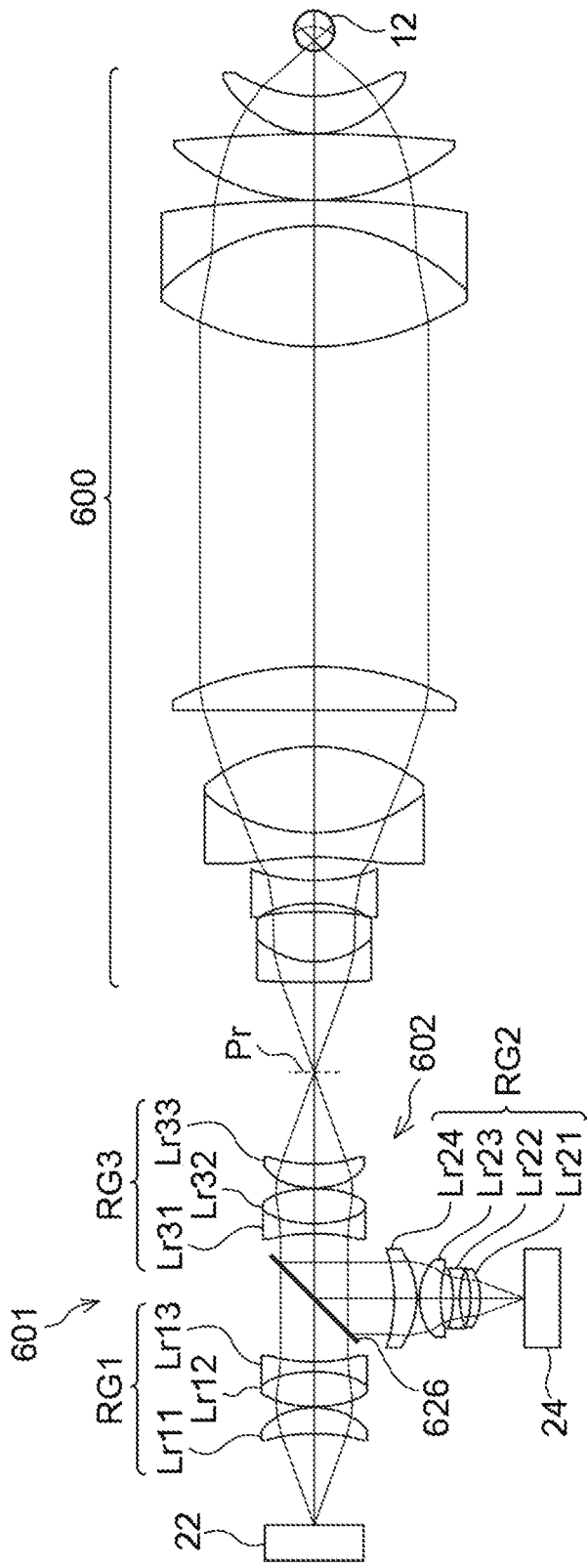
FIG. 41 is a cross-sectional view showing the configuration of an imaging optical system according to another embodiment.

Next, an imaging optical system according to another embodiment will be described. FIG. 41 shows across-sectional view of a configuration of an imaging optical system according to another embodiment. The imaging optical system shown in FIG. 41 is largely different from the example shown in FIG. 3 in that an optical system for relay is provided. The imaging optical system shown in FIG. 41 includes a first relay system 601 and an objective lens system 600 on the optical path between the first optical scanner 22 and the eye 12, and includes a second relay system 602 and an objective lens system 600 on the optical path between the second optical scanner 24 and the eye 12. The first relay system 601 includes, in the following order from the side of the first optical scanner 22, a first sub lens group RG1 and a common sub lens group RG3. The second relay system 602 includes, in the following order from the side of the second optical scanner 24, a second sub lens group RG2 and a common sub lens group RG3.

The imaging optical system shown in FIG. 41 includes a beam combiner 626 having a function similar to that of the beam combiner 26 shown in FIG. 3. The beam combiner 626 is disposed between the first sub lens group RG1 and the common sub lens group RG3, and is disposed between the second sub lens group RG2 and the common sub lens group RG3. A configuration supporting the combiner 626 with incident angle dependence is provided, with scanning light beam passing through the first sub lens group RG1 and the common sub lens group RG3 being parallel light and with scanning light beam passing through the second sub lens group RG2 and the common sub lens group RG3 also being parallel light.

In the example shown in FIG. 41, the common lens group consists of the common sub lens group RG3 and the objective lens system 600. The light used for an angular scanning by the first optical scanner 22 sequentially passes through the first sub lens group RG1, the beam combiner 626, the common sub lens group RG3, and the objective lens system 600, to reach the eye 12. The light used for an angular scanning by the second optical scanner 24 sequentially passes through the second sub lens group RG2, the beam combiner 626, the common sub lens group RG3, and the objective lens system 600, to reach the eye 12.

With the first relay system 601, a relay conjugate position Pr having a conjugate relationship with the first optical scanner 22 is formed in the optical path between the beam combiner 626 and the eye 12. In the example shown in FIG. 41, with the first relay system 601, the relay conjugate position Pr is formed in the optical path between the first relay system 601 and the objective lens system 600. With the second relay system 602, the second optical scanner 24 and the relay conjugate position Pr have a conjugate relationship via the beam combiner 626. With the objective lens system 600, the relay conjugate position Pr and the pupil position of the eye 12 are in a conjugate relationship. Thus, also in the configuration example shown in FIG. 41, the first optical scanner 22 and the pupil position of the eye 12 have a conjugate relationship, and the second optical scanner 24 and the pupil position of the eye 12 have a conjugate relationship. With the relay system used as in the example shown in FIG. 41, the beam combiner 626 in FIG. 41 can have a smaller diameter than the beam combiner 26 in FIG. 3 when obtaining an external irradiation angle as large as that in the example shown in FIG. 3. Thus, the beam combiner can have a smaller diameter, whereby cost can be reduced. For ultra-wide angle ophthalmic optical systems that are likely to have an optical member with a large diameter, a large cost reduction can be expected to be achieved by using the relay system.

In the present embodiment, a configuration is implemented to satisfy the following conditional expression (20), where MR1 represents the paraxial angular magnification of the first relay system 601 from the first optical scanner 22 to the relay conjugate position Pr. and MR2 represents the paraxial angular magnification of the second relay system 602 from the second optical scanner 24 to the relay conjugate position Pr. With the conditional expression (20) satisfied, an effect as in the case that the conditional expression (1) is satisfied can be obtained.

$$|MR1|<|MR2| \quad (20)$$

MR1 preferably satisfies the following conditional expression (21) for the sake of downsizing. According to the conditional expression (20) and the conditional expression (21), the MR2 preferably satisfies the following conditional expression (22).

$$|MR1|=1 \quad (21)$$

$$|MR2|>1 \quad (22)$$

For example, the first sub lens group RG1 shown in FIG. 41 includes, in the following order from the side of the first optical scanner 22 toward the side of the eye, a positive meniscus lens Lr11 having a concave surface facing the side of the first optical scanner 22, a biconvex positive lens Lr12, and a biconcave negative lens Lr13. The lens 112 and the lens Lr13 are cemented to each other so as to form a meniscus-shaped lens component having a convex surface facing the side of the first optical scanner 22.

In the example shown in FIG. 41, the first sub lens group RG1 and the common sub lens group RG3 are configured to be symmetrical about a plane orthogonal to the optical axis. Thus, the common sub lens group RG3 includes, in the following order from the side of the first optical scanner 22 toward the side of the eye, a biconcave negative lens Lr31, a biconvex positive lens Lr32, and a positive meniscus lens Lr33 having a concave surface facing the side of the eye. The lens Lr31 and the lens Lr32 are cemented to each other so as to form a meniscus-shaped lens component having a convex surface facing the side of the eye. The second sub lens group RG2 shown in FIG. 41 has at least one positive lens and at least one negative lens, and has concave surface-shaped lens surfaces facing each other while being separated from each other by an air gap.

In the configuration shown in FIG. 41, the first optical scanner 22 may be configured to perform scanning in one of the X direction and the Y direction. Similarly, the second optical scanner 24 may also be configured to perform scanning in one of the X direction and the Y direction. When the scanners are thus both used as one-dimensional scanners, a two-dimensional angular scanning using beams can be performed on the pupil plane of the eye, with one-dimensional scanner in a direction orthogonal to the primary scanning direction provided at the relay conjugate position Pr obtained with the relay system as a pupil conjugate position.

Figure 42:
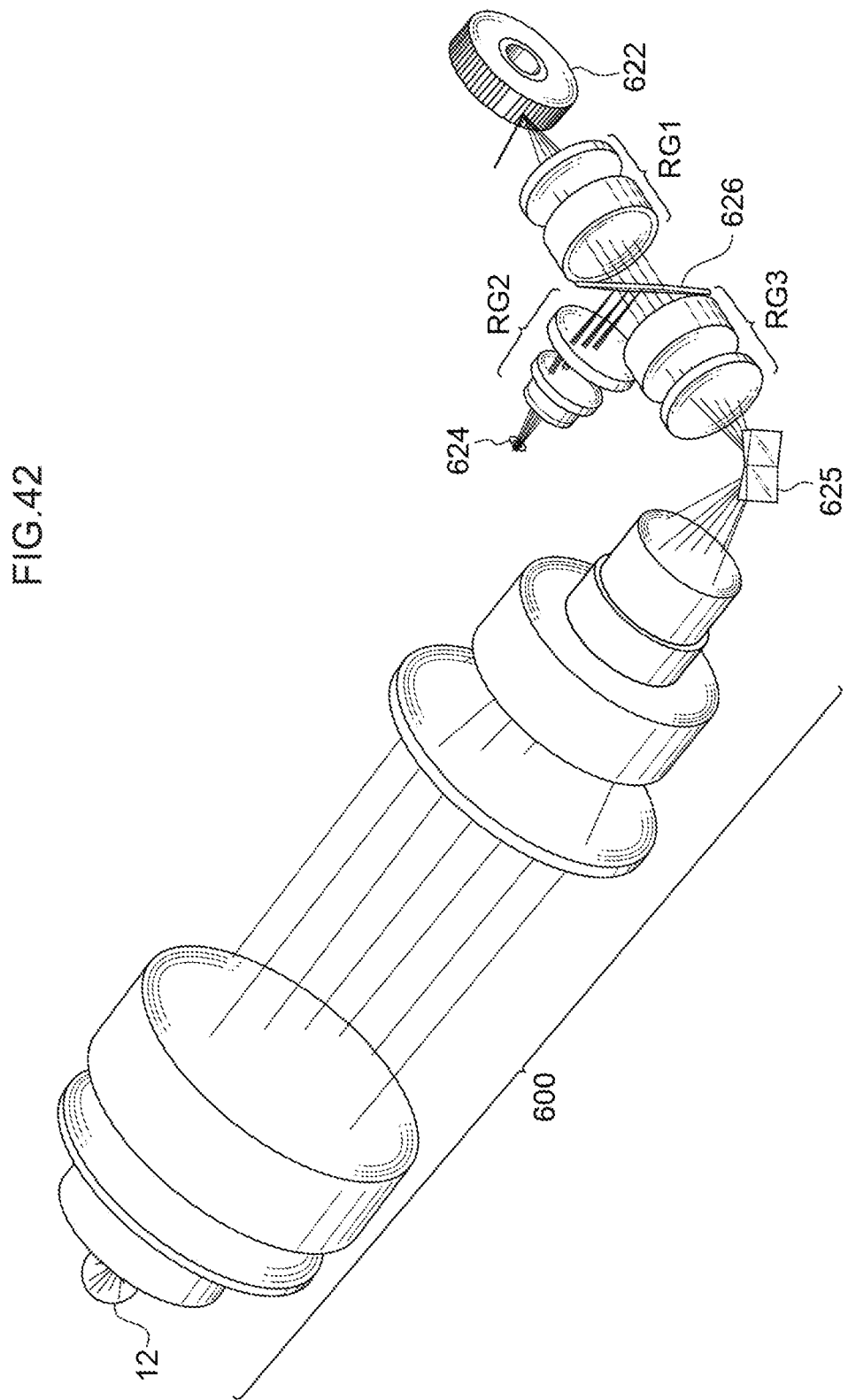
FIG. 42 is a cross-sectional view showing the configuration of an imaging optical system according to still another embodiment.

FIG. 42 is a perspective view showing a configuration of an imaging optical system using the relay system as described above, according to still another embodiment. The configuration shown in FIG. 42 is largely different from the configuration shown in FIG. 41 in that a third optical scanner 625 is disposed at the relay conjugate position Pr, a first optical scanner 622 is disposed instead of the first optical scanner 22 shown in FIG. 41, and a second optical scanner 624 is disposed instead of the second optical scanner 24 shown in FIG. 41. The first optical scanner 622 and the second optical scanner 624 are configured to perform scanning in one of the X direction and the Y direction, and the third optical scanner 625 is configured to perform scanning in a direction orthogonal to the scanning direction of the first optical scanner 622 and the second optical scanner 624. For example, scanning in the Y direction may be performed by using a polygon mirror as the first optical scanner 622, scanning in the Y direction may be performed by using a galvanometer mirror as the second optical scanner 624, and the scanning in the X direction may be performed by using a galvanometer mirror as the third optical scanner 625.

<Practical Example of Embodiment Using Relay System>

As the objective lens system 600 of the imaging optical systems shown in FIG. 41 and FIG. 42, the objective lens systems according to practical examples described in the section <Description of Preferable Practical Examples>. For example, FIG. 41 shows an example where practical example 9-1 described above is used for the objective lens system 600. Table 28 and Table 29 respectively show lens data and the aspherical-surface coefficients of the practical example of the first relay system 601 exemplified in FIG. 41. Table 30 and Table 31 respectively show lens data and the aspherical-surface coefficients of the practical example of the second relay system 602.

TABLE 28

| surface number | radius | thickness | index | abbe number |
|---|---|---|---|---|
| 1 | ∞ | 41.79 | | |
| (ASP) 2 | −87.98 | 11.50 | 1.8210 | 42.5 |
| 3 | −34.81 | 0.50 | | |
| 4 | 47.08 | 16.60 | 1.7432 | 49.3 |
| 5 | −47.08 | 4.00 | 1.8467 | 23.8 |
| 6 | 73.81 | 59.02 | | |
| 7 | −73.81 | 4.00 | 1.8467 | 23.8 |
| 8 | 47.08 | 16.60 | 1.7432 | 49.3 |
| 9 | −47.08 | 0.50 | | |

TABLE 28-continued

| surface number | radius | thickness | index | abbe number |
|---|---|---|---|---|
| 10 | 34.81 | 11.50 | 1.8210 | 42.5 |
| (ASP) 11 | 87.98 | 41.79 | | |

TABLE 29

| surface number | 2 | 11 |
|---|---|---|
| Conic Constant | 0 | 0 |
| 4th Order Coefficient | 0.000E+00 | 0.000E+00 |
| 6th Order Coefficient | −2.079E−06 | 2.079E−06 |
| 8th Order Coefficient | 6.626E−11 | −6.626E−11 |
| 10th Order Coefficient | 3.339E−13 | −3.339E−13 |

TABLE 30

| surface number | radius | thickness | index | abbe number |
|---|---|---|---|---|
| 1 | ∞ | 20.16 | | |
| 2 | 22.40 | 5.00 | 1.8830 | 40.7 |
| 3 | 62.88 | 5.60 | | |
| (ASP) 4 | −37.17 | 3.50 | 1.8030 | 25.5 |
| 5 | 27.78 | 6.30 | | |
| 6 | −26.20 | 9.00 | 1.8830 | 40.7 |
| 7 | −21.30 | 0.50 | | |
| 8 | 51.93 | 9.50 | 1.7725 | 49.6 |
| 9 | −249.44 | 73.71 | | |
| 10 | −73.81 | 4.00 | 1.8467 | 23.8 |
| 11 | 47.08 | 16.60 | 1.7432 | 49.3 |
| 12 | −47.08 | 0.50 | | |
| 13 | 34.81 | 11.50 | 1.8210 | 42.5 |
| (ASP) 14 | 87.98 | 41.79 | | |

TABLE 31

| surface number | 4 | 14 |
|---|---|---|
| Conic Constant | 0 | 0 |
| 4th Order Coefficient | 0.000E+00 | 0.000E+00 |
| 6th Order Coefficient | −1.266E−05 | 2.079E−06 |
| 8th Order Coefficient | 1.592E−07 | −6.626E−11 |
| 10th Order Coefficient | −4.558E−10 | −3.339E−13 |

Table 32 shows corresponding values of the conditional expressions of optical systems as combinations of the practical examples of the relay systems shown in Table 28 to Table 31 and the objective lens system according to the practical example 9-1.

TABLE 32

| | |M1| | |M2| | Mpar | Mmax |
|---|---|---|---|---|
| first relay system + objective lens system | 2.19 | — | 2.19 | 2.75 |
| second relay system + objective lens system | — | 2.50 | 2.50 | 3.30 |

Here, M1 represents a paraxial angular magnification of an optical system as a combination of the first relay system 601 and the objective lens system 600, and M2 represents a paraxial angular magnification of an optical system as a combination of the second relay system 602 and the objective lens system 600. These can be regarded to be the equivalent to the paraxial angular magnifications M1 and M2 in the conditional expression (1), with the SLO objective lens system 31 shown in FIG. 3 replaced with the optical system as a combination of the first relay system 601 and the objective lens system 600 shown in FIG. 41, and with the OCT objective lens system 32 shown in FIG. 3 replaced with the optical system as a combination of the second relay system 602 and the objective lens system 600 shown in FIG. 41. Furthermore, Mpar and Mmax in Table 32 can also be regarded as being equivalent to Mpar and Mmax in the conditional expression (7), with the objective lens system 300 shown in FIG. 7 replaced with the optical system as a combination of the first relay system 601 and the objective lens system 600 shown in FIG. 41, or replaced with the optical system as a combination of the second relay system 602 and the objective lens system 600 shown in FIG. 41.

Table 33 shows corresponding values of the conditional expressions (20) to (22) of the practical examples of the relay systems shown in Table 28 to Table 31.

TABLE 33

| | |MR1| | |MR2| | MRpar | MRmax |
|---|---|---|---|---|
| first relay system | 1.00 | — | 1.00 | 1.00 |
| second relay system | — | 1.14 | 1.14 | 1.20 |

It should be noted that MRpar and MRmax in Table 33 are defined as follows for each relay system. Specifically, $MR=|\omega outR/\omega inR|$ is defined, where $\omega inR$ represents an angle between the incident light ray incident on each relay system from the side of the scanner and the optical axis of each relay system, and $\omega outR$ represents an angle between an exiting light ray exiting from each relay system toward the side of the objective lens system and the optical axis AX. Furthermore, MRpar represents MR in a case that the incident light ray is a paraxial ray, and MRmax represents MR in a case that the incident light ray is a light ray of a maximum angle of view.

<Description about Operation of Image Processor>

Next, an example of the operation of the image processor 17, in a case where the ophthalmic device is constituted of the above-described objective lens system having favorable angular magnification distribution characteristics, as a UWF objective lens system, will be described. In a case where an image is displayed using characteristic data on the angular magnification distribution of the objective lens system, a correction may be sometimes required. An example of a process for the correction will be described with reference to FIG. 34. The following image display process can be applied to both of an SLO image and an OCT image.

For the sake of convenience in description, the control device 16 in FIG. 1 performs the image display process in the following description. For the sake of convenience in description, the image processor 17 is assumed to be composed of an ASIC (application specific integrated circuit). Note that, the ASIC embodies the image processor 17, as an example, in this embodiment, but the technology of the present disclosure is not limited to this. For example, the image processor 17 may be another hardware device, such as a FPGA (field programmable gate array).

In the image display process shown in FIG. 34, in step 500, the image processor 17 sets a scanning area in accordance with a command received by the input/display device 16E. The scanning area is, for example, an area that is set by an upper limit value and a lower limit value of a scanning angle in each of the X direction and the Y direction.

In step 502, the CPU 16A identifies present ωin. Note that, ωin is uniquely identified from a present scanning angle of the scanner.

In step 504, the image processor 17 retrieves angular magnification distribution data on the objective lens system from a lookup table, and retrieves objective lens system data at ωin identified in step 502. The lookup table is a table listing the correspondence between the angle of view and the objective lens system data, i.e. the correspondence between ωin and the objective lens system data, and includes information about the angular magnification distribution. The angular magnification distribution data is data of angular magnification M, as a function of the incident angle ωin, which is the scanning angle of the scanner. Note that, data about a distortion aberration amount as a function of ωin, data about an peripheral light amount as a function of ωin, or the like may be retrieved in addition or instead. The data may be design data or measurement data.

In step 506, the image processor 17 corrects data on a light reception result by the light reception unit, based on the angular magnification distribution data of the objective lens system retrieved in step 504.

In step 508, the image processor 17 generates an image based on the data connected in step 506. In step 510, the input/display device 16E displays the image based on the data generated in step 508, and the image display process ends.

Note that, the above-described image display process is just an example. Therefore, as a matter of course, an unnecessary step may be deleted, a new step may be added, or the order of steps may be permuted within the scope without departing from the spirit of the present invention. U.S. Pat. Nos. 9,039,183 and 9,649,031 and International Publication No. 20141096835 disclose image processes relating to distortion correction in forming a fundus image from detection data for the fundus image, just as described above, and these technologies are included in the present disclosure.

In the above embodiment, the image display process is realized by software of the CPU 16A and hardware of the image processor 17, by way of example, but the technology of the present disclosure is not limited to this. For example, the image display process may be handled only by software using a computer.

In the embodiment described above, a device having functions of both of the SLO system and the OCT system is described. However, the technique of the present disclosure may be applied to form a device having a function of only one of the SLO system and the OCT system.

All of the documents, the patent applications, and the technical standards described in this application are incorporated into this application by reference, to the same extent as a case in which incorporation of each of the documents, the patent applications, and the technical standards by reference is described concretely and individually.

As for the embodiment described above, the following appendices are further disclosed.

APPENDIX 1

An ophthalmic optical system configured to apply a light ray from a light source to an eye, wherein:
ωin represents an angle formed between an incident light ray from a side of the light source into the ophthalmic optical system and an optical axis of the ophthalmic optical system,
ωout represents an angle formed between an exit light ray from the ophthalmic optical system to a side of the eye and the optical axis, and
M is defined as M=|ωout/ωin| in the ophthalmic optical system,
the following conditional expression is satisfied:

$$M\text{par} < M\text{max}$$

wherein Mpar represents M in a case that the incident light ray is a paraxial ray, and
Mmax represents M in a case that the incident light ray is a ray of a maximum angle of view.

APPENDIX 2

The ophthalmic optical system according to appendix 1, wherein the following conditional expression is satisfied:

$$1.1 \times M\text{par} < M\text{max}.$$

APPENDIX 3

The ophthalmic optical system according to appendix 1 or 2, wherein the following conditional expression is satisfied:

$$M\text{max} < 2 \times M\text{par}.$$

APPENDIX 4

The ophthalmic optical system according to any one of appendices 1 to 3, wherein the following conditional expressions are satisfied:

$$1 < M\text{par, and}$$

$$1 < M\text{max}.$$

APPENDIX 5

The ophthalmic optical system according to any one of appendices 1 to 4, wherein a range between Mpar and Mmax comprises a range wherein M increases in conjunction with an increase in ωin.

APPENDIX 6

The ophthalmic optical system according to any one of appendices 1 to 5, wherein the ophthalmic optical system is a refractive optical system, and, when the incident light ray is a ray of a maximum angle of view, ωout is 50 degrees or more.

APPENDIX 7

The ophthalmic optical system according to any one of appendices 1 to 6, comprising, in the following order from the side of the light source:
a meniscus-shaped lens component having a convex surface facing the side of the light source;
a negative lens having a concave surface facing the side of the light source, an absolute value of a radius of curvature of a lens surface on the side of the light source being smaller than an absolute value of a radius of curvature of a lens surface on the side of the eye;
a positive lens having a convex surface facing the side of the eye, an absolute value of a radius of curvature of a lens surface on the side of the eye being smaller than an absolute value of a radius of curvature of a lens surface on the side of the light source;
a positive lens;
a positive lens having a convex surface facing the side of the eye;
a cemented lens constituted of a positive lens having a convex surface facing the side of the eye and a negative lens cemented together;
a positive lens having a convex surface facing the side of the light source; and
a positive meniscus lens having a concave surface facing the side of the eye.

APPENDIX 8

An ophthalmic device, comprising:
the ophthalmic optical system according to any one of appendices 1 to 7; and
a scanner, wherein:
the scanner is disposed in a pupil conjugate position having a conjugate relationship with a pupil position of the eye with respect to the ophthalmic optical system, and the scanner scans the light ray emitted from the light source so as to allow the light ray emitted from the light source to enter the ophthalmic optical system and to scan the eye with the exit light ray.

APPENDIX 9

The ophthalmic device according to appendix 8, further comprising:
a light reception unit for receiving reflected light of the exit light ray from the eye; and
an image processor for correcting data on a light reception result of the light reception unit based on M relating to $\omega$out.

APPENDIX 10

The ophthalmic device according to appendix 9, wherein the image processor generates an image of the eye based on the corrected data.

APPENDIX 11

An ophthalmic optical system configured to apply a light beam scanned at a predetermined scanning angle to an eye, wherein:
$\omega$max represents a maximum value of an angle formed between an exit light beam from the ophthalmic optical system to the eye and an optical axis of the ophthalmic optical system,
Pmax represents a diameter of the exit light beam in a scanning direction at a pupil position of the eye, in a case that the exit scan beam forms an angle of max with respect to the optical axis, and
Pmin represents a diameter of the exit scan beam in the scanning direction at the pupil position of the eye, in a case that the exit scan beam forms a minimum angle with respect to the optical axis,
the following conditional expression is satisfied:

$P\text{max} < P\text{min} \times 0.7/(\cos(\omega\text{max}))$.

APPENDIX 12

The ophthalmic optical system according to appendix 11, wherein the following conditional expression is satisfied:

$P\text{max} < P\text{min}$.

APPENDIX 13

The ophthalmic optical system according to appendix 11 or 12, wherein the following conditional expression is satisfied:

$0.2 \times P\text{min} < P\text{max}$.

APPENDIX 14

The ophthalmic optical system according to any one of appendices 11 to 13, wherein the ophthalmic optical system is a refractive optical system, and, when the incident light beam is a beam of a maximum angle of view, an angle formed between the incident light beam and the optical axis is 50 degrees or more.

APPENDIX 15

The ophthalmic optical system according to any one of appendices 11 to 14, configured to apply the light beam from a light source to the eye, the ophthalmic optical system comprising, in the following order from a side of the light source:
a meniscus-shaped lens component having a convex surface facing the side of the light source;
a negative lens having a concave surface facing the side of the light source, an absolute value of a radius of curvature of a lens surface on the side of the light source being smaller than an absolute value of a radius of curvature of a lens surface on a side of the eye;
a positive lens having a convex surface facing the side of the eye, an absolute value of a radius of curvature of a lens surface on the side of the eye being smaller than an absolute value of a radius of curvature of a lens surface on the side of the light source;
a positive lens;
a positive lens having a convex surface facing the side of the eye;
a cemented lens constituted of a positive lens having a convex surface facing the side of the eye and a negative lens cemented together;
a positive lens having a convex surface facing the side of the light source; and
a positive meniscus lens having a concave surface facing the side of the eye.

APPENDIX 16

An ophthalmic device, comprising:
the ophthalmic optical system according to any one of appendices 11 to 15; and
a scanner, wherein:
the scanner is disposed in a pupil conjugate position having a conjugate relationship with a pupil position of the eye with respect to the ophthalmic optical system, and the scanner scans the light beam emitted from the light source so as to allow the light beam emitted from the light source to enter the ophthalmic optical system and to scan the eye with the exit light beam.

APPENDIX 17

An ophthalmic device, comprising:
a light source: and
an ophthalmic optical system that applies a light ray from the light source to an eye, wherein:
ωin represents an angle formed between an incident light ray from a side of the light source into the ophthalmic optical system and an optical axis of the ophthalmic optical system,
ωout represents an angle formed between an exit light ray from the ophthalmic optical system to a side of the eye and the optical axis, and
M is defined as M=|ωout/ωin| in the ophthalmic optical system,
the following conditional expression is satisfied:

$$M\text{par} < M\text{max}$$

wherein Mpar represents M in a case that the incident light ray is a paraxial ray, and
Mmax represents M in a case that the incident light ray is a ray of a maximum angle of view.

APPENDIX 18

An ophthalmic device, comprising:
a first scanner configured to scan a first light beam at a predetermined maximum scanning angle;
a first objective optical system configured to apply the first light beam incident from the first scanner to an eye, the first objective optical system being configured to form a conjugate relationship between a position of the first scanner and a pupil position of the eye;
a second scanner configured to scan a second light beam different from the first light beam, at a maximum scanning angle that is smaller than the maximum scanning angle of the first scanner;
a second objective optical system configured to apply the second light beam incident from the second scanner to the eye, the second objective optical system being configured to form a conjugate relationship between a position of the second scanner and the pupil position of the eye; and
a beam combiner disposed in an optical path between the first scanner and the eye and an optical path between the second scanner and the eye, the beam combiner being configured to combine an optical path of the first light beam heading for a side of the eye and an optical path of the second light beam heading for the side of the eye, wherein:
the first objective optical system and the second objective optical system have a common optical system on the side of the eye relative to the beam combiner,
wherein M1 represents a paraxial angular magnification of the first objective optical system from the first scanner toward the eye, and
M2 represents a paraxial angular magnification of the second objective optical system from the second scanner toward the eye,
the following conditional expression is satisfied:

$$|M1| < |M2|.$$

APPENDIX 19

The ophthalmic device according to appendix 18, wherein:
the first objective optical system is specific to a scanning laser ophthalmoscope, and the second objective optical system is specific to an optical coherence tomography system; and
the following conditional expressions are satisfied:

$$1.5 < |M1| < 3.5, \text{ and}$$

$$2.5 < |M2| < 5.$$

APPENDIX 20

The ophthalmic device according to appendix 18 or 19, wherein the second scanner scans the second light beam at a lower scan speed than a scan speed at which the first scanner scans the first light beam.

APPENDIX 21

The ophthalmic device according to any one of appendices 18 to 20, wherein the common optical system includes, in the following order from a side of the beam combiner to a side of the eye:
a positive lens having a convex surface facing the side of the eye;
a cemented lens constituted of a positive lens having a convex surface facing the side of the eye and a negative lens cemented together;
a positive lens having a convex surface facing the side of the beam combiner; and
a positive meniscus lens having a concave surface facing the side of the eye.

APPENDIX 22

The ophthalmic device according to any one of appendices 18 to 21, wherein an optical system of the first objective optical system, on a side of the first scanner relative to the beam combiner, comprises, in the following order from the side of the first scanner to the side of the eye:
a meniscus-shaped lens component having a convex surface facing the side of the first scanner.
a negative lens having a concave surface facing the side of the first scanner, an absolute value of a radius of curvature of a lens surface on the side of the first scanner being smaller than an absolute value of a radius of curvature of a lens surface on the side of the eye;
a positive lens having a convex surface facing the side of the eye, an absolute value of a radius of curvature of a lens surface on the side of the eye being smaller than an absolute value of a radius of curvature of a lens surface on the side of the first scanner; and
a positive lens.

APPENDIX 23

The ophthalmic device according to any one of appendices 18 to 22, wherein an optical system of the second objective optical system, on a side of the second scanner relative to the beam combiner, comprises, in the following order from the side of the second scanner to the side of the eye:
a meniscus-shaped lens component having a convex surface facing the side of the second scanner;

a negative lens having a concave surface facing the side of the second scanner, an absolute value of a radius of curvature of a lens surface on the side of the second scanner being smaller than an absolute value of a radius of curvature of a lens surface on the side of the eye;

a positive lens having a convex surface facing the side of the eye, an absolute value of a radius of curvature of a lens surface on the side of the eye being smaller than an absolute value of a radius of curvature of a lens surface on the side of the second scanner; and a positive lens.

APPENDIX 24

An ophthalmic device, comprising:

a first scanner configured to scan a first light beam at a predetermined maximum scanning angle;

a first objective optical system configured to apply the first light beam incident from the first scanner to an eye, the first objective optical system being configured to form a conjugate relationship between a position of the first scanner and a pupil position of the eye;

a second scanner configured to scan a second light beam different from the first light beam, at a maximum scanning angle that is smaller than the maximum scanning angle of the first scanner;

a second objective optical system configured to apply the second light beam incident from the second scanner to the eye, the second objective optical system being configured to form a conjugate relationship between a position of the second scanner and the pupil position of the eye; and a beam combiner disposed in an optical path between the first scanner and the eye and an optical path between the second scanner and the eye, the beam combiner being configured to combine an optical path of the first light beam heading for a side of the eye and an optical path of the second light beam heading for the side of the eye, wherein:

the first objective optical system and the second objective optical system have a common optical system on the side of the eye relative to the beam combiner, wherein β1 represents a paraxial lateral magnification of the first objective optical system from the first scanner to the eye, and β2 represents a paraxial lateral magnification of the second optical system from the second scanner to the eye, the following conditional expression is satisfied:

|β2|<|β1|.

APPENDIX 25

The ophthalmological device according to appendix 24, wherein:

the first objective optical system is specific to a scanning laser ophthalmoscope, and the second objective optical system is specific to an optical coherence tomography system; and the following conditional expressions are satisfied:

0.25<|β1|<0.7, and 0.2<|β2|<0.4.

APPENDIX 26

The ophthalmic device according to appendix 24 or 25, wherein the second scanner scans the second light beam at a lower scan speed than a scan speed at which the first scanner scans the first light beam.

APPENDIX 27

An ophthalmic device, comprising:

a first scanner configured to scan a first light beam at a predetermined first scan speed;

a first objective optical system configured to apply the first light beam incident from the first scanner to an eye, the first objective optical system being configured to form a conjugate relationship between a position of the first scanner and a pupil position of the eye;

a second scanner configured to scan a second light beam different from the first light beam, at a scan speed that is slower than the scan speed of the first scanner;

a second objective optical system configured to apply the second light beam incident from the second scanner to the eye, the second objective optical system being configured to form a conjugate relationship between a position of the second scanner and the pupil position of the eye; and a beam combiner disposed in an optical path between the first scanner and the eye and an optical path between the second scanner and the eye, the beam combiner being configured to combine an optical path of the first light beam heading for a side of the eye and an optical path of the second light beam heading for the side of the eye, wherein:

the first objective optical system and the second objective optical system have a common optical system on the side of the eye relative to the beam combiner, wherein M1 represents a paraxial angular magnification of the first objective optical system from the first scanner toward the eye, and M2 represents a paraxial angular magnification of the second objective optical system from the second scanner toward the eye, the following conditional expression is satisfied:

|M1|<|M2|.

APPENDIX 28

An ophthalmic optical system configured to apply an angular scanning light ray to a side of an eye, wherein:

(1) ωin represents an angle formed between an incident light ray into the ophthalmic optical system and an optical axis of the ophthalmic optical system, (2) ωout represents an angle formed between an exit light ray from the ophthalmic optical system to the side of the eye and the optical axis, and (3) M is defined as M=|ωout/ωin|, the following conditional expression is satisfied:

Mpar<Mmax wherein Mpar represents M in a case that the incident light ray is a paraxial ray, and Mmax represents M in a case that the incident light ray is a ray of a maximum angle of ωin.

APPENDIX 29

The ophthalmic optical system according to appendix 28, wherein the following conditional expression is satisfied:

$1.1 \times M\text{par} < M\text{max}.$

APPENDIX 30

The ophthalmic optical system according to appendix 28, wherein the following conditional expression is satisfied:

$M\text{max} < 2 \times M\text{par}.$

APPENDIX 31

The ophthalmic optical system according to appendix 28, wherein the following conditional expressions are satisfied:

$1 < M\text{par},$ and $1 < M\text{max}.$

APPENDIX 32

The ophthalmic optical system according to any one of appendices 28 to 31, wherein the following conditional expression is satisfied:

$1.5 < M\text{par} < 5.0$

APPENDIX 33

The ophthalmic optical system according to any one of appendices 28 to 32, wherein a range between Mpar and Mmax comprises a range wherein M increases in conjunction with an increase in $\omega$in.

APPENDIX 34

The ophthalmic optical system according to any one of appendices 28 to 33, wherein the ophthalmic optical system is a refractive optical system.

APPENDIX 35

The ophthalmic optical system according to any one of appendices 28 to 34, comprising, in the following order from the opposite side of the eye:
  a meniscus lens component having a concave surface facing the side of the eye;
  a negative lens having a concave surface facing the opposite side of the eye;
  a positive lens having a convex surface facing the side of the eye;
  a positive lens;
  a positive lens having a convex surface facing the side of the eye;
  a cemented lens;
  a positive lens having a convex surface facing the opposite side of the eye; and
  a positive meniscus lens having a concave surface facing the side of the eye.

APPENDIX 36

An ophthalmic device, comprising:
  the ophthalmic optical system according to any one of appendices 28 to 35; and
  a scanner disposed in a conjugate position with a pupil position of the eye with respect to the ophthalmic optical system,
  wherein, the scanner allows the light ray to enter the ophthalmic optical system and scans the light ray in the angle of min.

APPENDIX 37

The ophthalmic device according to appendix 36, wherein $\omega$out is 50 degrees or more when the incident light ray is the ray of the maximum angle of view.

APPENDIX 38

The ophthalmic device according to appendix 36 or 37, further comprising:
  a light reception unit for receiving reflected light from the eye; and
  an image processor for correcting data on a light reception result of the light reception unit based on M relating to $\omega$in controlled by the scanner.

APPENDIX 39

The ophthalmic device according to appendix 38, wherein the image processor generates an image of the eye based on the corrected data.

APPENDIX 40

An ophthalmic optical system configured to apply an angular scanning light beam to a side of an eye, wherein:
  (1) $\omega$max represents a maximum angle formed between an exit scan beam from the ophthalmic optical system and an optical axis of the ophthalmic optical system,
  (2) Pmax represents a diameter of the exit scan beam in a meridional direction at a pupil position of the eye, where the exit scan beam forms an angle of $\omega$max with respect to the optical axis, and
  (3) Pmin represents a diameter of the exit scan beam in the meridional direction at the pupil position of the eye, in a case that the exit scan beam forms a minimum angle with respect to the optical axis,
  the following conditional expression is satisfied:

$P\text{max} < P\text{min} \times 0.7/(\cos(\omega\text{max})).$

APPENDIX 41

The ophthalmic optical system according to appendix 40, wherein the following conditional expression is satisfied:

$P\text{max} < P\text{min}.$

APPENDIX 42

The ophthalmic optical system according to appendix 40, wherein the following conditional expression is satisfied:

$0.2 \times P\text{min} < P\text{max}.$

APPENDIX 43

The ophthalmic optical system according to any one of appendices 40 to 42, wherein the ophthalmic optical system is a refractive optical system.

APPENDIX 44

An ophthalmic device, comprising:
the ophthalmic optical system according to any one of appendices 40 to 43; and
a scanner, wherein:
the scanner is disposed in a conjugate position with the pupil position of the eye with respect to the ophthalmic optical system,
the scanner allows a light beam to enter the ophthalmic optical system in a predetermined range of scanning angle, and
the scanner scans the light beam so as to scan the eye with an exiting light beam from the ophthalmic optical system.

APPENDIX 45

An ophthalmic device according to appendix 44, wherein the angle of the exiting light beam to the eye forms an angle of 50 degrees or more with respect to the optical axis when the incident light beam is a beam of a maximum angle of view.

APPENDIX 46

An ophthalmic optical system configured to apply an angular scanning light ray to a side of an eye, wherein:
(1) $\omega in$ represents an angle formed between an incident light ray into the ophthalmic optical system and the optical axis of the ophthalmic optical system,
(2) $\omega out$ represents an angle formed between an exit light ray from the ophthalmic optical system to the side of the eye and the optical axis, and
(3) M is defined as $M=|\omega out/\omega in|$,
the following conditional expression is satisfied:

$$Mc < Mp$$

wherein Mc represents M in a central portion area of the eye to be scanned including a cross point with the optical axis, and
Mp represents M in a peripheral portion area of the eye to be scanned.

APPENDIX 47

An ophthalmic objective lens configured to transfer an incoming light ray to an outgoing light ray, comprising:
a plurality of lenses arranged along an optical axis, such that the following conditional expression is satisfied:

$$M\text{par} < M\text{max}$$

wherein
$\omega in$ is an angle of the incoming light ray with respect to the optical axis,
$\omega out$ is an angle of the outgoing light ray with respect to the optical axis,
M is defined as $M=|\omega out/\omega in|$,
Mpar is M where the incoming light ray is a paraxial ray, and
Mmax is M where the incoming light ray is a ray of a maximum angle of view.

APPENDIX 48

An ophthalmic objective lens configured to transfer an incoming light beam to an outgoing light beam, comprising:
a plurality of lenses arranged along an optical axis, such that the following conditional expression is satisfied:

$$P\text{max} < P\text{min} \times 0.7/(\cos(\omega\text{max}));$$

wherein
$\omega$max is a maximum angle of the outgoing light beam from the ophthalmic objective lens with respect to the optical axis,
Pmax is a diameter in a meridional direction of the outgoing light beam intersecting a plane perpendicular to the optical axis, the plane located at the position where the outgoing light beam intersects the optical axis, where the outgoing light beam forms an angle of $\omega$max with respect to the optical axis, and
Pmin is a diameter in the meridional direction of the outgoing light beam intersecting the plane, where the angle of the outgoing light beam from the ophthalmic objective lens with respect to the optical axis is minimum.

APPENDIX 49

The ophthalmic optical system, comprising:
an objective lens that leads light from a light source to the eye, wherein the following conditional expression is satisfied:

$$-1 < TL/1f < 1$$

wherein
TL represents a distance between a nearest lens surface of the objective lens to a side of the light source and a nearest lens surface of the objective lens to the side of the eye in an optical axis, and
f represents a focal length of the objective lens.

APPENDIX 50

The ophthalmic optical system according to appendix 49, wherein
the objective lens consisting of a front group having a positive refractive power and a rear group having a positive refractive power, and the rear group is disposed on the side of the eye relative to the front group,
the front group and the rear group are at a maximum air gap away between lens surfaces of the objective lens in the optical axis, and
the following conditional expression is satisfied:

$$1 < fF/fR < 4$$

wherein
fF represents a focal length of the front group, and
fR represents a focal length of the rear group.

APPENDIX 51

The ophthalmic optical system according to appendix 49 or 50, wherein
the objective lens consisting of a front group having a positive refractive power and a rear group having a positive refractive power, and the rear group is disposed on the side of the eye relative to the front group,
the front group and the rear group are at a maximum air gap away between lens surfaces of the objective lens in the optical axis, and the following conditional expression is satisfied:

$0.1 < D/TL < 0.5$ wherein D represents the maximum air gap.

APPENDIX 52

The ophthalmic optical system according to any one of appendix 50 or 51, wherein
the rear group consisting of an A group having a positive refractive power and a B group having a positive refractive power disposed on the side of the eye relative to the A group,
the A group comprises at least one cemented lens having a positive refractive power, and a nearest lens of the A group to the side of the eye has a convex or flat lens surface on the side of the eye,
the B group consists of one or more positive meniscus-shaped lens components having concave surfaces facing the side of the eye, and
the following conditional expression is satisfied:

$0.4 < fB/fR < 2.5$ wherein
fB represents a focal length of the B group, and
fR represents a focal length of the rear group.

APPENDIX 53

The ophthalmic optical system according to appendix 52, wherein
when fAp represents a focal length of a positive lens that constitutes the cemented lens included in the A group,
all positive lenses of all the cemented lenses included in the A group satisfy the following conditional expression:

$0.9 < fAp/fR < 3.7$.

APPENDIX 54

The ophthalmic optical system according to any one of appendices 49 to 53, wherein an angle between an exiting light ray exiting the objective lens toward the side of the eye and the optical axis of the objective lens is 50 degrees or more.

APPENDIX 55

The ophthalmic optical system according to any one of appendices 50 to 53, wherein the front group includes a lens surface having negative refractive power and a lens surface having positive refractive power disposed on the side of the eye of the lens surface having the negative refractive power.

APPENDIX 56

The ophthalmic optical system according to appendix 55, wherein the front group includes a positive meniscus lens having a convex surface facing the side of the eye.

APPENDIX 57

The ophthalmic optical system according to any one of appendices 50 to 53, wherein the front group includes a meniscus lens having a concave surface facing the side of the eye, and further includes a negative lens and a positive lens on the side of the eye of the meniscus lens.

APPENDIX 58

The ophthalmic optical system according to any one of appendices 50 to 52, wherein the front group includes a negative lens and a positive lens disposed on the side of the eye of the negative lens, and an air lens having negative refractive power is formed between the negative lens and the positive lens.

APPENDIX 59

The ophthalmic optical system according to appendix 58, wherein the negative lens and the positive lens are disposed to have concave surfaces facing each other.

APPENDIX 60

The ophthalmic optical system according to appendix 59, wherein the front group further includes a meniscus lens having a concave surface facing the side of the eye and disposed on the opposite side of the eye to the negative lens, and a positive lens disposed on the side of the eye of the positive lens.

APPENDIX 61

The ophthalmic optical system according to appendix 52 or 53, wherein the A group includes one or more cemented lenses.

APPENDIX 62

The ophthalmic optical system according to appendix 52 or 53, wherein the A group includes two or more cemented lenses.

APPENDIX 63

The ophthalmic optical system according to appendix 52 or 53, wherein the B group includes one or more positive meniscus-shaped single lenses.

APPENDIX 64

The ophthalmic optical system according to appendix 52 or 53, wherein the B group consists of one or more positive meniscus-shaped single lenses only.

APPENDIX 65

An ophthalmic device, comprising:
a first scanner configured to output a first scan beam at a first maximum scanning angle;
a first optical system configured to form a SLO system and having a common lens group, the first optical system being configured to form a first conjugate between the first scanner and a pupil of an eye, and to output the first scan beam to the eye through the common lens group;
a second scanner configured to output a second scan beam, the second scanner having a second maximum scanning angle that is smaller than the first maximum scanning angle of the first scanner;
a second optical system configured to form an OCT system and having the common lens group, the second optical system being configured to form a second conjugate between the second scanner and the pupil of the eye, and to output the second scan beam to the eye through the common lens group; and
a beam combiner configured to combine an optical path of the first optical system and an optical path of the second optical system, the beam combiner being disposed between the first scanner and the common lens group and also disposed between the second scanner and the common lens group;
wherein (1) M1 represents a paraxial angular magnification of the first optical system toward the pupil of the eye with respect to the first conjugate and
(2) M2 represents a paraxial angular magnification of the second optical system toward the pupil of the eye with respect to the second conjugate,
the following conditional expression is satisfied:

$|M1|<|M2|.$

APPENDIX 66

The ophthalmic device according to appendix 65, wherein:
the following conditional expressions are satisfied:

$1.5<|M1|<3.5,$ and $2.5<|M2|<5.$

APPENDIX 67

The ophthalmic device according to appendix 65, wherein the second scanner scans the second scan beam at a lower scan speed than a scan speed at which the first scanner scans the first scan beam.

APPENDIX 68

The ophthalmic device according to any one of appendices 65 to 67, wherein the common lens group includes, in the following order from a side of the beam combiner to a side of the eye:
a positive lens having a convex surface facing a side of the eye;
a cemented lens;
a positive lens having a convex surface facing a side of the beam combiner and
a positive meniscus lens having a concave surface facing the side of the eye.

APPENDIX 69

The ophthalmic device according to any one of appendices 65 to 68, wherein, the first optical system comprises, at a side of the first scanner relative to the beam combiner, a first lens group including in the following order from a side of the first scanner to a side of the eye:
a meniscus-shaped lens component having a convex surface facing a side of the first scanner.
a negative lens having a concave surface facing the side of the first scanner;
a positive lens having a convex surface facing a side of the eye; and
a positive lens.

APPENDIX 70

The ophthalmic device according to any one of appendices 65 to 69, wherein the second optical system comprises, at a side of the second scanner relative to the beam combiner, a second lens group including, in the following order from a side of the second scanner to a side of the eye:
a meniscus-shaped lens component having a convex surface facing the side of the second scanner;
a negative lens having a concave surface facing a side of the second scanner;
a positive lens having a convex surface facing a side of the eye; and
a positive lens.

APPENDIX 71

An ophthalmic device, comprising:
a first scanner configured to output a first scan beam at a first maximum scanning angle;
a first optical system configured to form a SLO system and having a common lens group, the first optical system being configured to form a first conjugate between the first scanner and a pupil of an eye, and to output the first scan beam to the eye through the common lens group;
a second scanner configured to output a second scan beam, the second scanner having a second maximum scanning angle that is smaller than the first maximum scanning angle of the first scanner;
a second optical system configured to form an OCT system and having the common lens group, the second optical system being configured to form a second conjugate between the second scanner and the pupil of the eye, and to output the second scan beam to the eye through the common lens group; and
a beam combiner configured to combine an optical path of the first optical system and an optical path of the second optical system, the beam combiner being disposed between the first scanner and the common lens group, and also disposed between the second scanner and the common lens group; and
wherein (1) β1 represents a paraxial lateral magnification of the first optical system from the first scanner to the eye, and
(2) β2 represents a paraxial lateral magnification of the second optical system from the second scanner to the eye,
the following conditional expression is satisfied:

$|\beta 2|<|\beta 1|.$

APPENDIX 72

The ophthalmological device according to appendix 54, wherein:
the following conditional expressions are satisfied:

$0.25<|\beta 1|<0.7,$ and $0.2<|\beta 2|<0.4.$

APPENDIX 73

The ophthalmic device according to appendix 54, wherein the second scanner scans the second scan beam at a lower scan speed than a scan speed at which the first scanner scans the first scan beam.

APPENDIX 74

An ophthalmic device, comprising:
a first scanner configured to scan a first scan beam at a first scan speed;
a first optical system configured to form a SLO system and having a common lens group, the first optical system being configured to form a first conjugate between the first scanner and a pupil of an eye, and to output the first scan beam to the eye through the common lens group;
a second scanner configured to scan a second scan beam, different from the first scan beam, at a second scan speed that is lower than the first scan speed of the first scanner;
a second optical system configured to form an OCT system and having the common lens group, the second optical system being configured to form a second conjugate between the second scanner and the pupil of the eye, and to output the second scan beam to the eye through the common lens group; and
a beam combiner configured to combine an optical path of the first optical system and an optical path of the second optical system, the beam combiner being disposed between the first scanner and the common lens group and also disposed between the second scanner and the common lens group;
wherein (1) M1 represents a paraxial angular magnification of the first optical system toward the pupil of the eye with respect to the first conjugate, and
(2) M2 represents a paraxial angular magnification of the second optical system toward the pupil of the eye with respect to the second conjugate, the following conditional expression is satisfied:

$|M1|<|M2|.$

APPENDIX 75

An ophthalmic device, comprising:
a first scanner configured to output a first scan beam in a first scanning angle range;
a first optical system configured to form a SLO system and having a common lens group, the first optical system being configured to form a first conjugate between the first scanner and a pupil of an eye, and to output the first scan beam to the eye with a first external irradiation angle $\Theta 1$ through the common lens group;
a second scanner configured to output a second scan beam in a second scanning angle range that is smaller than the first scanning angle range;
a second optical system configured to form an OCT system and having the common lens group, the second optical system being configured to form a second conjugate between the second scanner and the pupil of the eye, and to output the second scan beam to the eye with a second external irradiation angle $\Theta 2$ through the common lens group;
a beam combiner configured to combine an optical path of the first optical system and an optical path of the second optical system, the beam combiner being disposed between the first scanner and the common lens group and also disposed between the second scanner and the common lens group; and wherein the following conditional expression is satisfied:

$\Theta 1=\Theta 2.$

APPENDIX 76

An ophthalmic device according to appendix 75, wherein the first external irradiation angle $\theta 1$ and the second external irradiation angle 82 are both 100 degrees or more.

APPENDIX 77

The ophthalmic device according to any one of appendices 65 to 76, wherein
the first optical system has a first relay system that forms a relay conjugate position having a third conjugate with the first scanner in an optical path between the beam combiner and the eye, and
the second optical system has a second relay system that forms a fourth conjugate between the second scanner and the relay conjugate position.

APPENDIX 78

The ophthalmic device according to appendix 77 further comprising:
a third scanner disposed in the relay conjugate position, wherein
a scanning direction of the third scanner is orthogonal to a scanning direction of the first scanner and a scanning direction of the second scanner.

APPENDIX 79

The ophthalmic device according to appendix 78 or 79, wherein
when MR1 represents a paraxial angular magnification of the first relay system toward the relay conjugate position with respect to the third conjugate, and
MR2 represents a paraxial angular magnification of the second relay system toward the relay conjugate position with respect to the fourth conjugate, the following conditional expression is satisfied:

$|MR1|<|MR2|.$

APPENDIX 80

The ophthalmic device according to appendix 79 satisfying the following conditional expression:

$|MR1|=1.$

APPENDIX 81

The ophthalmic device according to appendix 79 or 80 satisfying the following conditional expression:

$|MR2|>1.$

APPENDIX 82

The ophthalmic device according to any one of appendices 77 to 81, wherein
the first relay system has, in the following order from the side of the first scanner, a first sub lens group and a common sub lens group included in the common lens group,
the second relay system has, in the following order from the side of the second scanner, a second sub lens group and the common sub lens group, and the beam combiner is disposed between the first sub lens group and the common sub lens group and between the second sub lens group and the common sub lens group.

APPENDIX 83

The ophthalmic device according to appendix 82, wherein the first scan beam passing between the first sub lens group and the common sub lens group is parallel light, and
the second scan beam passing between the second sub lens group and the common sub lens group is parallel light.

APPENDIX 84

The ophthalmic device according to appendix 80, wherein the first relay system has, in the following order from the side of the first scanner, a first sub lens group and a common sub lens group included in the common lens group,
the first sub lens group has a positive meniscus lens having a concave surface facing the side of the first scanner, and a meniscus-shaped lens component having a convex surface facing the side of the first scanner, and
the first sub lens group and the common sub lens group are configured to be symmetrical with respect to a plane orthogonal to an optical axis.

APPENDIX 85

The ophthalmic device according to appendix 82, wherein the second sub lens group has at least one positive lens and at least one negative lens, and has concave lens surfaces opposite to each other that are at an air gap away.

APPENDIX 86

The ophthalmic device according to any one of appendices 82 to 85, wherein
the common lens group includes the common sub lens group and an objective lens disposed more on the side of the eye than the relay conjugate position is, and
the objective lens includes, in the following order from the side of the relay conjugate position, a front group having positive refractive power, and a rear group having positive refractive power and separated from the front group by a maximum air gap on an optical axis between the lens surfaces of the objective lens.

APPENDIX 87

The ophthalmic device according to appendix 86, wherein the front group includes, in the following order from the side of the relay conjugate position, a positive lens and a negative lens.

APPENDIX 88

The ophthalmic device according to appendix 86 or 87, wherein the rear group includes, in the following order from the side of the relay conjugate position, a cemented lens having positive refractive power, a positive lend, and a positive meniscus lens having a concave surface facing the side of the eye.

EXPLANATION OF REFERENCES

12 EYE
19 IMAGING OPTICAL SYSTEM
22, 622 FIRST OPTICAL SCANNER
24, 624 SECOND OPTICAL SCANNER
26, 626 BEAM COMBINER
27 PUPIL
28 COMMON LENS GROUP
30 WIDE ANGLE OPTICAL SYSTEM
31 SLO OBJECTIVE LENS SYSTEM
32 OCT OBJECTIVE LENS SYSTEM
110 OPHTHALMIC DEVICE
300, 600 OBJECTIVE LENS SYSTEM
601 FIRST RELAY SYSTEM
602 SECOND RELAY SYSTEM
625 THIRD OPTICAL SCANNER
AX OPTICAL AXIS
G1 FIRST LENS GROUP
G2 SECOND LENS GROUP
G3 THIRD LENS GROUP
GF FRONT GROUP
GR REAR GROUP
GRA A GROUP
GRB B GROUP
PR RELAY CONJUGATE POSITION
RG1 FIRST SUB LENS GROUP
RG2 SECOND SUB LENS GROUP
RG3 COMMON SUB LENS GROUP

What is claimed is:

1. An ophthalmic device, comprising:
a first scanner configured to output a first scan beam at a first maximum scanning angle;
a first optical system configured to form a SLO system and having a common lens group, the first optical system being configured to form a first conjugate between the first scanner and a pupil of an eye, and to output the first scan beam to the eye through the common lens group;
a second scanner configured to output a second scan beam, the second scanner having a second maximum scanning angle that is smaller than the first maximum scanning angle of the first scanner;
a second optical system configured to form an OCT system and having the common lens group, the second optical system being configured to form a second conjugate between the second scanner and the pupil of the eye, and to output the second scan beam to the eye through the common lens group; and
a beam combiner configured to combine an optical path of the first optical system and an optical path of the second optical system, the beam combiner being disposed between the first scanner and the common lens group and also disposed between the second scanner and the common lens group;
wherein (1) M1 represents a paraxial angular magnification of the first optical system toward the pupil of the eye with respect to the first conjugate and
(2) M2 represents a paraxial angular magnification of the second optical system toward the pupil of the eye with respect to the second conjugate,
the following conditional expression is satisfied:

$|M1|<|M2|.$

2. The ophthalmic device according to claim 1, wherein: the following conditional expressions are satisfied:

$1.5<|M1|<3.5$, and $2.5<|M2|<5.$

3. The ophthalmic device according to claim 1, wherein the second scanner scans the second scan beam at a lower scan speed than a scan speed at which the first scanner scans the first scan beam.

* * * * *